United States Patent [19]

Farge et al.

[11] Patent Number: 4,622,393

[45] Date of Patent: Nov. 11, 1986

[54] 3-VINYL-CEPHALOSPORINS AND THEIR PREPARATIONS

[75] Inventors: Daniel Farge; Pierre Le Roy, both of Thiais; Claude Moutonnier, Le Plessis Robinson; Jean-François Peyronel, Palaiseau, all of France

[73] Assignee: Rhone-Poulenc Industries, Paris, France

[21] Appl. No.: 610,175

[22] Filed: May 14, 1984

Related U.S. Application Data

[63] Continuation of Ser. No. 322,931, Nov. 19, 1981, abandoned.

[30] Foreign Application Priority Data

Nov. 20, 1980 [FR] France .................. 80 24635

[51] Int. Cl.$^4$ .................................. C07D 501/24
[52] U.S. Cl. .................................. 540/215; 540/217; 540/222; 540/227; 540/229
[58] Field of Search .................. 544/16, 17, 22, 27, 544/29

[56] References Cited

U.S. PATENT DOCUMENTS

| | | | |
|---|---|---|---|
| 3,962,227 | 6/1976 | Chauvette | 544/22 |
| 3,994,884 | 11/1976 | Weir | 544/22 |
| 4,065,620 | 12/1977 | Webber | 544/16 |
| 4,258,041 | 3/1981 | O'Callaghan | 544/25 |
| 4,266,049 | 5/1981 | Bonjouklian | 544/16 |
| 4,278,793 | 7/1981 | Durckheimer et al. | 544/27 |
| 4,307,230 | 12/1981 | Farge et al. | 544/29 |

FOREIGN PATENT DOCUMENTS

2130582 6/1984 United Kingdom .

OTHER PUBLICATIONS

Seyferth et al., J. American Chemical Society, 82, pp. 1510–1511 (1960).
Bestmann, "Angew. Chem. Internat. Edit., 4(8) p. 646 (1965).
Organic Reactions, 5, 28 (1949).
March, "Advanced Organic Chemistry," 2nd Ed., 1977, p. 434.
Brown, J. Amer. Chem. Soc., 89, pp. 531–532, (1967).

*Primary Examiner*—Sidney Marantz
*Assistant Examiner*—Robert Benson
*Attorney, Agent, or Firm*—Stevens, Davis, Miller & Mosher

[57] ABSTRACT

New 3-vinylcephalosporins of the general formula (I),

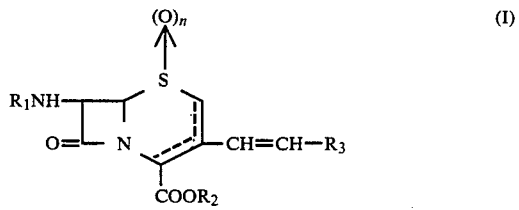

in which n=0 or 1, $R_1$ is a radical of the general formula (II),

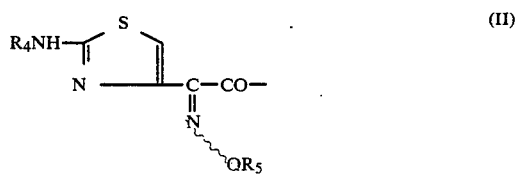

in which $R_4$ is hydrogen or a protective radical and $R_5$ represents a radical of the general formula (IIa)

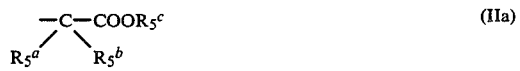

in which $R^a_5$ and $R^b_5$ are hydrogen or alkyl or together form an alkylene radical and $R^c_5$ is hydrogen or a protective radical, $R_2$ is hydrogen, a protective radical or a radical which can easily be removed by an enzymatic method, and $R_3$ is a halogen atom or a radical $R'_3SO_2O$— or $R''_3CO$—O—, in which radicals $R'_3$ and $R''_3$ are substituted or unsubstituted alkyl or phenyl radicals, or alternatively $R_1$ is a hydrogen atom or a radical of the general formula (II) in which $R_4$ is defined as above and $R_5$ is hydrogen, alkyl, vinyl, cyanomethyl or a protective radical, and $R_2$ is defined as above, or $R_1$ is hydrogen or a variously substituted acyl radical and $R_2$ is hydrogen or a protective radical, and $R_3$ is a halogen atom.

These new products are useful as intermediates for the preparation of antibiotic cephalosporins.

11 Claims, No Drawings

3-VINYL-CEPHALOSPORINS AND THEIR PREPARATIONS

This application is a continuation of application Ser. No. 322,931, filed Nov. 19, 1981, abandoned.

DESCRIPTION

The present invention relates to new 3-vinylcephalosporins of the general formula:

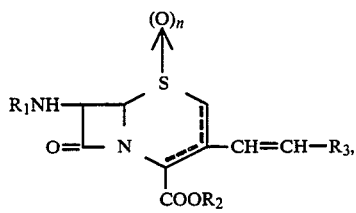

their salts and their preparation.

French Patent Application Nos. 2,081,451 and 2,137,899 describe the preparation of 3-vinylcephalosporin derivatives. In these products, the vinyl chain does not carry an acyloxy or halogen substituent.

The products of the general formula (I), in which n is equal to 0 or 1, are in the form of a bicyclooct-2-ene or bicyclooct-3-ene (according to the nomenclature of Chemical Abstracts) if n=0, or in the form of a bicyclooct-2-ene if n=1, the substituent on the carbon atom in the 3-position of the bicyclooctene exhibiting cis-/trans stereoisomerism, and 1.(a) the symbol $R_1$ represents a hydrogen atom, a radical of the general formula:

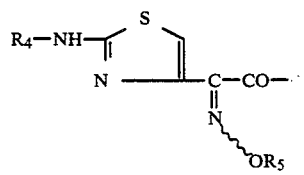

[in which $R_4$ is a hydrogen atom or an amine-protecting radical (such as t-butoxycarbonyl, 2,2,2-trichloroethoxycarbonyl, chloroacetyl, trichloroacetyl, trityl, benzyl, dibenzyl, benzyloxycarbonyl, p-nitrobenzyloxycarbonyl, p-methoxybenzyloxycarbonyl, formyl or trifluoroacetyl) and $R_5$ is a hydrogen atom, an alkyl, vinyl or cyanomethyl radical or an oxime-protecting group such as trityl, tetrahydropyranyl or 2-methoxyprop-2-yl], a benzhydryl or trityl radical, an acyl radical of the general formula:

   $R_6CO—$   (III)

in which $R_6$ is hydrogen atom, an alkyl radical [optionally substituted by one or more halogen atoms or by a phenyl or phenoxy radical] or a phenyl radical, a radical of the general formula:

   $R_7OCO—$   (IV)

{in which $R_7$ is an unsubstituted branched alkyl radical or a linear or branched alkyl radical carrying one or more substituents [chosen from amongst halogen atoms, cyano, trialkylalkyl and phenyl radicals and the phenyl radical substituted by one or more alkoxy, nitro or phenyl radicals] or a vinyl, allyl or quinolyl radical} or a nitrophenylthio radical, or alternatively $R_1NH—$ is replaced by a methyleneamino radical in which the methylene radical is substituted by a dialkylamino group or an aryl group (which is itself optionally substituted by one or more methoxy or nitro radicals), and the symbol $R_2$ represents a hydrogen atom, a radical which can easily be removed by an enzymatic method, of the general formula:

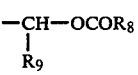   (V)

[in which $R_8$ represents an alkyl radical or the cyclohexyl radical and $R_9$ represents a hydrogen atom or an alkyl radical] or a methoxymethyl, t-butyl, benzhydryl, nitrobenzyl or p-methoxybenzyl radical, or alternatively 1.(b) the symbol $R_1$ represents a hydrogen atom, an alkanoyl radical containing 1 to 8 carbon atoms or an alkanoyl radical containing 2 to 8 carbon atoms, which is substituted (by chlorine or bromine atoms), an azidoacetyl or cyanoacetyl radical, an acyl radical of the general formula:

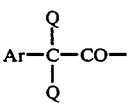   (VI)

in which each Q is H or methyl and Ar represents a thien-2-yl, thien-3-yl, furan-2-yl, furan-3-yl, pyrrol-2-yl or pyrrol-3-yl radical or a phenyl radical [optionally substituted by halogen atoms, trifluoromethyl or hydroxyl radicals, alkyl radicals (containing 1 to 3 carbon atoms), alkoxy radicals (containing 1 to 3 carbon atoms) or cyano or nitro radicals, at least one of which is located in the meta-position or para-position of the phenyl], an acyl radical of the general formula:

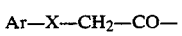   $Ar—X—CH_2—CO—$   (VII)

in which X is oxygen or sulphur and Ar is defined as above, or $Ar—X—$ represents pyrid-4-yl-thio, an acyl radical corresponding to the general formula:

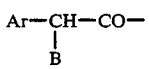   (VIII)

in which Ar is defined as above and B represents an amino radical, an amino radical protected by a benzyloxycarbonyl, alkoxycarbonyl, cyclopentyloxycarbonyl, cyclohexyloxycarbonyl, benzhydryloxycarbonyl, trityl or 2,2,2-trichloroethoxycarbonyl group, a sulpho radical, a hydroxyl or carboxyl radical [optionally protected by esterification with respectively an alkanoic acid or an alcohol (containing 1 to 6 carbon atoms)] or an azido, cyano or carbamoyl radical, a (3-sydnone)-2-alkanoyl radical (the alkanoyl part of which contains 1 to 3 carbon atoms), a radical of the general formula:

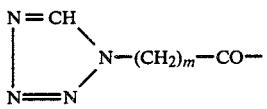 (IX)

in which m is 0 to 2, or a 5-aminoadipoyl radical [in which the amino group is optionally protected by an alkanoyl radical (containing 1 to 3 carbon atoms and optionally substituted by a chlorine atom) and in which the carboxyl group is protected by a benzhydryl or 2,2,2-trichloroethyl group, a t-alkyl group (containing 4 to 6 carbon atoms) or a nitrobenzyl group], or alternatively $R_1NH$ is replaced by a cyclic imide group of a dicarboxylic acid, and the symbol $R_2$ represents a hydrogen atom, a t-alkyl radical containing 4 to 6 carbon atoms, a t-alkenyl radical containing 6 or 7 carbon atoms, a t-alkynyl radical containing 6 or 7 carbon atoms or a benzyl, methoxybenzyl, nitrobenzyl, 2,2,2-trichloroethyl, benzhydryl, succinimidomethyl or phthalimidomethyl radical, and the symbol $R_3$ represents a halogen atom such as chlorine, bromine or iodine;

2. the symbol $R_1$ represents a radical of the general formula (II) in which the symbol $R_5$ represents a radical of the general formula:

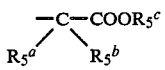 (IIa)

[in which $R^a_5$ and $R^b_5$ are either identical or different and represent hydrogen atoms or alkyl radicals, or together form an alkylene radical containing 2 to 3 carbon atoms, and $R^c_5$ represents a hydrogen atom or an acid-protecting radical such as methoxymethyl, t-butyl, benzhydryl, benzyl, nitrobenzyl and p-methoxybenzyl], the symbol $R_2$ is defined as above under 1.(a) and the symbol $R_3$ represents a radical of the general formula:

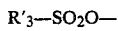 (X)

or

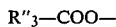 (XI)

(in which formulae $R'_3$ represents an alkyl, trifluoromethyl or trichloromethyl radical or a phenyl radical which is unsubstituted or substituted by a halogen atom or by an alkyl or nitro radical, and $R''_3$ is defined in the same way as $R'_3$ or represents an acylmethyl, 2-acylethyl, 2-acylpropyl, alkoxycarbonylmethyl, 2-alkoxycarbonylethyl or 2-alkoxycarbonylpropyl radical) or a halogen atom (such as chlorine, bromine and iodine).

It is understood that (unless otherwise mentioned) the alkyl or acyl portions or radicals which have been mentioned above (or which will be mentioned below) are linear or branched and contain 1 to 4 carbon atoms, and that the mixtures of the bicyclooct-2-ene and bicyclooct-3-ene isomers and/or cis and trans isomers fall within the scope of the invention.

In the following text, the trans stereoisomer is designated by E and the cis stereoisomer is designated by Z.

Furthermore, the group —$OR_5$ of the radical of the general formula (II) can be in either the syn or anti position, and these isomers and mixtures thereof also fall within the scope of the invention.

The syn form can be represented by the formula:

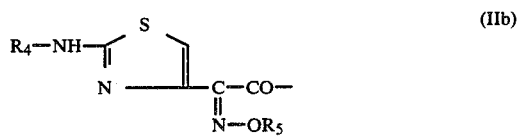 (IIb)

The anti form can be represented by the formula:

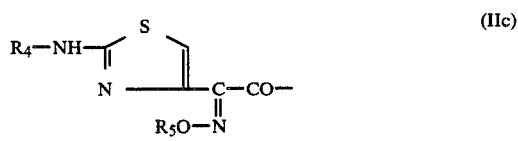 (IIc)

If $R^a_5$ and $R^b_5$ are different, diastereoisomers also exist. The isomers and mixtures thereof also fall within the scope of the present invention.

Ia. According to the invention, the products of the general formula (I) {in which, n being defined as above, (a'$_1$) the symbols $R_1$ and $R_2$ are defined as in the general formula (I) under 1.(a), except that $R_1$ cannot represent a hydrogen atom, or alternatively the symbol $R_1$ represents an alkanoyl radical containing 1 to 8 carbon atoms, an alkanoyl radical containing 2 to 8 carbon atoms, which is substituted by chlorine or bromine atoms, an acyl radical of the general formula (VI) in which Q is H or methyl and Ar represents a thien-2-yl, thien-3-yl, furan-2-yl, furan-3-yl, pyrrol-2-yl or pyrrol-3-yl radical or a phenyl radical [optionally substituted by halogen atoms, hydroxyl radicals, alkyl radicals (containing 1 to 3 carbon atoms) or alkoxy radicals (containing 1 to 3 carbon atoms), at least one of which is located in the meta-position or para-position of the phenyl], an acyl radical of the general formula (VII), an acyl radical corresponding to the general formula (VIII) in which Ar is defined as above and B represents an amino radical protected by a benzyloxycarbonyl, alkoxycarbonyl, cyclopentyloxycarbonyl, cyclohexyloxycarbonyl, benzhydryloxycarbonyl, trityl or 2,2,2-trichloroethoxycarbonyl group, a sulpho radical, a hydroxyl or carboxyl radical [optionally protected by esterification with an alkanoic acid or an alcohol (containing 1 to 6 carbon atoms)] or a 5-aminoadipoyl radical [in which the amino group is optionally protected by an alkanoyl radical (containing 1 to 3 carbon atoms and optionally substituted by a chlorine atom) and in which the carboxyl group is protected by a benzhydryl or 2,2,2-trichloroethyl group, a t-alkyl group (containing 4 to 6 carbon atoms) or a nitrobenzyl group], or alternatively $R_1NH$ is replaced by a cyclic imide group of a dicarboxylic acid, $R_2$ is defined as in the general formula (I) under 1.(b) and the symbol $R_3$ is defined as in the general formula (I) under 1., or (b'$_1$) the symbols $R_1$, $R_2$ and $R_3$ are defined as in the general formula (I) under 2.} can be prepared by reacting an activated form of an acid $R'_3SO_3H$ or $R''_3COOH$, of the type:

 (XII)

 (XIII)

 (XIV)

R''₃COHal (XV)

(in which R' and R'' are defined as above and Hal represents a halogen atom), or a halogenating agent, with a product of the general formula:

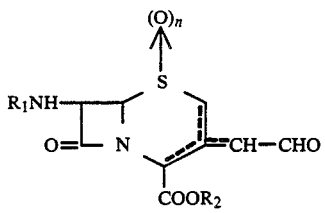

(XVI)

[in which, n being defined as above, the product is in the form of a 3-oxoethyl-bicycloct-2-ene or -bicycloct-3-ene or a 3-oxoethylidenebicyclooctane if n=0, and in the form of a 3-oxoethylbicycloct-2-ene or a 3-oxoethylidenebicyclooctane if n=1, $R_1$ is defined as above (except that it cannot represent a radical of the general formula (II) in which $R_4$ is hydrogen) and $R_2$ is defined as above (except that it cannot represent hydrogen)], or with a mixture of its isomers, and then, if appropriate, reducing the sulphoxide obtained and, if appropriate removing the protective groups of the amine group of the radical of the general formula (II) and/or, if appropriate, of the acid groups, if it is desired to obtain a product of the general formula (I) in which the amine and/or acid groups are free.

It is understood that if $R_1$ is a radical of the general formula (II) in which $R_5$ is a hydrogen atom, it is necessary to protect the oxime by a group such as indicated above, which can subsequently be removed under the conditions indicated below.

The reaction is generally carried out in the presence of a tertiary base of the general formula:

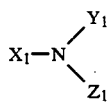

(XVII)

in which $X_1$, $Y_1$ and $Z_1$ represent alkyl or phenyl radicals or, if appropriate, two of them form a ring with the nitrogen atom to which they are attached, (e.g. in the presence of triethylamine or dimethylaniline), in a chlorinated organic solvent (e.g. methylene chloride), in an ester (e.g. ethyl acetate), in an ether (e.g. dioxane or tetrahydrofuran), in an amide (e.g. dimethylacetamide, dimethylformamide or hexamethylphosphorotriamide), in acetonitrile or N-methylpyrrolidone, or in a mixture of such solvents, or directly in a basic solvent such as pyridine, or alternatively, if $R_3$ is other than a halogen atom, the reaction can be carried out in an aqueous-organic medium, in the presence of an alkaline condensation agent (e.g. an alkali metal bicarbonate, sodium hydroxide or potassium hydroxide), at a temperature between −78° C. and the reflux temperature of the reaction mixture.

If appropriate, the reaction is carried out under nitrogen.

If it is desired to prepare a product of the general formula (I) in which $R_3$ is a halogen atom, the halogenating agents can be chosen from amongst halogen derivatives of phosphorus, in particular:

halogen/triaryl phosphite addition compounds, or phosphorus trichloride, phosphorus oxychloride, phosphorus pentachloride, dichlorotriphenylphosphorane or catechyltrichlorophosphorane if $R_3$ is a chlorine atom, or phosphorus tribromide, phosphorus oxybromide, phosphorus pentabromide or catechyltribromophosphorane if $R_3$ is a bromine atom.

If phosphorus trichloride (or tribromide) is used, this reagent is reacted with a product of the general formula (XVI) in which n=0.

Catechyltrichlorophosphorane (or catechyltribromophosphorane), which can be prepared in situ, can be obtained in accordance with the method described by H. Gross and U. Karsch, J. Prakt. Chem., 29, 315 (1965).

Halogen/triaryl phosphite addition compounds, which can be formed in situ, are described by H. N. Rydon and B. L. Tonge, J. Chem. Soc., 3,043 (1956), by J. Michalski et al., J. Org. Chem., 45, 3,122 (1980), or in Belgian Pat. No. 881,424, and can be prepared in accordance with the methods mentioned in these documents.

The preparation of the halogen derivatives of the general formula (I) is carried out in an anhydrous medium, starting from a product of the general formula (XVI) in which $R_1$ is protected if it contains an acid group.

If the radical $R_1$ is capable of forming an imino halide, it is important not to use an excess of halogenating reagent.

The reduction of the S-oxide can be carried out under the conditions described in German Patent Application No. 2,637,176.

If necessary, the removal of the protective radicals of the amine group and of the acid groups is carried out in a single step or in 2 steps.

By way of example:

1. The removal of the amine-protecting groups is carried out:

in the case of a t-butoxycarbonyl, trityl, p-methoxybenzyloxycarbonyl or formyl radical: by treatment in an acid medium. Preferably, trifluoroacetic acid is used, the reaction being carried out at a temperature between 0° and 20° C., or alternatively anhydrous or aqueous formic, orthophosphoric or polyphosphoric acids at a temperature between 20° and 60° C., or para-toluenesulphonic or methylsulphonic acid is used, in acetone or in acetonitrile, at a temperature between 20° C. and the reflux temperature of the reaction mixture. Under these conditions, the product of the general formula (I) can be obtained in the form of the trifluoroacetate, the solvate with formic acid, the methylsulphonate, the phosphate or the para-toluenesulphonate, from which the amine group can be freed by any method which is in itself known for obtaining an amine from one of its salts without affecting the rest of the molecule. The reaction is carried out, in particular, by bringing the compound into contact with an ion exchange resin or by reaction with an organic base.

in the case of a 2,2,2-trichloroethoxycarbonyl or p-nitrobenzyloxycarbonyl radical: by reduction (in particular treatment with zinc in acetic acid).

in the case of a chloroacetyl or trichloroacetyl radical: by applying the method described in the French Patent published under No. 2,243,199. in the case of a benzyl, dibenzyl or benzyloxycarbonyl radical: by catalytic hydrogenation.

in the case of a trifluoroacetyl radical: by treatment in a basic medium.

2. The removal of the protective groups of carboxyl radicals is carried out:

in the case of a t-butyl, p-methoxybenzyl or benzhydryl group: by treatment in an acid medium, under the conditions described above for the removal of the amino-protecting trityl radical. In the case of the benzhydryl radical, the reaction can be carried out in the presence of anisole.

in the case of a methoxymethyl group: by treatment in a dilute acid medium.

in the case of a nitrobenzyl group: by reduction (in particular treatment with zinc in acetic acid or hydrogenolysis).

3. The removal of the oxime-protecting group is carried out:

in the case of a trityl or tetrahydropyranyl group: by acidolysis, e.g. with trifluoroacetic acid, aqueous or non-aqueous formic acid or para-toluenesulphonic acid.

in the case of the 2-methoxyprop-2-yl group: in accordance with the method described in Belgian Pat. No. 875,379.

Ib. According to the invention, if the products of the general formula (I) defined above under (a'$_1$) and (b'$_1$), in which R$_3$ is a chlorine or bromine atom, are prepared by process Ia., depending on the operating conditions, it is possible to isolate the dihalogen intermediate of the general formula:

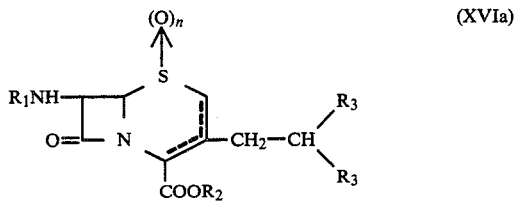

(XVIa)

(in which R$_1$, R$_2$, R$_3$ and n are defined as above, it being understood that R$_2$ does not represent the hydrogen atom, if n=0, the product is in the form of a bicyclooct-2-ene or bicyclooct-3-ene and if n=1, the product is in the form of a bicyclooct-2-ene), which can then be dehydrohalogenated.

If it is desired to isolate the dihalogen intermediate, the reaction is carried out with a halogenating agent, in an organic solvent such as a chlorinated solvent (e.g., methylene chloride, chloroform, carbon tetrachloride or 1,2-dichloroethane), an ether (e.g. ethyl ether, propylene oxide, tetrahydrofuran or dioxane), or an amide (e.g. dimethylacetamide, dimethylpropionamide, dimethylformamide, N-acetylmorpholine, N-acetylpiperidine or N-methylpyrrolidone), or in a mixture of such solvents, at a temperature which is slightly lower than for the preparation of the corresponding halogenovinyl derivative, i.e. between −78° and 30° C. It is also possible to carry out the reaction in the presence of a base such as pyridine, in one of the abovementioned solvents, at a temperature between −78° and 0° C.

The dehydrohalogenation is carried out in the presence of a tertiary base such as defined above, an aromatic amine (e.g. pyridine, picoline or quinoline) or an inorganic base (such as sodium hydroxide, potassium hydroxide, an alkali metal carbonate or bicarbonate or an alkaline earth metal carbonate, in an organic or aqueous-organic medium, in the abovementioned solvents, at a temperature between −20° C. and the reflux temperature of the reaction mixture.

It is not absolutely necessary to have purified the dihalogen intermediate in order to carry out the dehydrohalogenation thereof.

The products of the general formula (XVI) in which n=0 and R$_1$ and R$_2$ are defined as above under (a'$_1$) or as in the general formula (I) under 2., except that R$_1$, R$_2$ and R$_4$ cannot represent a hydrogen atom, can be obtained by hydrolysing an enamine, or a mixture of its isomers, of the general formula:

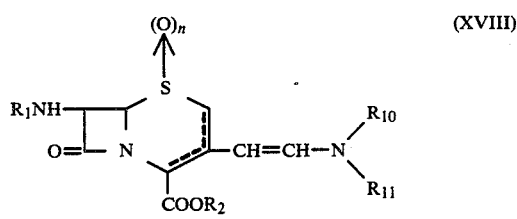

(XVIII)

[in which R$_1$ and R$_2$ are defined as above and R$_{10}$ and R$_{11}$, which are identical or different, represent alkyl radicals (optionally substituted by a hydroxyl, alkoxy, amino, alkylamino or dialkylamino radical) or phenyl radicals, or together form, with the nitrogen atom to which they are attached, a saturated heterocyclic ring of 5 or 6 ring members, optionally containing another hetero-atom chosen from amongst nitrogen, oxygen or sulphur, and optionally substituted by an alkyl radical, it being understood that the enamine of the general formula (XVIII) is in the form of a bicyclooct-2-ene or bicyclooct-3-ene, and that the substituent on the carbon atom in the 3-position of the bicyclooctene exhibits cis/trans stereoisomerism].

Preferably, an enamine of the general formula (XVIII) in which R$_{10}$ and R$_{11}$ represent a methyl radical is hydrolysed.

The reaction is generally carried out in an organic acid (e.g. formic acid or acetic acid) or a mineral acid (e.g. hydrochloric acid or sulphuric acid), in the presence or absence of a solvent, in an aqueous or organic medium, at a temperature between −20° C. and the reflux temperature of the reaction mixture, and the product is then treated, if appropriate, with an inorganic base (an alkali metal bicarbonate) or an organic base (a tertiary amine or pyridine).

If the reaction is carried out in an organic medium, the hydrolysis is carried out by adding water to the reaction medium; if the reaction is carried out in the presence of a solvent, it is not necessary for the solvent to be miscible with the acid aqueous phase; in that case, contact is effected by vigorous stirring.

Amongst the solvents which can be used, there may be mentioned chlorinated solvents, ethyl acetate, tetrahydrofuran, acetonitrile, dimethylformamide and alcohols. It is not absolutely necessary to purify the resulting product of the general formula (XVI) in order to use it for the preparation of the products of the general formula (I).

If it is desired to prepare a product of the general formula (XVI) in which R$_1$ contains a radical of the general formula (IIa), the acid group of which is free, it is necessary to use an enamine of the general formula (XVIII) in which the acid-protecting radicals R$_2$ and R$_5^c$ (in R$_1$) are different and can be removed selectively.

The removal of the protective radical $R_5{}^c$ is carried out under the conditions described above.

The products of the general formula (XVI) in which n=1 can be obtained by oxidising the products of the general formula (XVI) in which n is equal to 0, by applying the method described in German Patent Application No. 2,637,176.

The products of the general formula (XVIII) in which $R_{10}$ and $R_{11}$ are defined as above (except that they cannot represent alkyl substituted by hydroxyl, amino or alkylamino) can be obtained by reacting a product, optionally prepared in situ, of the general formula:

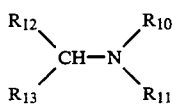
(XIX)

{in which $R_{10}$ and $R_{11}$ are defined as above and $R_{12}$ and $R_{13}$, which are identical or different, either represent groups of the general formula:

(XX)

(in which $X_2$ is an oxygen atom and $R_{14}$ represents an alkyl or phenyl radical), or represent in one case a radical of the general formula (XX) in which $X_2$ is oxygen or sulphur, and in the other case an amino radical of the general formula:

(XXI)

[in which $R_{15}$ and $R_{16}$ are defined in the same way as $R_{10}$ and $R_{11}$ in the general formula (XIX)], or also represent in each case radicals of the general formula (XXI)] with a cephalosporin derivative of the general formula:

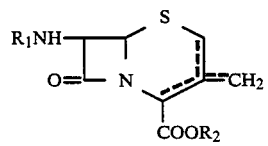
(XXII)

in which, $R_1$ and $R_2$ being defined as under (a'₁) or as under 2. for the general formula (I) (except that $R_1$, $R_2$ and $R_4$ cannot represent a hydrogen atom), the derivative is in the form of a 3-methyl-bicyclooct-2-ene or -bicyclooct-3-ene or a 3-methylenebicyclooctane.

The reaction is generally carried out in an organic solvent such as dimethylformamide, hexamethylphosphorotriamide, dimethylacetamide, acetonitrile, ethyl acetate, dioxane or a chlorinated solvent (e.g. 1,2-dichloroethane), or in a mixture of such solvents, at a temperature between 20° C. and the reflux temperature of the reaction mixture.

If a product of the general formula (XIX) in which the radical (XXI) is different from $-NR_{10}R_{11}$ is chosen, it is preferable to choose this product so that the amine $HNR_{15}R_{16}$ is more volatile than $HNR_{10}R_{11}$.

The products of the general formula (XVIII) in which $R_{10}$ and $R_{11}$, which are identical or different, represent alkyl radicals substituted by hydroxyl, amino or alkylamino can be obtained by trans-enamination from a product of the general formula (XVIII) in which $R_{10}$ and $R_{11}$ represent alkyl radicals, preferably methyl radicals.

The reaction is carried out by reacting an amine of the general formula:

(XXIII)

(in which $R_{10}$ and $R_{11}$ have the corresponding definitions) with the product of the general formula (XVIII), under conditions analogous to those described above for the reaction of a product of the general formula (XIX) with a derivative of the general formula (XXII).

The products of the general formula (XIX) can be prepared in accordance with the methods described by H. Bredereck et al., Chem. Ber. 101, 41 (1968), Chem. Ber. 101, 3,058 (1968) and Chem. Ber. 106, 3,725 (1973).

The cephalosporin derivatives of the general formula (XXII) in which $R_1$ represents a radical of the formula (II) can be prepared from the products of the general formula:

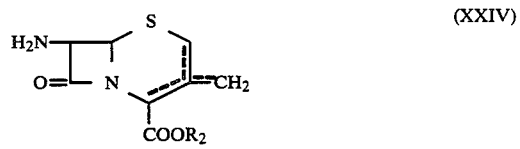
(XXIV)

[in which $R_2$ is defined as above and the position of the double bond is defined as for the product of the general formula (XXII)] by reaction with an acid of the general formula:

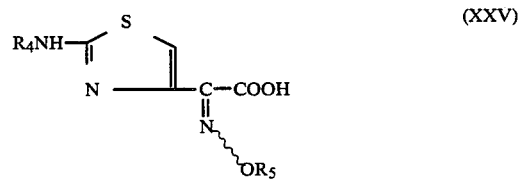
(XXV)

[in which the various symbols are defined as above, except that $R_4$ and $R_5{}^c$ (in the definition of $R_5$) cannot represent hydrogen] or with a reactive derivative of this acid. It is understood that the acid of the general formula (XXV) in the syn or anti form, or mixtures thereof, leads respectively to the products of the general formula (XXII) in the syn or anti form, or to mixtures thereof.

In general, the condensation of the acid of the general formula (XXV) with the 7-aminocephalosporin of the general formula (XXIV) is carried out in an organic solvent such as dimethylformamide, acetonitrile, tetrahydrofuran, chloroform or methylene chloride, in the presence of a condensation agent such as a carbodiimide (e.g. dicyclohexylcarbodiimide), N,N'-carbonyldiimidazole or 2-ethoxy-1-ethoxycarbonyl-1,2-dihydroquinoline, at a temperature between −20° and 40° C.

If a reactive derivative of the acid of the general formula (XXV) is used, it is possible to use the anhydride, a mixed anhydride or a reactive ester of the general formula:

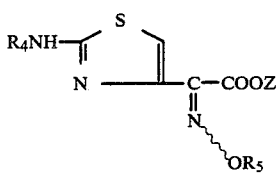

(XXVI)

[in which, the symbols $R_4$ and $R_5$ being defined as above, Z represents a succinimido, benzotriazol-1-yl, 4-nitrophenyl, 2,4-dinitrophenyl, pentachlorophenyl or phthalimido radical] or reactive derivatives such as a thiolo ester, defined below by the general formula (XLV), or an acid halide, e.g. the chloride of the acid of the general formula (XXV).

If the anhydride, a mixed anhydride or an acid halide (which can all be prepared in situ) is used, the condensation is carried out in an inert organic solvent such as an ester (e.g. tetrahydrofuran or dioxane), a chlorinated solvent (e.g. chloroform or methylene chloride), an amide (e.g. dimethylformamide or dimethylacetamide) or a ketone (e.g. acetone), or in mixtures of such solvents, in the presence of an acid acceptor such as an epoxide (e.g. propylene oxide) or such as a nitrogen-containing organic base like pyridine, dimethylaminopyridine, N-methylmorpholine or a trialkylamine (e.g. triethylamine), or in an aqueous-organic medium, in the presence of an alkaline condensation agent such as sodium bicarbonate, and the reaction is carried out at a temperature between $-40°$ and $40°$ C. It is also possible to use a cephalosporin of the general formula (XXIV) which has been silylated beforehand by applying the method described in German Patent Application No. 2,804,040.

If a reactive ester of the general formula (XXVI) or a thiolo ester is used, the reaction is generally carried out in the presence of a trialkylamine (e.g. triethylamine), in an organic solvent such as dimethylformamide, at a temperature between 0° and 40° C.

The cephalosporin derivatives of the general formulae (XXII) and (XXIV) in which $R_2$ represents a radical of the general formula (V) can be obtained by esterifying the corresponding acid by any method which is in itself known for preparing an ester from an acid without affecting the rest of the molecule.

In general, an alkali metal salt or a tertiary amine salt of a product of the general formula:

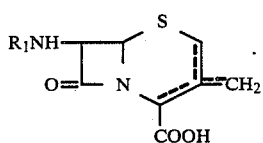

(XXVII)

[in which $R_1$ is defined as above] or

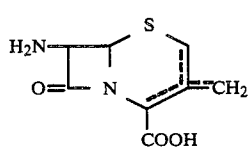

(XXVIII)

[in which formulae the position of the double bond is defined as for the products of the general formulae (XXII) and (XXIV) and, if necessary, the amine group of the radical $R_1$ is protected] is reacted with a halide of the general formula:

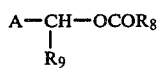

(XXIX)

in which $R_9$ and $R_{10}$ are defined as above and X represents a halogen atom, in an inert solvent such as dimethylformamide, at a temperature between 0° and 30° C.

The products of the general formula (XXIX) can be prepared in accordance with the method described in German Patent Application No. 2,350,230.

The introduction of the protective groups $R_1$ and/or $R_2$ of the products of the general formula (XXII) in which $R_1$ and $R_2$ are defined as above under 1(a) [except that $R_1$ cannot represent a radical of the general formula (II) and $R_2$ cannot represent a radical of the general formula (V)] and of the products of the general formula (XXIV) in which $R_2$ is defined as above under 1(a) [except that it cannot represent a radical of the general formula (V)] can be carried out on a cephalosporin of the general formula (XXIV), (XXVII) or (XXVIII), respectively, in accordance with one of the methods described in the following references:

if $R_1$ is a formyl radical: according to J. C. Sheehan et al., J. Amer. Chem. Soc. 80, 1,156 (1958), if $R_1$ is acetyl, chloroacetyl, trichloroacetyl, phenylacetyl, phenoxyacetyl or benzoyl: according to E. H. Flynn, Cephalosporins and Penicillins, Ac. Press (1972), if $R_1$ is a t-butoxycarbonyl radical: according to L. Moroder et al., Hoppe Seyler's Z. Physiol. Chem. 357, 1,651 (1976), if $R_1$ is 2,2,2-trichloro-1,1-dimethylethoxycarbonyl: according to J. Ugi et al., Angew. Chem. Int. Ed. Engl. 17(5), 361 (1978), if $R_1$ is 2,2,2-trichloroethoxycarbonyl, 2-chloro-1,1-dimethylethoxycarbonyl, 2-cyano-1,1-dimethylethoxycarbonyl, 2-trimethylsilylethoxycarbonyl, benzyloxycarbonyl, p-methoxybenzyloxycarbonyl, 3,5-dimethoxybenzyloxycarbonyl, p-nitrobenzyloxycarbonyl or vinyloxycarbonyl: by reaction with a chloroformate, in an aqueous-organic medium, in the presence of an alkali metal bicarbonate, or according to Belgian Pat. No. 788,885, if $R_1$ is diphenylmethoxycarbonyl: by reaction with the corresponding azidoformate, in an aqueous-organic medium, in the presence of an alkali metal bicarbonate, if $R_1$ is 2-(biphenyl-4-yl)-isopropoxycarbonyl: by analogy with the method described in Helv. Chim. Acta, 51, 924 (1968), if $R_1$ is quinol-8-yl-oxycarbonyl or allyloxycarbonyl: by reaction with the corresponding carbonate, in a basic aqueous-organic medium, if $R_1$ is o-nitrophenylthio or p-nitrophenylthio: by analogy with the method described by L. Zervas et al., J. Amer. Chem. Soc. 85, 3,660 (1963), if $R_1NH$ is replaced by dimethylaminomethyleneamino: by analogy with the method described by J. F. Fitt, J. Org. Chem. 42(15), 2,639 (1977), if $R_1NH$ is replaced by 4-nitrobenzylideneamino or 3,4-dimethoxybenzylideneamino: in accordance with the method described by R. A. Firestone, Tetrahedron Lett., 375 (1972), if $R_2$ is methoxymethyl: according to S. Seki et al., Tetrahedron Lett., 33, 2,915 (1977), if $R_2$ is t-butyl: according to R. J. Stedman, J. Med. Chem. 9, 444 (1966), if R$_2$ is benzhydryl: according to Dutch Patent Application No. 73/03,263, or if R$_2$ is nitrobenzyl, p-methoxybenzyl or benzyl according to R. R. Chauvette et al., J. Org. Chem. 38(17), 2,994 (1973).

The cephalosporin derivatives of the general formula (XXII) in which R$_1$ and R$_2$ are defined as above under 1.(b) can be prepared by acylating a 7-aminocephalosporin of the general formula (XXIV) in accordance with the methods described in U.S. Pat. No. 4,065,620.

The acids of the general formula (XXV) in which R$_5$ is hydrogen, alkyl or trityl can be prepared in accordance with the method described in Belgian Pat. No. 850,662.

The acids of the general formula (XXV) in which R$_5$ is a vinyl radical can be prepared in accordance with the method described in Belgian Pat. No. 869,079.

The acids of the general formula (XXV) in which R$_5$ is a cyanomethyl radical can be prepared in accordance with the method described in German Patent Application No. 2,812,625.

The acids of the general formula (XXV) in which R$_5$ represents a radical of the formula (IIa) can be prepared in accordance with the method described in Belgian Pat. Nos. 864,810, 865,298, 876,541 and 876,542.

The acids of the general formula (XXV) in which R$_5$ is a protective radical can be prepared by protecting the oxime of an acid of this type in which R$_5$ is hydrogen, by any known method which does not affect the rest of the molecule. The protection is effected, in particular, by means of trityl, tetrahydropyranyl or 2-methoxyprop-2-yl groups.

II. According to the invention, the products of the general formula (I) in which n is defined as above, R$_3$ is a halogen atom such as defined in the general formula (I), R$_1$ represents a hydrogen atom and R$_2$ is defined as in the general formula (I) can be obtained by removing the radical R$_1$, or, if appropriate, by simultaneously removing the radicals R$_1$ and R$_2$, of a product of the general formula (I) [in which R$_1$ is defined as in the general formula (I) under 1.(a), except that it cannot represent a radical of the general formula (II), or represents a 5-aminoadipoyl radical, the amine and acid groups of which are protected, or a radical of the general formula (VI) or (VII) such as defined for R$_1$ under 1.(b) in the general formula (I), and R$_2$ has a corresponding definition].

The removal of the protective radical R$_1$ is carried out by any known method for freeing an amine group without affecting the rest of the molecule.

The following methods may be mentioned by way of example:

if R$_1$ represents trityl, benzhydryl, trichloroacetyl, chloroacetyl, t-butoxycarbonyl, trichloroethoxycarbonyl, benzyloxycarbonyl, p-methoxybenzyloxycarbonyl or p-nitrobenzyloxycarbonyl: in accordance with the methods mentioned above for freeing the amino radical of the product of the general formula (I). In the case of a t-butoxycarbonyl radical, the reaction is advantageously carried out using p-toluenesulphonic or methanesulfonic acid in acetonitrile, at a temperature between 0° and 50° C.

if R$_1$ represents formyl, 2-chloro-1,1-dimethylethoxycarbonyl, 2-cyano-1,1-dimethylethoxycarbonyl, 3,5-dimethoxybenzyloxycarbonyl, diphenylmethoxycarbonyl, 2-(biphenyl-4-yl)-isopropoxycarbonyl, vinyloxycarbonyl, allyloxycarbonyl, quinol-8-yl-oxycarbonyl, o-nitrophenylthio or p-nitrophenylthio, or if R$_1$NH is replaced by dimethylaminomethyleneamino, 3,4-dimethoxybenzylideneamino or 4-nitrobenzylideneamino: by hydrolysis in an acid medium.

if R$_1$ represents 2,2,2-trichloroethyl or 2,2,2-trichloro-1,1-dimethylethoxycarbonyl: by treatment with zinc in acetic acid.

if R$_1$ represents acetyl, benzoyl, phenylacetyl, phenoxyacetyl or protected 5-aminoadipoyl: in accordance with the method described in Belgian Pat. No. 758,800.

if R$_1$ represents trimethylsilylethoxycarbonyl: in accordance with the method described by H. Gerlach, Helv. Chim. Acta 60 (8), 3,039 (1977).

if R$_1$ represents p-nitrobenzyloxycarbonyl: by hydrogenolysis in the presence of palladium.

III. According to the invention, the products of the general formula (I) [in which n is defined as above and R$_1$, R$_2$ and R$_3$ are defined as above under 2., or alternatively R$_1$ is a radical of the general formula (II) or a radical such as defined under 1.(b), except that it cannot represent the hydrogen atom, R$_2$ has a corresponding definition and R$_3$ is a halogen atom] can be prepared by reacting an acid represented by the general formula:

$$R_1OH \qquad (XXX)$$

in which R$_1$ is defined as above, or a reactive derivative of this acid, with a product of the general formula (I) in which R$_1$ is a hydrogen atom and R$_2$ and R$_3$ are defined as above under 1. or 2., or, if necessary, with a mixture of the isomers of this product, then, if appropriate, reducing the oxide obtained and then, if appropriate, removing the protective radicals.

The reaction is carried out by analogy with the method described above for the preparation of a product of the general formula (XXII) from products of the general formulae (XXIV) and (XXV), or in accordance with the methods mentioned in U.S. Pat. No. 4,065,620.

It is understood that the conditions of protection of R$_1$ are the same as for the reaction of the products (XXIV) with the products (XXV).

If necessary, the reduction of the oxide, and also the removal of the protective radicals of the amine group and of the acid group(s), can be carried out under the conditions described for the preparation of the product of the general formula (I) from a product of the general formula (XVI).

IV. According to the invention, the products of the general formula (I) in which n=1 can be prepared by oxidising the corresponding product of the general formula (I) in which n=0.

The oxidation can be carried out by any known method which does not affect the rest of the molecule, in particular by applying the method described in German Pat. No. 2,637,176.

V. The products of the general formula (I) [in which, n being defined as above, R$_1$ and R$_3$ are defined as above under 2., it being understood that the radical R$^c$$_5$ of the group of the general formula (IIa), contained in R$_1$, is other than the hydrogen atom, or R$_1$ is defined as under 1.(a) and R$_3$ is a halogen atom, and R$_2$ is a radical of the general formula (V)] can be obtained by esterifying the corresponding product of the general formula (I) in which R$_2$ is a hydrogen atom, by any known method for preparing an ester from an acid without affecting the rest of the molecule.

The reaction is generally carried out by reacting an alkali metal salt or a tertiary amine salt of the product of the general formula (I) with a halide of the general formula (XXIX), under the conditions described above for the preparation of products of the general formulae (XXII) or (XXIV) in which $R_2$ is a radical of the general formula (V).

VI. According to the invention, the products of the general formula (I) in which n is defined as above and $R_1$, $R_2$ and $R_3$ are defined as under 2. (except that $R_4$ cannot represent chloroacetyl or trichloroacetyl), or alternatively $R_1$ represents a radical of the general formula II defined as under 1.(a) (except that $R_4$ cannot represent chloroacetyl or trichloroacetyl and $R_5$ cannot represent vinyl), $R_2$ is as defined under 1.(a) and $R_3$ is defined as above under 1., can also be prepared by reacting a thioureau of the general formula $$R_4NH\text{—}CS\text{—}NH_2 \qquad (XXXI)$$

in which $R_4$ is defined as above, with a product or a mixture of the isomers of a product of the general formula:

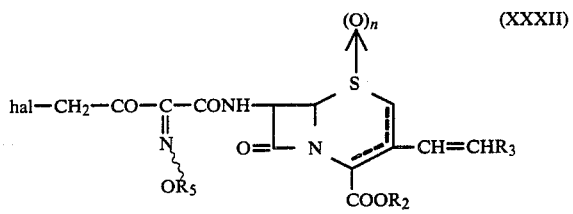

(XXXII)

in which $R_2$, $R_3$, $R_5$ and n are defined as above and hal represents a chlorine or bromine atom, and then, if appropriate, reducing the sulphoxide obtained (if n=1) and, if appropriate, removing the protective radicals.

The reaction is generally carried out in an aqueous, organic or aqueous-organic medium, e.g. in solvents or mixtures of solvents such as alcohols (methanol or ethanol), ketones (acetone), chlorinated solvents (chloroform or ethylene chloride), nitriles (acetonitrile), amides (dimethylformamide or dimethylacetamide), ethers (tetrahydrofuran or dioxane), esters (ethyl acetate) or acids (acetic acid or formic acid), in the presence or absence of a base such as sodium hydroxide, potassium hydroxide, alkali metal carbonates, alkali metal bicarbonates, alkali metal salts of carboxylic acids (sodium formate or sodium acetate) or tertiary amines (triethylamine, trimethylamine or pyridine), at a temperature between $-30°$ and $60°$ C.

If the reaction is carried out in the presence of a base, depending on the nature of the latter and the amount introduced, the intermediate of the general formula:

The products of the general formula (XXXII) in which $R_5$ is defined as above, except that it cannot represent a hydrogen atom, can be obtained by reacting an acid halide of the general formula:

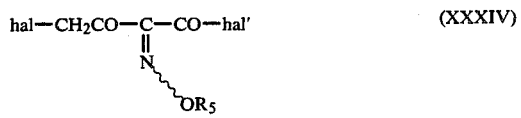

(XXXIV)

in which hal and hal' are chlorine or bromine atoms and $R_5$ is defined as above (it being understood that if $R_5$ contains an acid group, the latter is protected), with a 7-aminocephalosporin of the general formula (I) in which $R_1$ represents a hydrogen atom and $R_2$ is defined as above, and then reducing the sulphoxide obtained (if n=1) and removing the protective radicals.

The reaction is generally carried out in an aqueous-organic medium, e.g. water/ether (tetrahydrofuran or dioxane), water/ketone (acetone) or water/chlorinated solvent (chloroform or methylene chloride), in the presence of an alkaline condensation agent such as an alkali metal bicarbonate (e.g. sodium bicarbonate), at a temperature between $-40°$ and $40°$ C.

It is also possible to carry out the reaction by analogy with the method described in French Patent Application No. 2,399,418.

The products of the general formula (XXXIV) can be obtained by halogenating a product of the general formula:

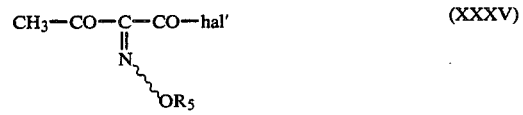

(XXXV)

in which $R_5$ and hal' are defined as above for the general formula (XXXIV), by any method which is in itself known for the preparation of halogen derivatives and which does not affect the rest of the molecule.

If it is desired to obtain a product of the general formula (XXXIV) in which hal represents a bromine atom, bromine is reacted in the presence of a catalyst, i.e. an acid catalyst such as hydrobromic acid, hydrochloric acid or sulphonic acids (methanesulphonic acid, anhydrous p-toluenesulphonic acid or benzenesulphonic acid), or in the presence of ultra-violet light.

If it is desired to obtain a product of the general formula (XXXIV) in which hal is a chlorine atom, chlorine is reacted in the presence of a catalyst such as mentioned above or sulphuryl chloride.

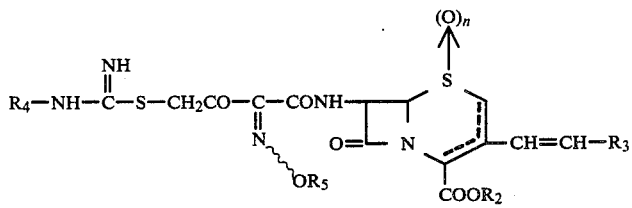

(XXXIII)

(in which $R_2$, $R_3$, $R_4$, $R_5$ and n are defined as above) may or may not be isolated, and this can then be cyclised in an acid medium.

The reduction of the sulphoxide and the removal of the protective radicals are carried out under the conditions described above.

The halogenation is carried out in an organic solvent such as a chlorinated solvent (e.g. methylene chloride, chloroform, carbon tetrachloride, dichloroethane or trichloroethane) or an ether (e.g. ethyl ether or dioxane), or in a mixture of such solvents, at a temperature between −40° C. and the reflux temperature of the reaction mixture.

The products of the general formula (XXXV) can be prepared from the corresponding acids and esters in accordance with the method described in French Patent Application No. 2,414,508.

The esters can themselves be prepared by applying the method described by R. Bucourt et al., Tetrahedron, 34, 2,233 (1978).

The acids of the general formula:

$$CH_3COC—COOH \quad (XXXVa)$$
$$\| $$
$$N$$
$$\quad OR_5$$

(in which $R_5$ is a radical $—CR^a{}_5R^b{}_5—COOR^c{}_5$ in which $R^c{}_5$ is other than a hydrogen atom) can be prepared by reacting a product of the general formula:

$$Z_3—C—COOR^c{}_5 \quad (XXXVI)$$
$$R^a{}_5 \quad R^b{}_5$$

in which $R^a{}_5$, $R^b{}_5$ and $R^c{}_5$ are defined as above, except that $R^c{}_5$ cannot represent a hydrogen atom, and $Z_3$ represents a halogen atom or a sulphate or sulphonate radical, with a product of the general formula:

$$CH_3COC—COOR'_2 \quad (XXXVb)$$
$$\|$$
$$N$$
$$\quad OH$$

in which $R'_2$ is an acid-protecting radical such as defined above for $R_2$, and then removing the protective radical $R'_2$.

The reaction is generally carried out in the presence of an inorganic or organic base (e.g. sodium hydroxide, potassium hydroxide, sodium hydride, potassium carbonate or a nitrogen-containing base such as triethylamine), in an organic solvent such as a chlorinated solvent (e.g. methylene chloride or dichloroethane), an ether (e.g. tetrahydrofuran or dioxane), a ketone (e.g. acetone) or an amide (e.g. dimethylformamide).

It is necessary for the acid-protecting radicals ($R'_2$ and $R^c{}_5$) to be different and to be removable selectively.

The removal of the protective radical $R'_2$ is carried out under the conditions described above.

The products of the general formula (XXXII) in which $R_5$ is a hydrogen atom can be obtained by introducing a nitroso group into a product of the general formula:

$$hal—CH_2—CO—CH_2—CONH—\begin{array}{c}(O)_n\\ \uparrow\\ S\end{array}\quad (XXXVII)$$
$$O= N \quad CH=CH—R_3$$
$$COOR_2$$

in which $R_2$, $R_3$, hal and n are defined as above, by analogy with the method described in French Patent Application No. 2,399,418, and then, if appropriate, reducing the sulphoxide and removing the protective radicals.

The products of the general formula (XXXII) in which $R_5$ is a protective radical can be obtained by protecting the oxime of a product of the general formula (XXXII) in which $R_5$ is a hydrogen time.

The products of the general formula (XXXVII) can be obtained from a 7-aminocephalosporin of the general formula (I) in which $R_2$ is defined as above and $R_1$ represents a hydrogen atom, by reaction with a product (which can be formed in situ) of the general formula:

$$hal—CH_2—CO—CH_2—CO—hal \quad (XXXIVa)$$

in which hal is defined as above, under the conditions described above for the condensation of a product of the general formula (XXXIV) with a product of the general formula (I), or by analogy with the method described in French Patent Application No. 2,399,418.

The new products of the general formula (I) are useful as intermediates for the preparation of 3-thiovinyl-cephalosporins of the general formula:

$$R^o{}_1NH—\begin{array}{c}S\\ \end{array}\quad (XXXVIII)$$
$$O= N \quad CH=CH—SR$$
$$COOR^o{}_2$$

in which:

$a_1$. the symbol R is chosen from amongst:

(1) alkyl, L-2-amino-2-carboxyethyl or phenyl, (2) optionally N-oxidised pyrid-2-yl, pyrid-3-yl or pyrid 4-yl, (3) pyrimidin-2-yl, pyridazin-3-yl substituted in the 6-position (by an alkyl, methoxy, amino or acylamino radical) and optionally N-oxidised, or tetrazolo[4,5-b]pyridazin-6-yl, (4) 5,6-dioxo-1,4,5,6-tetrahydro-1,2,4-triazin-3-yl substituted in the 4-position, or 1,3,4-triazol-5-yl or 2-alkoxycarbonyl-1,3,4-triazol-5-yl substituted in the 1-position, by (a) an alkyl radical containing 1 to 4 carbon atoms, which is unsubstituted or substituted by an alkoxy, alkylthio, phenyl, formyl, carbamoyl, alkylcarbamoyl, dialkylcarbamoyl, acyl, alkoxycarbonyl or thiazolidin-2-yl radical, (b) an allyl, 2,3-dihydroxypropyl, 1,3-dihydroxyprop-2-yl, 2-formyl-2-hydroxyethyl, 3-formyloxy-2-hydroxypropyl, 2,3-bis-formyloxypropyl or 1,3-bis-formyloxy-prop-2-yl radical, (c) an alkyl radical containing 2 to 4 carbon atoms, which is substituted by hydroxyl or carbamoyloxy, acyloxy (the acyl part of which can be substituted by an amino, alkylamino or dialkylamino radical), alkylsulphinyl, alkylsulphonyl, amino, alkylamino, dialkylamino, sulphonamino, alkylsulphonylamino or sulphamoylamino, acylamino (the acyl part of which is optionally substituted by hydroxyl, amino, alkylamino or dialkylamino) or alkoxycarbonylamino, ureido, alkylureido or dialkylureido, (d) radical corresponding to one of the general formulae:

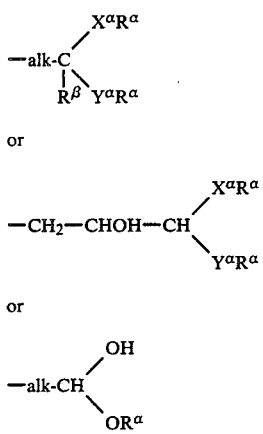

in which alk is an alkylene radical containing 1 to 4 carbon atoms, $X^\alpha$ and $Y^\alpha$ are identical and represent oxygen or sulphur atoms and $R^\alpha$ represents an alkyl radical, or alternatively $X^\alpha$ and $Y^\alpha$ are identical or different and represent oxygen or sulphur atoms and the radicals $R^\alpha$ together form an alkylene radical containing 2 or 3 carbon atoms, and $R^\beta$ represents a hydrogen atom or an alkyl radical containing 1 to 3 carbon atoms, or (e) an alkyl radical containing 1 to 5 carbon atoms, which is substituted by an alkoxyamino or hydroxyimino radical, (5) 1,4-dialkyl-5,6-dioxo-1,4,5,6-tetrahydro-1,2,4-triazin-3-yl, 1-alkyl-5,6-dioxo-1,4,5,6-tetrahydro-1,2,4-triazin-3-yl or 2-alkyl-5,6-dioxo-1,2,5,6-tetrahydro-1,2,4-triazin-3-yl, (6) 1,3,4-triazol-5-yl, 1,2,3-triazol-5-yl or 1-alkyl-1,2,4-triazol-5-yl which is unsubstituted in the 3-position by alkoxycarbonyl, (7)
(a) 1,3,4-thiadiazol-5-yl which is unsubstituted or substituted by an alkyl, trifluoromethyl, alkoxy or alkylthio radical, a hydroxyalkylthio radical, the alkyl part of which contains 2 to 4 carbon atoms, or an alkylsulphonyl, hydroxyl, hydroxyalkyl, carboxyl, carboxyalkyl, amino, alkylamino, dialkylamino, aminoalkyl, alkylaminoalkyl, dialkylaminoalkyl, acylamino or acylaminoalkyl radical, or
(b) 1,2,4-thiadiazol-5-yl substituted by an alkyl or alkoxy radical, (8)
(a) 1,3,4-oxadiazol-5-yl which is unsubstituted or substituted by an alkyl, trifluoromethyl, phenyl, aminoalkyl, alkylaminoalkyl, dialkylaminoalkyl or acylaminoalkyl radical, or
(b) oxazol-2-yl or 4-alkyloxazol-2-yl, (9) tetrazol-5-yl which is unsubstituted or substituted in the 1-position by (a) an alkyl radical containing 1 to 4 carbon atoms, which is unsubstituted or substituted by alkoxy, sulpho, carboxyl, formyl or sulphamoyl, (b) an alkyl radical containing 2 to 4 carbon atoms which is substituted by hydroxyl, amino, alkylamino, dialkylamino, acylamino, carboxyalkylamino, sulphamoylamino, sulphoamino, ureido, alkylureido or dialkylureido, (c) an alkyl radical containing 1 to 5 carbon atoms, which is substituted by hydroxyimino or alkoxyimino, (d) a phenyl, 2,3-dihydroxypropyl, 1,3-dihydroxyprop-2-yl, 2-formyl-2-hydroxyethyl, 3-formyloxy-2-hydroxypropyl, 2,3-bis-formyloxypropyl or 1,3-bis-formyloxyprop-2-yl radical, or (e) a radical of the general formula (XXXIXa) in which $R^\beta$ is a hydrogen atom, or a radical of the general formula (XXXIXb),

(10) 5,6-dioxo-1,4,5,6-tetrahydro-1,2,4-triazin-3-yl substituted in the 1-position, 5,6-dioxo-1,2,5,6-tetrahydro-1,2,4-triazin-3-yl substituted in the 2-position, or 1,2,4-triazol-5-yl or 3-alkoxycarbonyl-1,2,4-triazol-5-yl substituted in the 1-position, by (a) an alkyl radical substituted by an alkoxy, alkylthio, phenyl, formyl, carbamoyl, alkylcarbamoyl or dialkylcarbamoyl radical, by a hydroxyalkylcarbamoyl radical (the alkyl part of which contains 2 to 4 carbon atoms) or by an acyl, alkoxycarbonyl or thiazolidin-2-yl radical, (b) an allyl, 2,3-dihydroxypropyl, 1,3-dihydroxyprop-2-yl, 2-formyl-2-hydroxyethyl, 3-formyloxy-2-hydroxypropyl, 2,3-bis-formyloxypropyl or 1,3-bis-formyloxyprop-2-yl radical, (c) an alkyl radical containing 2 to 4 carbon atoms, which is substituted by hydroxyl, carbamoyloxy, acyloxy (the acyl part of which can be substituted by an amino, alkylamino or dialkylamino radical), alkylsulphinyl, alkylsulphonyl, amino, alkylamino, dialkylamino, sulphoamino, alkylsulphonylamino or sulphamoylamino, acylamino (the acyl part of which is optionally substituted by hydroxyl, amino, alkylamino or dialkylamino), alkoxycarbonylamino, ureido, alkylureido or dialkylureido, (d) a radical corresponding to one of the general formulae (XXXIXa), (XXXIXb) or (XXXIXc) such as defined above, or (e) an alkyl radical containing 2 to 5 carbon atoms, which is substituted by an alkoxyimino or hydroxyimino radical,

(11) 5,6-dioxo-4-hydroxyalkylcarbamoylalkyl-1,4,5,6-tetrahydro-1,2,4-triazin-3-yl, the hydroxyalkyl portion of which contains 2 to 4 carbon atoms, and

(12) 1-alkyl-5,6-dioxo-1,4,5,6-tetrahydro-1,2,4-triazin-3-yl substituted in the 4-position, 1-alkyl-5,6-dioxo-1,2,5,6-tetrahydro-1,2,4-triazin-3-yl substituted in the 2-position, 2-alkyl-5,6-dioxo-1,2,5,6-tetrahydro-1,2,4-triazin-3-yl substituted in the 1-position, or 4-alkyl-5,6-dioxo-1,4,5,6-tetrahydro-1,2,4-triazin-3-yl substituted in the 1-position, by a formylalkyl radical or by a radical of the general formula (XXXIXa) in which $R^\beta$ is a hydrogen atom, the symbol $R°_1$ represents a radical of the general formula (II) [in which $R_5$ is hydrogen, alkyl, vinyl, cyanomethyl or a radical of the general formula (IIa), $R_5{}^a$ and $R^b{}_5$ are defined as above and $R^c{}_5$ and $R_4$ are hydrogen atoms] and the symbol $R°_2$ represents a hydrogen atom or a radical of the general formula (V), or alternatively $\beta_1$. the symbol R represents an alkyl or phenyl radical, the symbol $R°_1$ is defined in the same way as $R_1$ above under 1.(b) and the symbol $R°_2$ is defined in the same way and $R_2$ above under 1.(b).

It is understood that, in the products of the general formula (XXXVIII), the substituent in the 3-position of the bicyclooctene exhibits E/Z stereoisomerism and, if $R°_1$ is a radical of the general formula (II), it can be in the syn or anti form. The products of the general formula (XXXVIII) also exist as mixtures of these isomeric forms.

The products of the general formula (XXXVIII) can be obtained from the products of the general formula (I) by the following procedure:

(I) The 3-thiovinylcephalosporins of the general formula (XXXVIII) in which R is defined as under $\alpha_1$. and $\beta_1$., except that it cannot contain a substituent of the general formula (XXXIXc), can be prepared by reacting a thiol (or one of its alkali metal or alkaline earth metal salts) of the general formula:

R—SH         (XL)

[in which the radical R, which is defined as above, is protected in the form of an acetal such as defined by the general formulae (XXXIXa) and (XXXIXb), if it is desired to obtain a cephalosporin of the general formula (XXXVIII) in which R contains a formyl or acylalkyl radical] with a cephalosporin derivative or a mixture of the isomers of the general formula (I) [in which $R_1$ is a radical of the general formula (II) such as defined above under 1.(a) or 2. and $R_2$ has a corresponding definition, or $R_1$ is defined as above under 1.(b) and $R_2$ has a corresponding definition], and then, if appropriate, reducing the oxide obtained and removing the protective radicals.

It is understood that if the radical R of the product of the general formula (XL) contains a group capable of interfering with the reaction, it is preferable to protect this group by any method which is in itself known and which does not affect the rest of the molecule (in particular if R contains an amino, alkylamino, hydroxyl or carboxyl radical).

In the case of the amino, alkylamino or carboxyl groups, the protection is effected under the condition described above.

In the case of hydroxyl groups, the protection is effected by means of the radicals mentioned above for the protection of the oxime, or in the form of a cyclic acetal for the protection of the 2,3-dihydroxypropyl or 1,3-dihydroxyprop-2-yl radicals (e.g. in the form of 2,2-dimethyldioxan-4-yl-methyl or 2,2-dimethyldioxan-5-yl radicals).

It is also understood that if $R_5$ represents a hydrogen atom, it is preferable to protect the oxime (under the conditions described above). It is also preferable to use a cephalosporin in which the radical $R^c_5$ of the group (IIa) is an acid-protecting radical.

Furthermore, it is understood that if the radical R of the product of the general formula (XL) contains a hydroxyl or sulpho radical, it is preferable to use a product of the general formula (I) in which n=0.

The reaction is generally carried out in the presence of a base such as a pyridine or a tertiary organic base of the general formula (XVII).

The tertiary organic base used is e.g. diisopropylethylamine or diethylphenylamine.

The presence of a base of this type is not necessary if the reaction is carried out using an alkali metal or alkaline earth metal salt of the thiol of the general formula (XL).

The reaction is advantageously carried out in an organic solvent such as dimethylformamide, tetrahydrofuran, methanol, ethanol or acetonitrile, or a mixture of such solvents.

It is also possible to carry out the reaction in the presence of an alkali metal bicarbonate, in a solvent such as mentioned above, if appropriate in the presence of water.

The reaction is carried out at a temperature between −20° C. and the reflux temperature of the reaction mixture, the chosen temperature varying according to the thiol employed. Likewise, the reaction time can vary from 5 minutes to 48 hours, depending on the thiol employed.

If appropriate, the reaction is carried out under nitrogen.

Preferably, if it is desired to use a bicyclooct-3-ene of the general formula (I) in which $R_1$ represents a radical of the general formula (II) a product of this type in which $R_2$ is other than hydrogen is used.

It is of no consequence whether the removal of the protective radical of R is carried out before or after the reduction of the oxide, before, simultaneously with or after the removal of the other protective radicals.

The reduction of the oxide and the removal of the protective groups are carried out in accordance with the methods described above.

If the dihydroxypropyl radicals are protected in the form of cyclic acetals, the removal of the protective radicals is carried out by acidolysis (trifluoroacetic acid, aqueous or non-aqueous formic acid or p-toluenesulphonic acid).

If aqueous or non-aqueous formic acid is used, the freeing of the hydroxyl radicals protected in the form of a cyclic acetal can lead at least partially to the corresponding formic acid monoesters or diesters, which can be separated off, necessary, by chromatography.

The freeing of the formulalkyl or acylalkyl radicals protected in the form of groups of the general formulae (XXXIXa) and (XXXIXb) (if it is desired to obtain a product of the general formula (XXXVIII) in which R contains a formyl or acylalkyl radical) is carried out:

in the presence of a sulphonic acid (e.g. methanesulphonic acid or p-toluenesulphonic acid), in an organic solvent (e.g. acetonitrile or acetone), if appropriate in the presence of water and if appropriate in the presence of a reagent which can be converted to an acetal, such as acetone, glyoxylic acid, benzaldehyde or pyruvic acid, at a temperature between 20° C. and the reflux temperature of the reaction mixture, or alternatively, if the radical R is a 5,6-dioxo-1,4,5,6-tetrahydro-1,2,4-triazin-3-yl radical, by reaction with pure or aqueous formic acid (preferably containing less than 10% of water), either in the presence or absence of silica, or by trans-acetalisation in the presence of a reactant which can be converted to an acetal, such as defined above.

The thiols of the general formula (XL) (which can be used in their tautomeric form) can be prepared by applying one of the following methods, depending on the meaning of the radical R:

if R is a pyrid-3-yl radical: in accordance with the method described by H. M. Wuest and E. H. Sakal, J. Amer. Chem. Soc., 73, 1,210 (1951), if R is a pyrid-3-yl-1-oxide radical: in accordance with the method described by B. Blank et al., J. Med. Chem. 17, 1,065 (1974), if R is a pyrid-4-yl-1-oxide radical: in accordance with the method described by R. A. Y. Jones et al., J. Chem. Soc. 2,937 (1960), if R is a pyridazin-3-yl radical substituted by alkyl or methoxy and optionally N-oxidised: in accordance with the method described in Belgian Pat. No. 787,635, if R is a pyridazin-3-yl radical substituted by amino and optionally N-oxidised: in accordance with the method described in Belgian Pat. No. 579,291, if R is a pyridazin-3-yl radical substituted by acylamino and optionally N-oxidised: by applying the methods described by M. Kumagai and M. Bando, Nippon Kagaku Zasshi, 84, 995 (1963), and by T. Horie and T. Ueda, Chem. Pharm. Bull., 11, 114 (1963), if R is a tetrazolo[4,5-b]pyridazin-6-yl radical: in accordance with the method described in Belgian Pat. No. 804,251, if R is a 5,6-dioxo-1,4,5,6-tetrahydro-1,2,4-triazin-3-yl radical substituted in the 4-position, or a 2-alkoxycarbonyl-1,3,4-triazol-5-yl radical substituted in the 1-position, by a radical $R^\gamma$ chosen from amongst:

(a) an allyl radical, an alkyl radical (containing 1 to 4 carbon atoms, which is itself optionally substituted by an alkoxy, alkylthio, phenyl, carbamoyl, alkylcarbamoyl, dialkylcarbamoyl, acyl, alkoxycarbonyl or thiazolidin-2-yl radical), (b) a 2,3-dihydroxypropyl or 1,3-dihydroxyprop-2-yl radical (optionally protected in the form of a cyclic acetal), (c) an alkyl radical [containing 2 to 4 carbon atoms, which is itself substituted by hydroxyl, carbamoyloxy, dialkylamino, alkylsulphinyl, alkylsulphonyl, alkylsulphonylamino, sulphamoylamino, acylamino (optionally substituted), alkoxycarbonylamino, ureido, alkylureido or dialkylureido], (d) a radical of the general formula (XXXIXa) or (XXXIXb), or (e) a hydroxyiminoalkyl or alkoxyiminoalkyl radical, or if R is a 5,6-dioxo-1,4,5,6-tetrahydro-1,2,4-triazin-3-yl radical substituted in the 1-position, a 5,6-dioxo-1,2,5,6-tetrahydro-1,2,4-triazin-3-yl radical substituted in the 2-position, or a 3-alkoxycarbonyl-1,2,4-triazol-5-yl radical substituted in the 1-position, by a radical $R^\gamma$ such as defined above (except that it cannot represent an unsubstituted alkyl radical) or by a hydroxyalkylcarbamoylalkyl radical, the hydroxyalkyl portion of which contains 2 to 4 carbon atoms, or if R is a 5,6-dioxo-4-hydroxyalkylcarbamoylalkyl-1,4,5,6-tetrahydro-1,2,4-triazin-3-yl radical, the hydroxyalkyl portion of which contains 2 to 4 carbon atoms: by reacting an alkyl oxalate or an alkyl monooxalate halide with a thiosemicarbazide of the general formula:

  (XLIa)

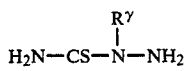  (XLIb)

or

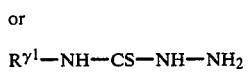  (XLIc)

(in which formulae $R^\gamma$ is defined as above and $R^{\gamma 1}$ represents a hydroxyalkylcarbamoylalkyl radical or a radical $R^\gamma$).

The reaction is carried out in the presence of an alkali metal alcoholate, e.g. sodium ethylate or methylate or potassium t-butylate, by applying the method described by M. Pesson and M. Antoine, Bull. Soc. Chim. France 1,590 (1970).

It is not absolutely necessary to purify the product obtained (or to free the protected radicals) in order to use it for the preparation of the products of the general formula (XXXVIII).

The thiosemicarbazides of the general formulae (XLIa) to (XLIc) can be prepared in accordance with one of the methods described by K. A. Jensen et al., Acta Chem. Scand., 22, 1 (1968), or by applying the method described by Y. Kazakov and J. Y. Potovskii, Doklady Acad. Nauk. SSSR 134, 824 (1960), it being understood that if $R^\gamma$ contains an amino radical, the letter is protected.

The protection of the amino radical and the removal of the protective radical are carried out in accordance with the usual methods which do not affect the rest of the molecule. The t-butoxycarbonyl group, which can be removed by acid hydrolysis, is used in particular.

If R is a 1,3,4-triazol-5-yl radical substituted in the 1-position by:

an alkyl, allyl or alkoxyalkyl radical, an alkyl radical (1 to 4 carbon atoms) which is itself substituted as defined above under (a), except that it cannot be substituted by a thiazolidin-2-yl radical.

a radical such as defined above under (c), or an alkoxyiminoalkyl radical:

by applying one of the methods described by M. Pesson and M. Antoine, Bull. Soc. Chim. France 1,590 (1970).

If R is a 1,3,4-triazol-5-yl radical substituted in the 1-position by thiazolidin-2-yl-alkyl or hydroxyiminoalkyl: by reacting respectively cysteamine or hydroxylamine with a 1-dialkoxyalkyl-5-mercapto-1,3,4-triazole which can be obtained, by applying the method described by M. Kanaoka, J. Pharm. Soc. Japan, 75, 1,149 (1955), from a 4-dialkoxyalkylthiosemicarbazide.

If R is a 1,3,4-triazol-5-yl radical substituted in the 1-position by 2,3-dihydroxypropyl or 1,3-dihydroxyprop-2-yl (which are optionally protected in the form of a cyclic acetal), or represents a radical of the general formula (XXXIXa) or (XXXIXb): by applying the method described by M. Kanaoka, J. Pharm. Soc. Japan, 75, 1,149 (1955).

If R is a 5,6-dioxo-1,4,5,6-tetrahydro-1,2,4-triazin-3-yl radical substituted in the 4-position, or a 2-alkoxycarbonyl-1,3,4-triazol-5-yl or 1,3,4-triazol-5-yl radical substituted in the 1-position, by acyloxyalkyl (optionally substituted): by respectively acylating 5,6-dioxo-4-hydroxyalkyl-3-mercapto-1,4,5,6-tetrahydro-1,2,4-triazine, 2-alkoxycarbonyl-1-hydroxyalkyl-5-mercapto-1,3,4-triazole or 1-hydroxyalkyl-5-mercapto-1,3,4-triazole, the mercapto radical of which has been protected beforehand [e.g. according to C. G. Kruse et al., Tet. Lett. 1,725 (1976)], by any known method for acylating an alcohol without affecting the rest of the molecule, and then freeing the mercapto group in an acid medium.

If R is a 5,6-dioxo-1,4,5,6-tetrahydro-1,2,4-triazin-3-yl radical substituted in the 4-position, or a 2-alkoxycarbonyl-1,3,4-triazol-5-yl or 1,3,4-triazol-5-yl radical substituted in the 1-position, by aminoalkyl or alkylaminoalkyl: by freeing the amine group of the corresponding product, which amine group is protected e.g. by a t-butoxycarbonyl group.

If R is a 5,6-dioxo-1,4,5,6-tetrahydro-1,2,4-triazin-3-yl radical substituted in the 4-position, or a 2-alkoxycarbonyl-1,3,4-triazol-5-yl or 1,3,4-triazol-5-yl radical substituted in the 1-position, by sulphoaminoalkyl: from the corresponding product substituted by a t-butyoxycarbonylaminoalkyl radical, by analogy with the method described in Belgian Pat. No. 847,237.

If R is a 1,4-dialkyl-5,6-dioxo-1,4,5,6-tetrahydro-1,2,4-triazin-3-yl or 1-alkyl-5,6-dioxo-1,4,5,6-tetrahydro-1,2,4-triazin-3-yl radical: in accordance with the method described in Belgian Pat. No. 830,455.

If R is a 2-alkyl-5,6-dioxo-1,2,5,6-tetrahydro-1,2,4-triazin-3-yl or 1-alkyl-3-alkoxycarbonyl-1,2,4-triazol-5-yl radical: in accordance with the method described by M. Pesson and M. Antoine, C.R. Acad. Sci., Ser C, 267, 25, 1,726 (1968).

If R is a 1,2,3-triazol-5-yl radical: in accordance with the method described in French patent application No. 2,215,942.

If R is a 1,3,4-triazol-5-yl radical: in accordance with the method described by M. Kanaoka, J. Pharm. Soc. Jap. 75, 1,149 (1955).

If R is a 1,3,4-thiadiazol-5-yl radical optionally substituted by alkyl, alkoxy, alkylthio, alkylsulphonyl, amino, alkylamino, dialkylamino or acylamino: in accordance with the methods described in Belgian Pat. No. 830,821.

If R is a 1,3,4-thiadiazol-5-yl radical substituted by hydroxyalkyl, aminoalkyl, alkylaminoalkyl or dialkylaminoalkyl: in accordance with the method described in German patent application No. 2,446,254.

If R is a 1,3,4-thiadiazol-5-yl radical substituted by a carboxyalkyl radical: by applying the method described in German patent application No. 1,953,861.

If R is a 1,3,4-thiadiazol-5-yl radical substituted by a trifluoromethyl radical: in accordance with the method described in German patent application No. 2,162,575.

If R is a 1,3,4-thiadiazol-5-yl radical substituted by a carboxyl radical: in accordance with the method described in Japanese patent application No. 77/48,666.

If R is a 1,3,4-thiadiazol-5-yl radical substituted by an acylaminoalkyl radical: in accordance with the method described in Japanese patent application No. 76/80,857.

If R is a 1,3,4-thiadiazol-5-yl radical substituted by a hydroxyalkylthio radical: by applying the method described by G. Nannini, Arz. Forsch. 27 (2), 343 (1977).

If R is a 1,2,4-thiadiazol-5-yl radical substituted by alkyl or alkoxy: in accordance with the method described in German patent application No. 2,806,226 or according to Chem. Ber. 90, 184 (1957).

If R is a 1,3,4-oxadiazol-5-yradical such as defined above under 8(a): by applying the method described by E. Hoggarth, J. Chem. Soc. 4,811 (1952).

If R is an oxazol-2-yl or 4-alkyloxazol-2-yl. radical: by applying the method previously described by C. Bradsher, J. Org. Chem. 32, 2,079 (1967).

If R is a tetrazol-5-yl radical optionally substituted in the 1-position by alkyl, hydroxyalkyl or phenyl: in accordance with the methods described in Belgian Pat. No. 830,821.

If R is a tetrazol-5-yl radical substituted in the 1-position by alkoxyalkyl: by adding sodium azide to an isothiocyanatoalkoxyalkyl compound, the reaction being carried out in an organic solvent such as ethanol, at the reflux temperature of the reaction mixture.

The isothiocyanatoalkoxyalkyl compound can be obtained by applying the method described by E. Schmidt et al., Chem. Ber. 73,286 (1940).

If R is a tetrazol-5-yl radical substituted in the 1-position by a carboxyalkyl radical: in accordance with the method described in Belgian Pat. No. 858,112.

If R is a tetrazol-5-yl radical substituted in the 1-position by a sulphoalkyl radical: in accordance with the method described in Belgian Pat. No. 856,498 or described by D. A. Berges et al., J. Het. Chem. 15, 981 (1978).

If R is a tetrazol-5-yl radical substituted in the 1-position by an aminoalkyl, alkylaminoalkyl or dialkylaminoalkyl radical: by applying the method described in German patent application No. 2,738,711.

If R is a tetrazol-5-yl radical substituted in the 1-position by a sulphamoylalkyl, sulphamoylaminoalkyl,or sulphoaminoalkyl radical: in accordance with the method described in Belgian Pat. No. 856,636.

If R is a tetrazol-5-yl radical substituted by an acylaminoalkyl radical, or a 1,3,4-thiadiazol-5-yl radical substituted by hydroxyl: in accordance with the method described in U.S. Pat. No. 4,117,123.

If R is a tetrazol-5-yl radical substituted in the 1-position by a ureidoalkyl, alkylureidoalkyl or dialkylureidoalkyl radical: from the corresponding product substituted by aminoalkyl (the mercapto radical of which has been protected beforehand), by treatment with an alkali metal isocyanate, with an alkyl isocyanate or with a dialkylcarbamoyl halide, and then freeing of the mercapto group under the conditions described in Belgian Pat. No. 847,237.

If R is a tetrazol-5-yl radical substituted in the 1-position by a carboxyalkylaminoalkyl radical: in accordance with the method described in German patent application No. 2,715,597.

If R is a tetrazol-5-yl radical substituted in the 1-position by a 2,3-dihydroxypropyl radical: in accordance with the method described in U.S. Pat. No. 4,064,242.

If R is a tetrazol-5-yl radical substituted in the 1-position by a 1,3-dihydroxyprop-2-yl radical: by adding sodium azide to a 2,2-dimethyl-1,3-dioxolan-5-yl isothiocyanate (and then freeing the hydroxyl groups, if appropriate).

If R is a tetrazol-5-yl radical substituted in the 1-position by a radical of the general formula (XXXIXa) or (XXXIXb) such as defined as above under 9(e), or a radical defined above under 9(c): by reacting sodium azide with the corresponding isothiocyanate, by analogy with the method described by R. E. Orth, J. Pharm. Sci. 52 (9), 909 (1963), it being understood that, in the case where R contains a hydroxyl or hydroxyiminoalkyl substitient, the alcohol or the oxime are optionally protected, e.g. by a tetrahydropyranyl group.

If R is a 1,2,4-triazol-5-yl radical substituted in the 1-position by:
an allyl or alkoxyalkyl radical,
an alkyl radical (1 to 4 carbon atoms) which is itself substituted as defined above under (a), except that it cannot be substituted by a thiazolidin-2-yl radical,
a hydroxyalkylcarbamoylalkyl radical, the hydroxyalkyl part of which contains 2 to 4 carbon atoms,
a radical such as defined above under (c), or
an alkoxyiminoalkyl radical:
by analogy with the methods described by M. Pesson and M. Antoine, Bull. Soc. Chim. France, 1,599 (1970), or C.R. Acad. Sci., Ser. C, 267, (25), 1,726 (1968).

If R is a 1,2,4-triazol-5-yl radical substituted in the 1-position by thiazolidin-2-yl-alkyl or by hydroxyiminoalkyl: by reacting respectively cysteamine or hydroxylamine with a 1-dialkoxyalkyl-5-mercapto-1,2,4-triazole which can be obtained, by analogy with the method described by M. Kanaoka, J. Pharm. Soc. Japan, 75, 1,149 (1955), from a 4-dialkoxyalkylthiosemicarbazide.

If R is a 1,2,4-triazol-5-yl radical substituted in the 1-position by 2,3-dihydroxypropyl or 1,3-dihydroxyprop-2-yl (which are optionally protected in the form of a cyclic acetal) or by a radical of the general formula (XXXIXa) or (XXXIXb): by analogy with the method described by M. Kanaoka, J. Pharm. Soc. Japan, 75, 1,149 (1955).

If R is a 5,6-dioxo-1,4,5,6-tetrahydro-1,2,4-triazin-3-yl radical substituted in the 1-position, a 5,6-dioxo-1,2,5,6-tetrahydro-1,2,4-triazin-3-yl radical substituted in the 2-position, or a 3-alkoxycarbonyl-1,2,4-triazol-5-yl or 1,2,4-triazol-5-yl radical substituted in the 1-position, by acyloxyalkyl (optionally substituted): by respectively acylating 5,6-dioxo-1-hydroxyalkyl-3-mercapto-1,4,5,6-tetrahydro-1,2,4-triazine, 5,6-dioxo-2-hydroxyalkyl-3-mercapto-1,2,5,6-tetrahydro-1,2,4-triazine, 3-alkoxycarbonyl-1-hydroxyalkyl-5-mercapto-1,2,4-triazole or 1-hydroxyalkyl-5-mercapto-1,2,4-triazole, the mercapto radical of which has been protected beforehand [e.g. according to C. G. Kruse et al., Tet. Lett. 1,725 (1976)], by any method known for acylating an alcohol without affecting the rest of the molecule, and then freeing the mercapto group in an acid medium.

If R is a 5,6-dioxo-1,4,5,6-tetrahydro-1,2,4-triazin-3-yl radical substituted in the 1-position, a 5,6-dioxo-1,2,5,6-tetrahydro-1,2,4-triazin-3-yl radical substituted in the 2-position, or a 3-alkoxycarbonyl-1,2,4-triazol-5-yl or 1,2,4-triazol-5-yl radical substituted in the 1-position, by aminoalkyl or alkylaminoalkyl: by freeing the amine group of the corresponding product, which amine group is protected e.g. by a t-butoxycarbonyl group.

If R is a 5,6-dioxo-1,4,5,6-tetrahydro-1,2,4-triazin-3-yl radical substituted in the 1-position, a 5,6-dioxo-1,2,5,6-tetrahydro-1,2,4-triazin-3-yl radical substituted in the 2-position, or a 3-alkoxycarbonyl-1,2,4-triazol-5-yl or 1,2,4-triazol-5-yl radical substituted in the 1-position, by sulphoaminoalkyl: from the corresponding product substituted e.g. by a t-butoxycarbonylaminoalkyl radical, by analogy with the method described in Belgian Pat. No. 847,237.

If R is a 1-alkyl-5,6-dioxo-1,4,5,6-tetrahydro-1,2,4-triazin-3-yl radical substituted in the 4-position, a 1-alkyl-5,6-dioxo-1,2,5,6-tetrahydro-1,2,4-triazin-3-yl radical substituted in the 2-position, a 2-alkyl-5,6-dioxo-1,2,5,6-tetrahydro-1,2,4-triazin-3-yl radical substituted in the 1-position, or a 4-alkyl-5,6-dioxo-1,4,5,6-tetrahydro-1,2,4-triazin-3-yl radical substituted in the 1-position, by a formylalkyl radical or by a radical of the general formula (XXXIXa) in which $R^\beta$ represents a hydrogen atom: by reacting an alkyl oxalate with a thiosemicarbazide, by analogy with the method described by M. Pesson and M. Antoine, C.R. Acad. Sci. 267 (25C), 904 (1968) or C.R. Acad. Sci. 267 (25C), 1,726 (1968).

(II) The 3-thiovinylcephalosporins of the general formula (XXXVIII) in which R does not contain a substituent of the general formula (XXXIXc) can also be obtained in the following manner:

A thiol of the general formula (XL) (or one of its alkali metal or alkaline earth metal salts), such as defined above, is reacted with a product of a mixture of isomers of the product of the general formula (I) in which $R_1$ is as defined in general formula (I) under 1.(a) with the exception of representing a radical of the general formula (II), or a 5-amino-adipoyl radical in which the amine and acid functions are protected, or a radical of general formula (VI) or (VII) as defined under 1.(b), and $R_2$ has a corresponding definition, and then, if appropriate, the sulphoxide obtained is reduced (if n=1), and, if appropriate, the protective radicals of R are removed in order to prepare a product of the general formula:

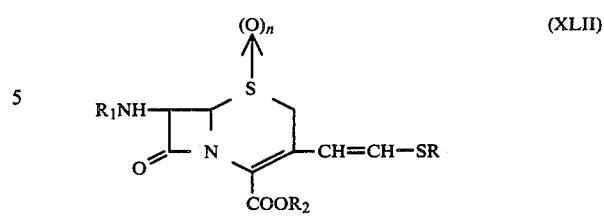

(XLII)

in which, n being defined as above, $R_1$ and $R_2$ are defined as under II. above and R has a corresponding definition.

The reaction is carried out under the conditions described above for the preparation of a product of the general formula (XXXVIII) from a product of the general formula (I) and a thiol of the general formula (XL).

It is understood that (if necessary) the radical R of the thiol is protected as described above, and that the removal of the protective radicals can be carried out under the conditions described above. However, it is preferable to retain the protective groups until the product of the general formula (XXXVIII) has been obtained.

A product of the general formula:

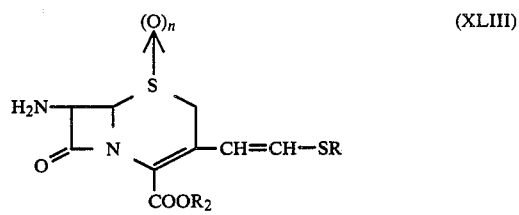

(XLIII)

in which R, $R_2$ and n are defined as above, is then prepared by removing the radical $R_1$ of a product of the general formula (XLII) in which $R_1$ is other than the hydrogen atom, or, if appropriate, simultaneously removing the protective radical $R_1$ and the other protective radicals of this product.

It is unnecessary to isolate the product of the general formula (XLIII) in order to use it in the further step of the synthesis.

The reaction is carried out under the conditions described above for the preparation of the product of the general formula (I) in which $R_1$ is a hydrogen atom.

The 3-thiovinylcephalosporin of the general formula (XXXVIII) in which R, $R°_1$ and $R°_2$ are defined as above is then prepared by acylating a 7-aminocephalosporin of the general formula (XLIII) by means of an acid represented by the general formula:

$R°_2$—OH (XLIV)

[in which $R°_1$, which is defined as above, is optionally protected if it contains radicals which can interfere with the reaction], or by means of a reactive derivative of this acid, under the conditions described above for the preparation of the products of the general formula (XXIII), and then reducing the oxide obtained (if n=1) and removing the protective radicals.

It is understood that:

the amino or alkylamino radicals which exist in some of the radicals R must be protected, and that the carboxyl, hydroxyl, formyl or acylalkyl radicals contained in the radicals R can be protected.

If R°₁ contains a radical of the general formula (IIa), the radical R^c₅ is necessarily a protective radical.

The protection and the removal of the protective radicals are carried out under the conditions described above.

The reduction of the oxide and the removal of the other protective radicals are carried out under the conditions described above.

It is also understood that if R contains a hydroxyl, sulpho, sulphinyl or sulphonyl substituent, it is preferred to use a product of the general formula (XLIII) in which n=0.

(III) The 3-thiovinylcephalosporins of the general formula (XXXVIII) in which R does not contain a substituent of the general formula (XXXIXc) can also be obtained by reacting a thioloester of the general formula:

$$R'_1-SR \qquad (XLV)$$

in which R'₁ either represents a radical of the general formula (II), R^c₅ representing a protective radical, or is defined in the same way as R₁ under 1. (b), and R is defined as above [it being understood that if it contains an amino or alkylamino substituent, the latter is protected, if it contains a hydroxyl or carboxyl substituent, the latter is free or protected, and if it contains a formyl or acylalkyl substituent, the latter is protected in the form of an acetal of the general formula (XXXIXa) or (XXXIXb)], with an 7-aminocephalosporin of the general formula (I) in which R₁ is a hydrogen atom and R₂ has the corresponding definition, and then reducing the sulphoxide obtained if n=1, and, if necessary, removing the protective radicals.

It is also understood that the radicals R'₁ which contain a group capable of interfering with the reaction are protected beforehand. The same applies to the oxime if R'₁ represents a radical of the general formula (II) in which R₅ is a hydrogen atom.

It is also preferable to use a product in which R'₁ does not contain a halogenated substituent.

In the same way as for the processes described above, if R contains a hydroxyl, sulpho, sulphinyl or sulphonyl substituent, it is preferred to use a product of the general formula (I) in which n=0.

The protection and the removal of the protective radicals are carried out under the conditions described above.

The reaction of the thioloester with the 7-aminocephalosporin of the general formula (I) is generally carried out in the presence of an acid acceptor such as an organic base, more particularly in the presence of a pyridine or a tertiary organic base of the general formula (XVII), in particular triethylamine, N,N-diisopropyl-N-ethylamine, diethylphenylamine or N-methylmorpholine.

The reaction is advantageously carried out in an organic solvent such as an amide (e.g. dimethylformamide or dimethylacetamide), an ether (e.g. tetrahydrofuran or dioxane), a chlorinated solvent (e.g. chloroform or methylene chloride), a ketone (e.g. acetone) or a nitrile (e.g. acetonitrile), or in a mixture of these solvents. It is also possible to carry out the reaction in the presence of an alkali metal bicarbonate, in one of the above-mentioned solvents, if appropriate in the presence of water.

The reaction is carried out at a temperature between −20° C. and the reflux temperature of the reaction mixture. If appropriate, it is carried out under nitrogen.

The reduction of the S-oxide is carried out under the conditions described above.

The thioloesters of the general formula (XLV) can be prepared by reacting an acid or a reactive derivative of an acid of the general formula:

$$R'_1OH \qquad (XLIVa)$$

with a thiol of the general formula (XL) (or with an alkali metal salt or alkaline earth metal salt of this thiol) and then, if appropriate, removing the protective radicals.

In the general formula (XLIVa), R'₁ represents a radical of the general formula (II) in which R₄ and R₅ (or R^c₅) are other than hydrogen, or alternatively R'₁ is defined in the same way as R₁ under 1.(b).

It is understood that the amino or alkylamino substituents of R'₁ and R are protected and that the hydroxyl or carboxyl substituents are free or protected.

It is also understood that the radical R is protected in the form of an acetal if it is desired to prepare a product of the general formula (XXXVIII) in which R contains a formyl or acylalkyl radical.

The reaction is carried out under the conditions described above for the preparation of a product of the general formula (XXII) from a product of the general formula (XXIV) and a reactive ester of the general formula (XXVI).

If it is desired to obtain a product in which R contains a carboxyl or sulpho radical, it is preferable to react a reactive derivative of the acid R'₁OH with the corresponding thiol.

If it is desired to obtain a thioloester in which R'₁ is a radical of the general formula (II), such as defined for R°₁, the t-butoxycarbonyl protective radical of the aminothiazole can be removed by treatment in an anhydrous acid medium. Preferably, trifluoroacetic acid is employed, the reaction being carried out at between 0° and 20° C. The trityl protective radical of the oxime can be removed by acidolysis, e.g. by means of anhydrous trifluoroacetic acid.

If necessary, the removal of the trityl protective group of a hydroxyl substituent of the thioloester is carried out under the conditions described above for the freeing of the oxime.

It is advantageous not to remove the protective groups until after the reaction of the thioloester with the product of the general formula (I) in which R₁ is the hydrogen atom.

(IV) The 3-thiovinylcephalosporins of the general formula (XXXVIII) in which R°₁ represents a radical of the general formula (II) (such as defined above, except that R₅ cannot represent a vinyl radical) and R does not contain a substituent of the general formula (XXXIXc) can be obtained by the following procedure:

A product of the general formula:

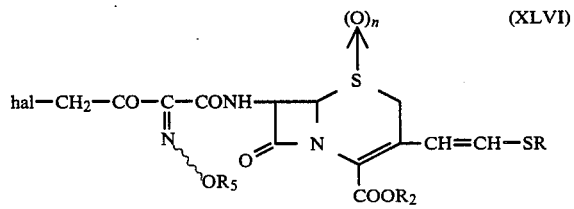

(XLVI)

in which R is defined as above, R₅ is defined as in the general formula (XXXII) and R₂, hal and n are defined as above, is prepared from a product of the general formula (XLIII) or a product of the general formula:

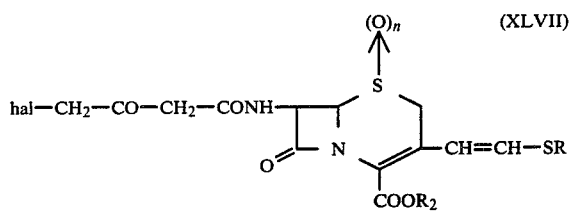
(XLVII)

[in which hal, $R_2$ and n are defined as above and R is defined as above] by applying the methods described above for the preparation of the product of the general formula (XXXII).

If the product of the general formula (XLVI) is prepared from a product of the general formula (XLIII), the radical R is protected beforehand if it contains an amino or alkylamino radical, and it is free or protected if it contains a hydroxyl, carboxyl, formyl or acylalkyl radical.

If the product of the general formula (XLVI) is prepared from a product of the general formula (XLVII), the radical R is protected beforehand if it contains an amino, alkylamino or formyl radical, and it is free or protected if it contains a hydroxyl, carboxyl or acylalkyl radical.

The protection and the removal of the protective radicals are carried out under the conditions described above.

A thiourea of the general formula (XXXI) is reacted with the product of the general formula (XLVI) under the conditions described above for the preparation of the products of the general formula (I) from the products of the general formula (XXXII), and then, if necessary, the sulphoxide obtained is reduced and, if appropriate, the protective radicals are removed.

If it is desired to obtain a product of the general formula (XXXVIII) in which R contains a formylalkyl or acylalkyl radical, this radical can be protected as an acetal in the form of a radical of the general formula (XXXIXa) or (XXXIXb), such as defined above.

The reduction of the sulphoxide and the removal of the protective radicals are carried out under the conditions described above.

The cephalosporin of the general formula (XLVII) can be prepared from a cephalosporin of the general formula (XLIII) by analogy with the method described for the preparation of the products of the general formula (XXXVII).

(V) The thiovinylcephalosporins of the general formula (XXXVIII) in which R represents a 5,6-dioxo-1,4,5,6-tetrahydro-1,2,4-triazin-3-yl radical substituted in the 1-position or 4-position, a 5,6-dioxo-1,2,5,6-tetrahydro-1,2,4-triazin-3-yl radical substituted in the 2-position, or a 1,3,4-triazol-5-yl, 2-alkoxycarbonyl-1,3,4-triazol-5-yl, 1,2,4-triazol-5-yl or 3-alkoxycarbonyl-1,2,4-triazol-5-yl radical substituted in the 1-position, by an alkyl radical containing 2 to 4 carbon atoms, which is substituted by a carbamoyloxy or acyloxy group (the acyl part of which is optionally substituted by an amino, alkylamino or dialkylamino radical), which are functional derivatives of the product of the general formula (XXXVIII) in which R is a radical — R —alk'OH chosen from amongst 5,6-dioxo-1-(or 4-)hydroxyalkyl-1,4,5,6-tetrahydro-1,2,4-triazin-3-yl, 5,6-dioxo-2-hydroxyalkyl-1,2,5,6-tetrahydro-1,2,4-triazin-3-yl, 1-hydroxyalkyl-1,3,4-(or 1,2,4-)triazol-5-yl, 2-alkoxycarbonyl-1-hydroxyalkyl-1,3,4-triazol-5-yl or 3-alkoxycarbonyl-1-hydroxyalkyl-1,2,4-triazol-5-yl, can be obtained by the carbamation or esterification of a product of the general formula:

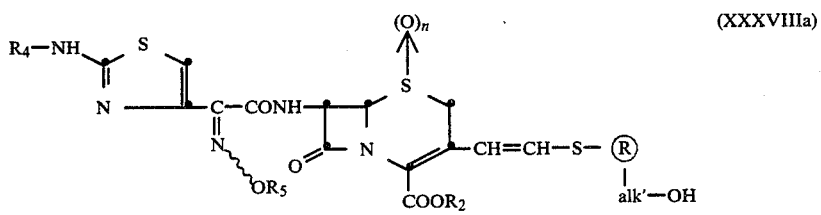
(XXXVIIIa)

(in which $R_2$, $R_4$, $R_5$, Ⓡ —alk'—OH and n are defined as above, except that $R_4$ cannot represent the hydrogen atom) by any known method for obtaining an ester or a carbamate from an alcohol without affecting the rest of the molecule, this being followed, if necessary, by the reduction of the sulphoxide obtained and the removal of the protective radicals.

The esterification is carried out at a temperature between −50° C. and the reflux temperature of the reaction mixture, in particular by condensation of the acid anhydride (or of another reactive derivative, e.g. a halide), in an inert organic solvent such as an ether (e.g. tetrahydrofuran), a chlorinated solvent (e.g. methylene chloride) or a mixture of such solvents, in the presence of a nitrogen-containing base such as pyridine, 4-dimethylaminopyridine or a trialkylamine (triethylamine), or of an alkaline condensation agent (e.g. sodium bicarbonate), this being followed, if necessary, by the reduction of the S-oxide obtained and the removal of the protective groups, in accordance with the methods described above.

The carbamate is obtained by any known method which does not affect the rest of the molecule. The reaction is carried out, in particular, with chlorosulphonyl or trichloroacetyl isocyanate, in an inert organic solvent, e.g. tetrahydrofuran or acetonitrile, at a temperature between −80° and 20° C., this being followed by the removal of the protective groups.

(VI) The 3-thiovinylcephalosporins of the general formula (XXXVIII) in which R represents a 5,6-dioxo-1,4,5,6-tetrahydro-1,2,4-triazin-3-yl radical substituted in the 1-position or 4-position, a 5,6-dioxo-1,2,5,6-tetrahydro-1,2,4-triazin-3-yl radical substituted in the 2-position, or a 1,3,4-triazol-5-yl, 2-alkoxycarbonyl-1,3,4-triazol-5-yl, 1,2,4-triazol-5-yl or 3-alkoxycarbonyl-1,2,4-triazol-5-yl radical substituted in the 1-position, by an alkyl radical containing 2 to 4 carbon atoms, which is substituted by a sulphoamino, alkylsulphonylamino or sulphamoylamino group, an acylamino group (the acyl part of which is optionally substituted by hydroxyl, amino, alkylamino or dialkylamino) or an alkoxycarbonylamino, ureido, alkylureido or dialkylureido group, or represents a 1,3,4-thiadiazol-5-yl radical substituted by an acylamino or acylaminoalkyl radical, or represents a 1,3,4-oxadiazol-5-yl radical substituted by an acylaminoalkyl radical, or represents a tetrazol-5-yl radical substituted in the 1-position by an alkyl radical containing 2 to 4 carbon atoms, which is substituted by an acylamino, sulphamoylamino, sulphoamino, ureido, alkyureido or dialkylureido group, and $R°_1$ and $R°_2$ have the corresponding definitions, which are all functional derivatives of the amine which corresponds thereto, can be obtained by treating an amine of the general formula:

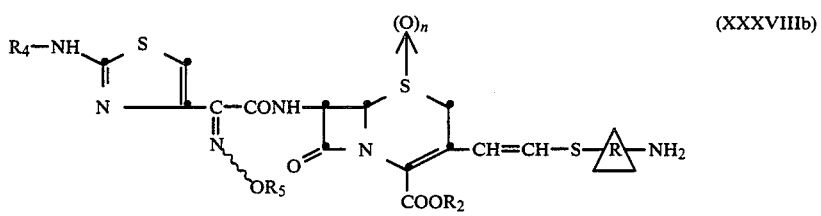

(XXXVIIIb)

in which $R_4$, $R_5$, $R_2$ and n are defined as above under (V) and —R—$NH_2$ represents a 5,6-dioxo-1,4,5,6-tetrahydro-1,2,4-triazin-3-yl radical substituted in the 1-position or 4-position, a 5,6-dioxo-1,2,5,6-tetrahydro-1,2,4-triazin-3-yl radical substituted in the 2-position, or a 1,3,4-triazol-5-yl, 2-alkoxycarbonyl-1,3,4-triazol-5-yl, 1,2,4-triazol-5-yl or 3-alkoxycarbonyl-1,2,4-triazol5-yl radical substituted in the 1-position, by an aminoalkyl radical, the alkyl part of which contains 2 to 4 carbon atoms, or a 1,3,4-thiadiazol-5-yl radical substituted by an amino or aminoalkyl radical, or a 1,3,4-oxadiazol-5-yl radical substituted by an aminoalkyl radical, or a tetrazol-5-yl radical substituted in the 1-position by an aminoalkyl radical, the alkyl part of which contains 2 to 4 carbon atoms, by any method which is in itself known for forming an amide, sulphamide, carbamate or urea group without affecting the rest of the molecule, and then, if necessary, reducing the sulphoxide and removing the protective groups.

It is understood that the products which contain a sulpho, sulphonyl or sulphamoyl group are preferably prepared from a product of the general formula (XXXVIIIb) in which n=0.

Furthermore, if it is desired to prepare a product in which the radical R contains an amino or hydroxyl group, it is necessary to protect these radicals in the reactant used. Likewise, if $R_5$ represents the hydrogen atom, it is necessary to protect the oxime. If $R_5$ contains a carboxyl group, the latter is free or protected.

If it is desired to prepare a product of the general formula (XXXVIII) in which the radical R contains an alkylsulphonylamino, sulphamoylamino, acylamino (substituted or unsubstituted), alkoxycarbonylamino or dialkylureido substituent, the reaction is advantageously carried out with respectively the corresponding chlorosulphonyl derivative, acid chloride, chloroformate or dialkylcarbamoyl chloride, under the conditions described above for the reaction of the chloride of the acid of the general formula (XXV) with the 7-aminocephalosporin of the general formula (XXIV).

If it is desired to prepare a product of the general formula (XXXVIII) in which the radical R contains a sulphoamino, alkylsulphonylamino or acylamino (substituted or unsubstituted) substituent, the reaction can be carried out by means of the corresponding acid anhydride, under the conditions described above for the reaction of the product of the general formula (XXV) in the form of the anhydride.

If it is desired to obtain a product of the general formula (XXXVIII) in which R contains an acylamino radical (substituted or unsubstituted), it is also possible to carry out the reaction with the corresponding acid, under the operating conditions described above for the use of the acid of the general formula (XXV).

If it is desired to obtain a product of the general formula (XXXVIII) in which R contains a ureido or alkylureido radical, an alkali metal isocyanate or an alkyl isocyanate is reacted respectively with the corresponding product of the general formula (XXXVIIIb), in an aqueous-organic or organic medium (e.g. in tetrahydrofuran), at a temperature between —20° and 60° C.

The reduction and the removal of the protective radicals are carried out under the conditions described above.

(VII) The 3-thiovinylcephalosporins of the general formula (XXXVIII) in which R represents a 5,6-dioxo-1,4,5,6-tetrahydro-1,2,4-triazin-3-yl radical substituted in the 1-position or 4-position, a 5,6-dioxo-1,2,5,6-tetrahydro-1,2,4-triazin-3-yl radical substituted in the 2-position, or a 1,3,4-triazol-5-yl, 2-alkoxycarbonyl-1,3,4-triazol-5-yl, 1,2,4-triazol-5-yl or 3-alkoxycarbonyl-1,2,4-triazol-5-yl radical substituted in the 1-position, by a thiazolidin-2-yl-alkyl radical, by a radical of the general formula (XXXIXc) or by a hydroxyiminoalkyl or alkoxyiminoalkyl radical, the iminoalkyl part of which contains 2 to 5 carbon atoms, or represents a tetrazol-5-yl radical substituted in the 1-position by a hydroxyiminoalkyl or alkoxyiminoalkyl radical, the iminoalkyl part of which contains 2 to 5 carbon atoms, and $R°_1$ and $R°_2$ have the corresponding definitions, which are addition derivatives of the product of the general formula (XXXVIII) in which R is one of the heterocyclic rings mentioned above, substituted by a formylalkyl radical (or its hydrate form), can be obtained from an aldehyde of the general formula:

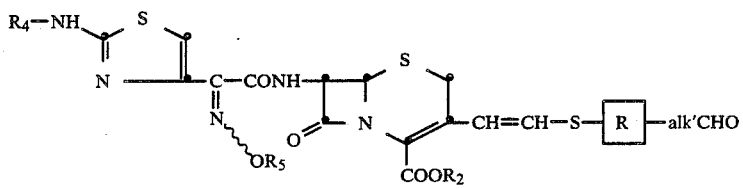

(XXXVIIIc)

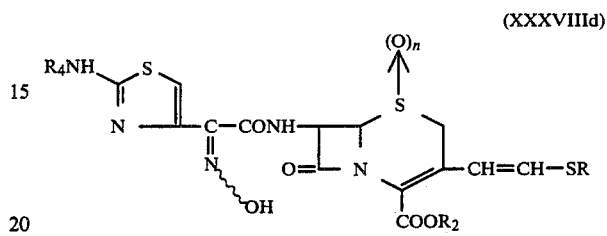

(XXXVIIId)

in which R$_2$ and R$_4$ are defined as above, R$_5$ is defined as above under (V) and —[R]—alk'CHO represents a 5,6-dioxo-1-(or 4-)formylalkyl-1,4,5,6-tetrahydro-1,2,4-triazin-3-yl, 5,6-dioxo-2-formylalkyl-1,2,5,6-tetrahydro-1,2,4-triazin-3-yl, 1-formylalkyl-1,3,4-(or 1,2,4-)triazol-5-yl, 2-alkoxycarbonyl-1-formylalkyl-1,3,4-triazol-5-yl, 3-alkoxycarbonyl-1-formylalkyl-1,3,4-triazol-5-yl or 1-formylalkyltetrazol-5-yl radical, by the addition respectively of cysteamine, an alcohol, hydroxylamine or an alkoxyamine, in accordance with the known methods for forming addition derivatives of carbonylated groups, this being followed, if necessary, by the removal of the protective radicals.

The reaction is generally carried out in an organic solvent, at a temperature between 20° C. and the reflux temperature of the reaction mixture.

The organic solvents are chosen according to the solubility of the products. If a product of the general formula (XXXVIIIc) in which R$_4$, R$_2$ and R$^c_5$ (contained in R$_5$) are other than hydrogen is used, solvents such as tetrahydrofuran, acetonitrile, alcohols and ketones are advantageously used. If a product of the general formula (XXXVIIIc) in which R$_4$, R$_2$ and R$^c_5$ (contained in R$_5$) are hydrogen atoms is used, the reaction is advantageously carried out in solvents such as pyridine, dimethyl sulphoxide or dimethylformamide.

If it is desired to prepare a product of the general formula (XXXVIII) in which the radical R contains a substituent of the general formula (XXXIXc), the reaction is carried out in an acid medium.

(VIII) The 3-thiovinylcephalosporins of the general formula (XXXVIII) in which R°$_2$ represents a radical of the general formula (V), in which R$_8$ and R$_9$ are defined as above, and R°$_1$ has a corresponding definition can also be obtained by esterifying a product of the general formula (XXXVIII) in which R°$_2$ represents a hydrogen atom and in which the amine group and, if necessary, the acid group of R°$_1$ have been protected beforehand, by any method which is in itself known for preparing an ester from an acid without affecting the rest of the molecule.

The reaction is carried out, in particular, under the conditions described above for the preparation of products of the general formula (XXII) or (XXIV), in which formulae R$_2$ is a radical of the general formula (V).

(IX) The 3-thiovinylcephalosporins of the general formula (XXXVIII) in which R does not contain a substituent of the general formula (XXXIXc) and in which R°$_1$ contains a radical of the general formula (IIa) can also be obtained by reacting a product of the general formula (XXXVI) with a cephalosporin of the general formula:

in which R, R$_2$, R$_4$ and n are defined as above, except that R$_4$ cannot represent a hydrogen atom, and then, if necessary, reducing the sulphoxide obtained and removing the protective groups.

The acid group of the product of the general formula (XXXVI) can be protected by any protective group defined above for the protection of the carboxyl radicals.

It is understood that the amino and alkylamino groups which exist in some of the radicals R are protected, and that the formyl groups are free or protected.

The reaction is generally carried out in the presence of an inorganic or organic base (e.g. sodium hydroxide, potassium hydroxide, sodium hydride, potassium carbonate or a nitrogen-containing base such as triethylamine), in an organic solvent such as a chlorinated solvent (e.g. methylene chloride or dichloroethane), an ether (e.g. tetrahydrofuran or dioxane), a ketone (e.g. acetone) or an amide (e.g. dimethylformamide), if appropriate in the presence of water.

The reduction of the sulphoxide and the removal of the protective radicals are carried out under the conditions described above.

(X) The 3-thiovinylcephalosporins of the general formula (XXXVIII) in which R does not contain a substituent of the general formula (XXXIXc) can also be obtained from a product or a mixture of the isomers of the product of the general formula (XVIa), by reaction with a thiol of the general formula (XL) (or one of its alkali metal or alkaline earth metal salts) in which R is defined as above and protected, if necessary, under the conditions defined above under (I), this being followed, if appropriate, by the reduction of the sulphoxide obtained if n=1, and the removal of the protective groups.

The reaction is carried out under the conditions described above for the preparation of the products of the general formula (XXXVIII) from a product of the general formula (I) and a product of the general formula (XL). The conditions of protection (and freeing) of the various radicals are also the same as for the process described under (I).

The products of the general formulae (XVIa), (XXXII) or (XXXVII) in which n=1 can be obtained by oxidising the corresponding products in which n=0, in accordance with the method described in German Patent Application No. 2,637,176.

The isomers of the products of the general formula (I), (XVI), (XVIa), (XVIII), (XXXII), (XXXVII), (XXXVIII), (XLII), (XLIII), (XLVI) or (XLVII) can be separated by chromatography or by crystallisation.

The new products of the general formula (I) in which there is an amino radical can be converted to addition salts with acids. According to the processes indicated, the products are obtained, if appropriate, in the form of the trifluoroacetate, the para-toluenesulphonate, the methanesulphonate, the phosphate, or the solvate with formic acid. The products obtained in the form of these salts can be freed and converted to salts of other acids in accordance with the usual methods.

The products of the general formula (I) which contain a carboxyl radical can also be converted to metal salts or to addition salts with nitrogen-containing organic bases in accordance with the methods which are in themselves known. These salts can be obtained by reacting a metal base (e.g. an alkali metal base or alkaline earth metal base) or an amine with a product of the general formula (I), in a suitable solvent such as an alcohol, an ether or water, or by means of an exchange reaction with a salt of an organic acid. The salt formed precipitates, after concentration, if necessary, of its solution, and is separated off by filtration or decantation.

Examples of salts which may be mentioned are the salts with alkali metals (such as the potassium, sodium or lithium salts) or with alkaline earth metals, the salts of nitrogen-containing bases (dimethylamine, diethylamine, diisopropylamine, dicyclohexylamine, N,-ethylpiperidine and N-methylmorpholine salts) and the addition salts with mineral acids (such as hydrochlorides or hydrobromides) or organic acids (formates, trifluoroacetates, p-toluenesulphonates, naphthalenesulphonates or oxalates).

The cephalosporin derivatives of the general formula (XXXVIII), described under $\alpha_1$., and their pharmaceutically acceptable salts, possess particularly valuble anti-bacterial properties.

In vitro, they have been shown to be active at a concentration of between 0.5 and 10 μg/cc against staphylococcus strains sensitive to penicillin G (*Staphylococcus aureus* Smith) and at a concentration of between 0.01 and 2 μg/cc against *Escherichia coli*, NIHJ strain. Furthermore, the majority of them have been shown to be active at a concentration of between 2 and 125 μg/cc against *Pseudomonas aeruginosa*.

In vivo, they have been shown to be active at a daily dose of between 0.5 and 15 mg/kg, administered subcutaneously, against experimental infections caused in mice by *Staphylococcus aureus* Smith (sensitive to penicillin G), and at daily doses of between 0.01 and 10 mg/kg, administered subcutaneously, against experimental infections caused in mice by *Escherichia coli* (NIHJ strain).

Furthermore, the $LD_{50}$ of the products of the general formula (XXXVIII) is between 1 g/kg and doses of more than 2.5 g/kg, administered subcutaneously to mice.

The cephalosporin derivatives of the general formula (XXXVIII), such as defined under $\beta_1$., are described for their anti-bacterial properties or as intermediates for the preparation of antibiotic substances in U.S. Pat. No. 4,065,620.

Of especial interest are the compounds of formula (I) having the E form in which $R_2$ represents hydrogen or benzhydryl and either $R_3$ represents halogen, and $R_1$ represents hydrogen, alkoxycarbonyl, a radical of the general formula (VIII) in which Ar is phenyl and B is amino or protected amino or a radical of the general formula (II), syn form in which $R_4$ is trityl and $R_5$ is alkyl, or $R_3$ represents halogen or tosyloxy and $R_1$ represents a radical of the general formula (II), syn form in which $R_4$ is trityl and $R_5$ is a radical of the general formula (IIa) and, among these products, those in which either $R_3$ represents chlorine and $R_1$ represents hydrogen, t-butoxycarbonyl, a radical of the general formula (VIII) in which Ar is phenyl and B is amino or t-butoxycarbonylamino or a radical of the general formula (II), syn form, in which $R_4$ is trityl and $R_5$ is methyl, or $R_3$ represents chlorine or tosyloxy and $R_1$ represents a radical of the general formula (II), syn form in which $R_4$ is trityl and $R_5$ is a radical of the general formula (IIa).

The following Examples, which are given without implying a limitation, show how the invention can be put into practice.

In these Examples, the products are named according to the nomenclature of Chemical Abstracts. It is understood that all the products which are mentioned exhibit the stereochemistry given by the partial general formula:

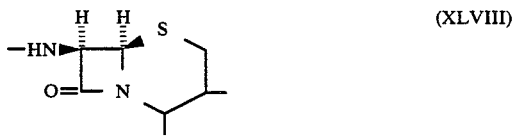

(XLVIII)

EXAMPLE 1 p-Toluenesulphonyl chloride (1.31 g) is added to a solution, cooled to 5° C., of the syn isomer of 2-ben zhydryloxycarbonyl-7-{2-[(2-t-butoxycarbonylprop-2-yl)-oxyimino]-2-(2-tritylaminothiazol-4-yl)-acetamido}-3-formylmethyl-8-oxo-5-thia-1-azabicyclo[4.2.0]oct-2-ene (product 1a) (4.45 g) in pyridine (50 cc). The temperature is left to rise to 20° C. over a period of 30 minutes, the mixture is stirred for 1 hour at 20° C. and poured into iced water (300 cc), the water is decanted and the insoluble pasty product is taken up in ethyl acetate (300 cc). The solution is washed with 1N hydrochloric acid (100 cc), a saturated solution of sodium bicarbonate (100 cc) and a saturated solution of sodium chloride (100 cc), dried over sodium sulphate and filtered and the filtrate is concentrated to dryness at 20° C. under 20 mm Hg (2.7 kPa). The product thus obtained is used as such for the remainder of the synthesis. This product (1 g) is purified by chromatography on a column of silica gel (0.05–0.2) (20 g) (diameter of the column: 1.7 cm), elution being carried out with an 80/20 (by volume) mixture of cyclohexane and ethyl acetate, and 50 cc fractions being collected. Fractions 4 to 12, containing the pure product, are evaporated to dryness under reduced pressure (30 mm Hg; 4 kPa) at 30° C. to give a mixture of the E and Z forms (in proportions—determined by NMR—of 75% of the E form and 25% of the Z form) of the syn isomer of 2-benzhydryloxycarbonyl-7-{2-[(2-t-butoxycarbonyl-prop-2-yl)-oxyimino]-2-(2-tritylaminothiazol-4-yl)-acetamido}-8-oxo-3-(2-tosyloxyvinyl)-5-thia-1-azabicyclo[4.2.0]oct-2-ene (product 1) (0.43 g) in the form of a pale yellow solid.

Infra-red spectrum (CHBr$_3$), characteristic bands (cm$^{-1}$): 3,400, 3,260, 1,790, 1,720, 1,680, 1,630, 1,595, 1,580, 1,520, 1,490, 1,450, 1,380, 1,370, 1,190, 1,180, 1,070, 835, 750.

Proton NMR spectrum (350 MHz, CDCl$_3$, δ in ppm, J in Hz): mixture of E and Z isomers in the proportions 75/25.

E form: 1.45 (s, 9H, —C(CH$_3$)$_3$); 1.62 and 1.67 (2s, 6H, =N—O—C(CH$_3$)$_2$—); 2.48 (s, 3H, —CH$_3$ of the tosyl); 3.42 and 3.50 (2d, J=18, 2H, —S—CH$_2$—); 5.08 (d, J=4, 1H, —H in the 6-position); 6.00 (dd, J=4 and 9, 1H, —H in the 7-position); 6.78 (s, 1H, H of the thiazole); 6.88 (b, 1H, —NH—C(C$_6$H$_5$)$_3$); 6.90 and 6.97 (2d, J=12, 2H, —CH=CH—S—); 6.92 (s, 1H, —COO—CH(C$_6$H$_5$)$_2$); 8.20 (d, J=9, 1H, —CO—NH—).

Z form: 6.20 and 6.47 (2d, J=7, —CH=CH—S—Z); 2.45 (s, —CH$_3$ of the tosyl).

The product (1a) can be obtained in the following manner:

A mixture of the E form of the syn isomer of 2-benzhydryloxycarbonyl-3-(2-dimethylaminovinyl)-7-{2-[(2-t-butoxycarbonylprop-2-yl)-oxyimino]-2-(2-tritylaminothiazol-4-yl)-acetamido}-8-oxo-5-thia-1-azabicyclo[4.2.0]oct-2-ene (product 1b) (6.45 g), dissolved in ethyl acetate (100 cc), and 1N hydrochloric acid (64 cc) is stirred for 1 hour at 20° C. The organic phase is decanted, washed with water (100 cc), a saturated aqueous solution of sodium bicarbonate (100 cc) and a saturated aqueous solution of sodium chloride (100 cc), dried over sodium sulphate and filtered and the filtrate is concentrated to dryness at 20° C. under 20 mm Hg (2.7 kPa). A crude product (1a) (4.95 g) is collected in the form of a hard brown foam.

Infra-red spectrum (CHBr$_3$), characteristic bands (cm$^{-1}$): 3,400, 3,270, 2,720, 1,770, 1,725, 1,685, 1,525, 1,495, 1,450, 1,370, 755, 700.

Proton NMR spectrum (350 MHz, CDCl$_3$, δ in ppm, J in Hz): 1.45 (s, 9H, —C(CH$_3$)$_3$); 1.64 and 1.67 (2s, 6H, (—CH$_3$)$_2$); 3.25 and 3.54 (2d, J=18, 2H, —SCH$_2$—); 3.50 and 3.73 (2d, J=16, 2H, —CH$_2$CHO); 5.10 (d, J=4, 1H, H in the 6-position); 6.06 (dd, J=4 and 9, 1H, H in the 7-position); 6.77 (s, 1H, H of the thiazole); 6.90 (s, 1H, —COOCH<); 8.22 (d, J=9, 1H, —CONH—); 9.58 (s, 1H, —CHO).

The product (1b) can be obtained in the following manner:

t-Butoxy-bis-dimethylaminomethane (1.9 cc) is added, whilst stirring, to a solution, at 80° C., under nitrogen, of the syn isomer of 2-benzhydryloxycarbonyl-7-{2-[(2-t-butoxycarbonylprop-2-yl)-oxyimino]-2-(2-tritylaminothiazol-4-yl)-acetamido}-3-methyl-8-oxo-5-thia-1-azabicyclo[4.2.0]oct-2-ene (6 g) in dimethylformamide (64 cc), and the reaction is continued for 15 minutes. The mixture is then poured into a mixture of ethyl acetate (200 cc) and water (200 cc), the organic phase is decanted, washed with water (3×100 cc) and a saturated aqueous solution of sodium chloride (100 cc), dried over sodium sulphate and filtered and the filtrate is concentrated to dryness at 20° C. under 20 mm Hg (2.7 kPa). This yields crude 2-benzhydryloxycarbonyl-3-(2-dimethylaminovinyl)-7-{2-[(2-t-butoxycarbonylprop-2-yl)-oxyimino]-2-(2-tritylaminothiazol-4-yl)-acetamido}-8-oxo-5-thia-1-azabicyclo[4.2.0]oct-2-ene, syn isomer, E form (6.5 g) in the form of a hard brown foam.

A sample (2.2 g) is purified by chromatography on a column (diameter 4 cm, height 20 cm) of Merck silica gel (0.04–0.06), elution being carried out with a cyclohexane/ethyl acetate mixture (65:35 by volume) under a pressure of 40 kPa, and taking fractions of 50 cm$^3$. Fractions 14 to 24 are evaporated to dryness. 2-Benzhydryloxycarbonyl-3-(2-dimethylaminovinyl)-7-{2-[(2-t-butoxycarbonylprop-2-yl)-oxyimino]-2-(2-tritylaminothiazol-4-yl)-acetamido}-8-oxo-5-thia-1-azabicyclo[4.2.0]oct-2-ene, syn isomer, E form (1.2 g) is thus obtained.

Infra-red spectrum (CHBr$_3$), characteristic bands (cm$^{-1}$): 3,400, 3,280, 1,770, 1,720, 1,680, 1,610, 1,525, 1,490, 1,450, 1,370, 940, 750, 735.

Proton NMR spectrum (350 MHz, CDCl$_3$, δ in ppm, J in Hz): 1.45 (s, 9H, —C(CH$_3$)$_3$); 1.64 and 1.71 (2s, 6H, =N—O—C(CH$_3$)$_2$—); 2.93 (s, 6H, —N(CH$_3$)$_2$); 3.20 and 3.30 (2d, J=14, 2H, —S—CH$_2$—); 5.18 (d, J=4, 1H, —H in the 6-position); 5.71 (dd, J=4 and 9, 1H, —H in the 7-position); 6.61 and 6.82 (2d, J=14, 2H, —CH=CH—S—); 6.88 (s, 1H, H of the thiazole); 6.92 (s, 1H, —COO—CH(C$_6$H$_5$)$_2$); 6.92 (s broad, 1H, —NH—C(C$_6$H$_5$)$_3$); 8.28 (d, J=9, 1H, —CO—NH—).

2-Benzhydryloxycarbonyl-7-{2-[(2-t-butoxycarbonylprop-2-yl)-oxyimino]-2-(2-tritylaminothiazol-4-yl)-acetamido}-3-methyl-8-oxo-5-thia-1-azabicyclo[4.2.0]oct-2-ene, syn isomer, can be prepared in the following way. A solution of phosgene in chlorobenzene (1.3 m), (40 cm$^3$) is added at −10° C. over 30 minutes and with stirring to a solution of 2-(2-t-butoxycarbonylprop-2-yl)-oxyimino-2-(2-tritylaminothiazol-4-yl)-acetic acid (25.58 g), prepared according to Belgian Pat. No. 876541 in a mixture of dichloromethane (250 cm$^3$) and dimethylacetamide (13.9 cm$^3$). The mixture is stirred for a further 3 hours at −10° C. and a solution of 7-amino-2-benzhydryloxycarbonyl-3-methyl-8-oxo-5-thia-1-azabicyclo[4.2.0]oct-2-ene (16.29 g) in dichloromethane (250 cm$^3$) is then added drop by drop over 1 hour 15 minutes. After 1 hour 15 minutes at −10° C., the mixture is washed with 2% aqueous sodium bicarbonate solution (200 cm$^3$) and water (200 cm$^3$) and then dried over anhydrous sodium sulphate and concentrated to dryness at 30° C. under 20 mm Hg (2.7 kPa). The residue was chromatographed on a column of Merck silica gel (200 g, 0.05–0.2), the column diameter being 4 cm. Elution was effected with a mixture of cyclohexane and ethylacetate (70:30 by volume) taking fractions of 120 cm$^3$. Fractions 6 to 10 are concentrated to dryness at 30° C. under 20 mm Hg (2.7 kPa). 2-Benzhydryloxycarbonyl-7-[2-(2-t-butoxycarbonylprop-2-yl)-oxyimino-2-(2-tritylaminothiazol-4-yl)-acetamido]-3-methyl-8-oxo-5-thia-1-azabicyclo[4.2.0]oct-2-ene, syn isomer, (8.5 g) is thus obtained as a yellow foam. The infra-red spectrum of this product (in CHBr$_3$) shows characteristic bands at (cm$^{-1}$): 3,400, 3,270, 1,790, 1,725, 1,685, 1,525, 1,500, 1,450, 1,380, 1,370, 760, and 740.

EXAMPLE 2

A solution of the chlorine/triphenyl phosphite addition compound is prepared by adding a solution of triphenyl phosphite (1.55 g) in methylene chloride (5 cc), over a period of 15 minutes, to a 10% strength (weight/volume) solution of chlorine in methylene chloride (4 cc), cooled to −5° C. The resulting solution is added, over a period of 90 minutes, at −10° C., to a solution of 2-benzhydryloxycarbonyl-7-t-butoxycarbonylamino-8-oxo-3-(2-oxoethyl)-5-thia-1-azabicyclo[4.2.0]oct-2-ene (product 2a) (2.4 g) and pyridine (0.4 cc) in methylene chloride (15 cc). The reaction mixture is washed with distilled water (20 cc), a saturated solution of sodium bixcarbonate (20 cc) and distilled water (2×20 cc) and then dried over magnesium sulphate and concentrated to dryness under reduced pressure (30 mm Hg; 4 kPa) at 30° C. This yields an equimolecular mixture (4.6 g) of 2-benzhydryloxycarbonyl-7-t-butoxycarbonylamino-3-(2,2-dichloroethyl)-8-oxo-5-thia-1-azabicyclo[4.2.0]oct-2-ene (product 2b) and triphenyl phosphate. This mixture can be used without additional purification for the remainder of the synthesis, by redissolving it in dry methylene chloride (15 cc) and adding a solution of 85% pure metachloroperbenzoic acid (1.22 g) in methylene chloride (30 cc), over a period of 20 minutes, to the above solution, cooled to −10° C. The insoluble material is removed by filtration and the filtrate is washed with a saturated solution of sodium bicarbonate (2×25 cc) and a saturated solution of sodium chloride (2×25 cc) and then dried over magnesium sulphate. The residue obtained after evaporating the solvent off under reduced pressure (30 mm Hg; 4 kPa) at 35° C. is chromatographed on a column of silica (0.04–0.06) (diameter of the column: 2 cm; height: 30 cm), elution being carried out under 50 kPa with a mixture of cyclohexane and ethyl acetate (60/40 by volume), and 30 cc fractions being collected. Fractions 6 to 12 are combined and concentrated to dryness under reduced pressure (30 mm Hg; 4 kPa) at 40° C. This yields a hard yellow foam (1.3 g) consisting mainly of 2-benzhydryloxycarbonyl-7-t-butoxycarbonylamino-3-(2,2-dichloroethyl)-8-oxo-5-thia-1-azabicyclo[4.2.0]oct-2-ene-5-oxide (product 2 c). Mass spectrum: molecular peak: m/e=578.

Proton NMR spectrum (350 MHz, CDCl$_3$, δ in ppm, J in Hz): 1.48 (s, 9H, (CH$_3$)$_3$C—); 3.10 (dd, J=5 and 14, 1H, CH$_2$—CHCl$_2$); 3.66 (dd, J=7 and 14, 1H, 2nd H of the C$\overline{H_2}$—CHCl$_2$); 3.41 and 3.96 (2d, J=18, 2H, —S-(O)C$\overline{H_2}$—); 4.53 (d, J=4, 1H, H in the 6-position); 5.78 (d, J=9, 1H, —CONH—); 5.83 (dd, J=4 and 9, 1H, H in the 7-position); 5.87 (dd, J=5 and 7, 1H, —CH$_2$CHCl$_2$); 6.98 (s, 1AH, —CHAr$_2$); 7.2 to 7.5 (m, 10H aromatic).

The purified product (2b) is obtained by chromatographing an equimolecular mixture (4.6 g) of this product with triphenyl phosphate, such as obtained above, on a column of silica gel (0.2–0.06) (30 g), elution being carried out with methylene chloride and 10 cc fractions being collected. Fractions 2 to 11 are combined and concentrated to dryness under reduced pressure (30 mm Hg; 4 kPa) at 30° C. The residue obtained is again subjected to chromatography on a column of silica (0.04–0.06) (diameter of column: 2 cm; height: 30 cm), elution being carried out under 50 kPa with a mixture of cyclohexane and ethyl acetate (80/20 by volume) and 10 cc fractions being collected. Fractions 7 and 8, containing the pure product, are concentrated to dryness under reduced pressure (30 mm Hg; 4 kPa) at 35° C. and the product is dried under reduced pressure (0.2 mm Hg; 0.027 kPa) at 25° C.

Mass spectrum: molecular peak: m/e=562.

Proton NMR spectrum (350 MHz, CDCl$_3$, δ in ppm, J in Hz): 1.46 (s, 9H, (CH$_3$)$_3$C—); 3.20 and 3.28 (2dd, J=9 and 14, 2H, —CH$_2$—CHCl$_2$); 3.65·(limiting AB-type, J=18, 2H, —SCH$_2$—); 5.0 (d, J=4, 1H, H in the 6-position); 5.25 (d, J=9, 1H, —CONH—); 5.67 (dd, J=4 and 9, 1H, H in the 7-position); 5.98 (dd, J=9 and 4, 1H, —CH$_2$—CHCl$_2$); 6.95 (s, 1H, —CO$_2$CH(C$_6$H$_5$)$_2$); 7.20 to 7.50 (m, 10H aromatic).

A solution of product (2c) (3.3 g) and triethylamine (0.88 cc) in dry tetrahydrofuran (50 cc) is stirred at 25° C. for 16 hours and the reaction mixture is then diluted with ethyl acetate (200 cc). The organic solution is washed with distilled water (5×60 cc), dried over sodium sulphate and concentrated to dryness under reduced pressure (30 mm Hg; 4 kPa) at 35° C. This yields the E form of 2-benzhydryloxycarbonyl-7-t-butoxycarbonylamino-3-(2-chlorovinyl)-8-oxo-5-thia-1-azabicyclo[4.2.0]oct-2-ene-5-oxide (product 2) (3.1 g) in the form of a hard orange foam.

Infra-red spectrum (CHBr$_3$), characteristic bands (cm$^{-1}$): 3,400, 1,800, 1,715, 1,590, 1,570, 1,500, 1,450, 1,390, 1,365, 1,040, 960, 755.

Proton NMR spectrum (350 MHz, CDCl$_3$, δ in ppm, J in Hz): 1.48 (s, 9H, (CH$_3$)$_3$C—); 3.20 and 3.94 (2d, J=18, 2H, —S(O)CH$_2$—); 4.53 (d, J=4, 1H, H in the 6-position); 5.78 (d, J=9, 1H, —CONH—); 5.86 (dd, J=4 and 9, 1H, H in the 7-position); 6.45 (d, J=14, 1H, —CH=CHCl); 7.03 (s, 1H, —CO$_2$CH(C$_6$H$_5$)$_2$); 7.49 (d, J=14, 1H, —CH=CHCl); 7.20 to 7.60 (m, 10H aromatic).

The product (2a) can be obtained in the following manner:

A solution of the E form of 2-benzhydryloxycarbonyl-7-t-butoxycarbonylamino-3-(2-dimethylaminovinyl)-8-oxo-5-thia-1-azabicyclo[4.2.0]oct-2-ene (product 2d) (1.07 g) in ethyl acetate (10 cc) is stirred for 1 hour, at 25° C., with a 1N aqueous solution of hydrochloric acid (5 cc). The organic phase is decanted, washed with a saturated aqueous solution of sodium chloride (4×50 cc) and then dried over magnesium sulphate and filtered. The solvent is evaporated off to dryness under reduced pressure to give a product (1 g), the IR spectrum of which shows that it consists mainly of product (2a).

Rf=0.57 [silica gel chromatography plate; eluent: 60/40 (by volume) cyclohexane/ethyl acetate].

Infra-red spectrum (CHBr$_3$ solution), characteristic bands (cm$^{-1}$): 2,840, 1,785, 1,720.

Proton NMR spectrum (350 MHz, CDCl$_3$, δ in ppm, J in Hz): 1.47 (s, 9H, (CH$_3$)$_3$C—O—); 3.24 and 3.55 (AB-type, J=18, 2H, —SCH$_2$—); 3.50 and 3.66 (AB-type, J=16, 2H, —CH$_2$CHO); 4.98 (d, J=4.5, 1H, H in the 6-position); 5.25 (d, J=9, 1H, —CONH—); 5.65 (dd, J=4.5 and 9, 1H, H in the 7-position); 6.87 (s, 1H, —CO$_2$CH<); 7.2 to 7.5 (b, 10H aromatic); 9.54 (s, 1H, —CHO).

The product (2d) can be obtained by the following procedure:

A solution of 2-benzhydryloxycarbonyl-7-t-butoxycarbonylamino-3-methyl-8-oxo-5-thia-1-azabicyclo[4.2.0]-oct-3-ene (product 2e) (1.0 g) in anhydrous N,N-dimethylformamide (100 cc) is heated to 80° C. under a nitrogen atmosphere. Bis-dimethylamino-t-butoxymethane (0.86 cc) is then added rapidly. The reaction mixture is kept at 80° C. for 5 minutes and then poured into ethyl acetate (50 cc). After the addition of distilled water (25 cc), the organic phase is decanted, washed with distilled water (4×25 cc), dried over magnesium sulphate and filtered. The filtrate is concentrated to dryness under reduced pressure (20 mm Hg; 2.7 kPa) at 30° C. and a product (1.10 g) consisting mainly of product (2d) is obtained in the form of a hard orange foam.

RF=0.29; silica gel chromatography plate [50/50 (by volume) methylene chloride/ethyl acetate].

Infra-red spectrum (CHBr$_3$), characteristic bands (cm$^{-1}$): 3,430, 3,350, 2,820, 1,765, 1,715, 1,690, 1,615, 1,540, 1,505, 1,495, 1,465, 1,370, 1,240, 940, 745, 600.

UV/visible spectrum-ethanol: λmax=390 nm; ε=29,00 (c=2.10⁻⁵M).

Mass spectrum: molecular peak=535; characteristic fragments: m/e=378 and 379 (scission of the β-lactam).

Proton NMR spectrum (350 MHz, CDCl$_3$, δ in ppm, J in Hz): 1.48 (s, (CH$_3$)$_3$C—OCO—, 9H); 2.89 (s, 6H, (CH$_3$)$_2$N—); 3.17 (AB-type, J=14, 2H, —S—CH$_2$— of the cephem); 5.02 (d, J=4, 1H, H in the 6-position); 5.27 (dd, J=4 and 9, 1H, H in the 7-position); 5.60 (d, J=9, 1H, —OCONH—); 6.71 (d, J=14, 1H, —CH= CH—N<); 6.49 (d, J=14, 1H, —CH=CH—N<); 6.95 (s, 1H, —CH(C$_6$H$_5$)$_2$); 7.2 to 7.5 (b, aromatic, 10H).

The product (2e) can be prepared by esterifying 7-t-butoxycarbonylamino-2-carboxy-3-methyl-8-oxo-5thia-1-azabicyclo[4.2.0]oct-3-ene (product 2f) (3.2 g) with diphenyldiazomethane (2.1 g) at between 25° and 30° C. for 16 hours. After recrystallization from a 90/10 (by volume) cyclohexane/ethyl acetate mixture, a product (2e) (2.3 g) is obtained in the form of white crystals (m.p.=161° C.).

The product (2f) can be prepared by converting 7-t-butoxycarbonylamino-2-methoxycarbonyl-3-methyl-8-oxo-5-thia-1-azabicyclo[4.2.0]oct-2-ene (product 2g) (8.28 g) using the method of R. B. Morin et al., J. Amer. Chem. Soc., 91(6), 1,401 (1969). This yields a product (2f) (5.4 g).

M.p.=200° C. (decomposition) (after recrystallisation from ethyl acetate).

Rf=0.59 [silica gel chromatography plate; eluent: 60/20/1/1 (by volume) ethyl acetate/acetone/water/formic acid mixture].

The product (2g) can be prepared by esterifying 7-t-butoxycarbonylamino-2-carboxy-3-methyl-8-oxo-5-thia-1-azabicyclo[4.2.0]oct-2-ene (product 2h) (16.7 g) with an ether solution of diazomethane according to R. B. Morin et al.; J. Amer. Chem. Soc., 91(6), 1,401 (1969). This yields a product (2g) (13.6 g) in the form of white crystals (m.p.=148° C.).

Rf=0.45 [silica gel chromatography plate; eluent: 60/40 (by volume) cyclohexane/ethyl acetate].

EXAMPLE 3

A solution of 90% pure m-chloroperbenzoic acid (0.464 g) in methylene chloride (10 cc) is added dropwise, over a period of 25 minutes, to a solution, cooled to 0° C., of the syn isomer of 2-benzhydryloxycarbonyl-7-{2-[(2-t-butoxycarbonylprop-2-yl)-oxyimino]-2-(2-tritylaminothiazol-4-yl)-acetamido}-8-oxo-3-(2-tosyloxyvinyl)-5-thia-1-azabicyclo[4.2.0]oct-2-ene (product 3a, mixture containing 75% of the E form and 25% of the Z form) (3 g) in methylene chloride (50 cc). The mixture is stirred for 1 hour at 0° C., diluted with ethyl acetate (500 cc), washed with a 2% strength solution of sodium bicarbonate (2×100 cc), water (2×100 cc) and a saturated aqueous solution of sodium chloride (100 cc), dried over sodium sulphate and filtered and the filtrate is concentrated to dryness at 20° C. under 20 mm Hg (2.7 kPa). The residue is chromatographed on a column of Merck silica gel (0.06–0.2) (60 g) (diameter of the column: 2 cm, height: 20 cm) and elution is carried out with a cyclohexane/ethyl acetate mixture (70/30 by volume) (1 liter), 60 cc fractions being collected. Fractions 5 to 14 are concentrated to dryness at 20° C. under 20 mm Hg (2.7 kPa) and the E form of the syn isomer of 2-benzyhydryloxycarbonyl-7-{2-[(2-t-butoxycarbonylprop-2-yl)-oxyimino]-2-(2-tritylaminothiazol-4-yl)-acetamido}-8-oxo-3-(2-tosyloxyvinyl)-5-thia-1-azabicyclo[4.2.0]oct-2-ene-5-oxide (product 3) (1.9 g) is collected in the form of a hard yellow foam.

Infra-red spectrum (CHBr$_3$), characteristic bands (cm⁻¹): 3,380, 1,800, 1,720, 1,680, 1,590, 1,580, 1,510, 1,490, 1,445, 1,375, 1,190, 1,175, 1,070, 730.

Proton NMR spectrum (350 MHz, d$_6$-DMSO, δ in ppm, J in Hz): 1.37 (s, 9H, —C(CH$_3$)$_3$); 1.45 and 1.46 (2s, 6H, —OC(CH$_3$)$_2$—); 2.44 (s, 3H, —CH$_3$ of the tosyl); 3.60 and 4.41 (2d, J=18, 2H, —SCH$_2$—); 5.06 (d, J=4, 1H, H in the 6-position); 5.96 (dd, J=4 and 9, 1H, H in the 7-position); 6.75 (d, J=13, 1H, —CH=C-HS—); 6.73 (s, 1H, H of the thiazole); 6.93 (s, 1H, —COOCH—); 7.48 and 7.84 (AB-type, 2H, J=9); 8.16 (d, J=9, 1H, —CONH—); 8.73 (s, 1H, —NHC(C$_6$H$_5$)$_3$).

EXAMPLE 4

A solution of para-toluenesulphonic acid (hydrate) (2.2 g) in acetonitrile (15 cc) is added, over a period of 15 minutes, to a solution of the E form of 2-benzhydryloxycarbonyl-7-t-butoxycarbonylamino-3-(2-chlorovinyl)-8-oxo-5-thia-1-azabicyclo[4.2.0]oct-2-ene-5-oxide (3.4 g) in acetonitrile (15 cc) at 40° C. After 30 minutes at 40° C., the reaction mixture is concentrated to dryness under reduced pressure (30 mm Hg; 4 kPa) at 30° C. The residue is taken up in ethyl acetate (100 cc) and the solution obtained is washed with a saturated solution of sodium bicarbonate (2×50 cc) and distilled water (2×50 cc) and then dried over sodium sulphate and concentrated to dryness under reduced pressure (30 mm Hg; 4 kPa) at 35° C. The residue is dried under reduced pressure (0.2 mm Hg; 0.03 kPa) at 25° C. for 1 hour. This yields crude E form of 7-amino-2-benzyhydroxyloxycarbonyl-3-(2-chlorovinyl)-8-oxo-5-thia-1-azabicyclo[4.2.0]oct-2-ene-5-oxide (2.5 g) in the form of a hard orange foam. This product is redissolved in dry methylene chloride (45 cc), a solution of 2-methoxyimino-2-(2-tritylaminothiazol-4-yl)-acetic acid (syn isomer) (2.5 g) and 4-dimethylaminopyridine (0.03 g) in dry methylene chloride (30 cc) is added and N,N'-dicyclohexylcarbodiimide (1.3 g) and dry methylene chloride (10 cc) are then added (after cooling to about 4° C.). The reaction mixture is stirred for 40 minutes at about 6° C. and then for 16 hours at 25° C. The precipitate of N,N'-dicyclohexylurea is filtered off and rinsed with dry methylene chloride (2×5 cc). The combined filtrate and washings are concentrated to dryness under reduced pressure (30 mm Hg; 4 kPa) at 30° C. and the residue obtained is taken up in ethyl acetate (200 cc). The solution obtained is washed successively with 0.2N hydrochloric acid (50 cc), a semi-saturated solution of sodium bicarbonate (2×50 cc) and a saturated solution of sodium chloride (50 cc) and the dried over sodium sulphate. The residue obtained after evaporation to dryness under reduced pressure (30 mm Hg; 4 kPa) at 30° C. is chromatographed on a column of silica (0.04–0.06) (diameter of the column: 4 cm, height: 30 cm), elution being carried out under a pressure of 50 kPa with methylene chloride (800 cc) and then with a mixture of methylene chloride and ethyl acetate (95/5 by volume) (1,200 cc), and 60 cc fractions being collected. Fractions 12 to 25, containing the pure product, are combined and concentrated to dryness under reduced pressure. This yields the E form of the syn isomer of 2-benzyhydryloxycarbonyl-3-(2-chlorovinyl)-7-[2-methoxyimino-2-(2-tritylaminothiazol-4-yl)-acetamido]-8-oxo-5-thia-1-azabicyclo[4.2.0]oct-2-ene-5-oxide (1.7 g) in the form of a hard cream-coloured foam.

Infra-red spectrum (CHBr$_3$), characteristic bands (cm$^{-1}$): 3,380, 2,820, 1,800, 1,725, 1,680, 1,595, 1,585, 1,570, 1,515, 1,495, 1,450, 1,210, 1,040, 930, 750.

Proton NMR spectrum (350 MHz, CDCl$_3$, δ in ppm, J in Hz): 3.22 and 3.92 (2d, J=18, 2H, —S—CH$_2$—); 4.12 (s, 3H, =N—O—CH$_3$); 4.63 (d, J=5, 1H, —H in the 6-position); 6.21 (dd, J=5 and 9, 1H, —H in the 7-position); 6.44 and 7.50 (2d, J=14, 2H, —CH=CHCl); 6.74 (s, 1H, —H of the thiazole); 7.01 (s, 1H, —COO—CH(C$_6$H$_5$)$_2$); 7.11 (b, 1H, —N$\overline{\text{H}}$—C(C$_6$H$_5$)$_3$); 7.2 to 7.6 (m, aromatic); 7.54 (d, J=9, —CO—NH—).

EXAMPLE 5

The syn isomer of 2-[(2-t-butoxycarbonylprop-2-yl)-oxyimino]-2-(2-tritylaminothiazol-4-yl)-acetic acid (prepared in accordance with the process described in Belgian Pat. No. 876,541) (11.66 g) and 4-dimethylaminopyridine (0.1 g) are added to a solution of the E form of 7-amino-2-benzhydryoxycarbonyl-8-oxo-3-(2-tosyloxyvinyl)-5-thia-1-azabicyclo[4.2.0]oct-2-ene-5-oxide (product 5a) (9.84 g) in methylene chloride (170 cc). Dimethylformamide (50 cc) is added in order to obtain a limpid solution, the latter is cooled to between 0° C. and 5° C. and a solution of N,N′-dicyclohexylcarbodiimide (4.21 g) in methylene chloride (50 cc) is added over a period of 15 minutes, whilst stirring. The mixture is stirred for 2 hours at 5° C. and for 2 hours at 20° C. and concentrated at 20° C. under 20 mm Hg (2.7 kPa). The residue is taken up in ethyl acetate (150 cc), the solution is filtered, the filtrate is washed with water (3×100 cc), a semi-saturated aqueous solution of sodium bicarbonate (2×100 cc) and a semi-saturated solution of sodium chloride (2×100 cc), dried over sodium sulphate and filtered and the filtrate is concentrated to dryness at 20° C. under 20 mm Hg (2.7 kPa). The residue is chromatographed on a column of Merck silica gel (0.06–0.2) (400 g) (diameter of the column: 4 cm, height: 76 cm) and elution is carried out with an 80/20 (by volume) cyclohexane/ethyl acetate mixture (1 liter) and a 70/30 mixture (4 liters), 250 cc fractions being collected. Fractions 6 to 11 are concentrated to dryness at 20° C. under 20 mm Hg (2.7 kPa) and the E form of the syn isomer of 2-benzhydryloxycarbonyl-7-{2-[(2-t-butoxycarbonylprop-2-yl)-oxyimino]-2-(2-tritylaminothiazol-4-yl)-acetamido}-8-oxo-3-(2-tosyloxyvinyl)-5-thia-1-azabicyclo[4.2.0]oct-2-ene-5-oxide (product 5) (6.95 g) is collected in the form of a hard yellow foam, the characteristics of which are identical to those of the product of Example 3.

The product (5a) can be obtained in the following manner:

A solution of the E form of 2-benzyhydryloxycarbonyl-7-t-butoxycarbonylamino-8-oxo-3-(2-tosyloxyvinyl)-5-thia-1-azabicyclo[4.2.0]oct-2-ene-5-oxide (product 5b) (54.3 g) and hydrated p-toluenesulphonic acid (30.4 g) in acetonitrile (1.4 liters) is stirred at 35° C. for 2 hours. It is concentrated to dryness at 30° C. under 20 mm Hg (2.7 kPa), the residue is taken up in ethyl acetate (1 liter) and the solution is washed with a semisaturated solution of sodium bicarbonate (2×500 cc) and a semi-saturated solution of sodium chloride (2×500 cc), dried over sodium sulphate and concentrated to dryness at 20° C. under 20 mm Hg (2.7 kPa). The residue is triturated in ether (200 cc). This yields a product (5a) (28.13 g) in the form of a light brown powder.

Rf=0.32, silica gel chromatography plate [85/15 (by volume) methylene chloride/methanol].

The product (5b) can be prepared in the following manner:

A solution of 85% pure m-chloroperbenzoic acid (55.22 g) in methylene chloride (600 cc) is added dropwise, over a period of 2 hours, to a solution, cooled to −10° C., of 2-benzyhydryloxycarbonyl-7-t-butoxycarbonylamino-8-oxo-3-(2-tosyloxyvinyl)-5-thia-b 1-azabicyclo[4.2.0]oct-2-ene (or -3-ene) (product 5c, a mixture of the E and Z forms) (180.56 g) in methylene chloride (1.4 liters). The mixture is washed with a 5% strength solution of sodium bicarbonate (1.5 liters) and water (2×1.5 liters), dried over sodium sulphate and concentrated at 20° C., under reduced pressure (20 mm Hg), to a volume of 300 cc. This solution is chromatographed on a column of Merck silica gel (0.05–0.2) (3 kg) (diameter of the column: 9.2 cm, height: 145 cm). Elution is carried out successively with the following cyclohexane/ethyl acetate mixtures: 80/20 (by volume) (15 liters) and 70/30 (by volume) (32 liters), 600 cc fractions being collected. Fractions 27 and 28 are collected and concentrated to dryness and this yields the Z form of the product (5b) (5.56 g).

Infra-red spectrum (CHBr$_3$), characteristic bands (cm$^{-1}$): 3,420, 1,800, 1,720, 1,505, 1,380, 1,370, 1,195, 1,180, 1,050, 1,010, 730.

Proton NMR spectrum (350 MHz, CDCl$_3$, δ in ppm, J in Hz): 1.49 (s, 9H, —C(CH$_3$)$_3$); 2.44 (s, 3H, —CH$_3$); 3.36 and 4.04 (2d, J=19, 2H, —SCH$_2$—); 4.44 (d, J=4.5, 1H, H in the 6-position); 5.73 (d, J=9, 1H, —CONH—); 5.81 (dd, J=4.5 and 9, 1H, H in the 7-position); 6.42 (d, J=7, 1H, —CH=CHOSO$_2$—); 6.46 (d, J=7, 1H, =CHOSO$_2$—); 6.$\overline{89}$ (s, 1H, —COOCH<); 7.77 (d, J=9, 2H, H in the ortho-position of the tosyl).

A mixture of the Z and E forms (26 g) is obtained from fractions 29 to 34.

Finally, the E form of the product (5b) (43 g) is obtained from fractions 35 to 58.

Infra-red spectrum (CHBr$_3$), characteristic bands (cm$^{-1}$): 3,420, 1,800, 1,720, 1,505, 1,380, 1,370, 1,195, 1,180, 1,075, 935, 745.

Proton NMR spectrum (350 MHz, CDCl$_3$, δ in ppm, J in Hz): 1.48 (s, 9H, (CH$_3$)$_3$C—); 2.46 (s, 3H, —CH$_3$); 3.16 and 3.81 (2d, J=18, 2H, —SCH$_2$—); 4.46 (d, J=4.5, 1H, H in the 6-position); 5.73 (d, J=9, 1H, —CONH—); 5.8 (dd, J=9 and 4.5, 1H, H in the 7-position); 6.83 (d, J=13, 1H, —CH=CHOSO$_2$—); 6.83 (s, 1H, —COOCH<); 7.08 (d, J=13, 1H, =CHOSO$_2$—); 7.73 (d, J=9, 2H, H in the ortho-position of the tosyl).

The product (5c), which is a mixture of the E and Z forms, can be obtained in the following manner:

A solution of formic acid (50 cc) in water (500 cc) is added to a solution of 2-benzhydryloxycarbonyl-7-t-butoxycarbonylamino-3-(2-dimethylaminovinyl)-8-oxo-5-thia-1-azabicyclo[4.2.0]oct-2-ene (E form) (product 5d) (113.7 g) in tetrahydrofuran (1 liter). The homogeneous solution is stirred at 20° C. for 20 minutes and then concentrated to a quarter of its volume under reduced pressure (20 mm Hg) at 20° C. The concentrate is taken up in ethyl acetate (2 liters), the solution is washed with a 5% strength solution of sodium bicarbonate (2×500 cc), water (2×500 cc) and a saturated solution of sodium chloride (2×500 cc), dried over sodium sulphate and filtered and the filtrate is evaporated to dryness at 20° C. under reduced pressure (20 mm Hg). A crude product (112.4 g) is collected and this is treated, in solution in anhydrous pyridine (250 cc), at 5° C., with tosyl chloride (57.2 g). After 30 minutes at 5° C. and 1 hour at 20° C., the solution is poured into a water/crushed ice mixture (1 liter). The aqueous phase is separated off and the insoluble material is washed with distilled water (300 cc). The pasty product is dissolved in ethyl acetate (200 cc) and the solution is washed with 1N hydrochloric acid (2×750 cc), a 5% strength solution of sodium bicarbonate (2×750 cc) and water (4×750 cc), dried over sodium sulphate and concentrated to dryness under reduced pressure (20 mm Hg) at 20° C. This yields a product (121 g), consisting mainly of a product (5c) (a mixture of the E and Z forms), in the form of a crude, hard brown foam.

The product (5d) is prepared as described above in Example 2 for the product (2d).

EXAMPLE 6

A solution of the E form of 2-benzhydryloxycarbonyl-7-t-butoxycarbonylamino-3-(2-chlorovinyl)-8-oxo-5-thia-1-azabicyclo[4.2.0]oct-2-ene-5-oxide (6 g) in methylene chloride (150 cc) and dimethylacetamide (4.06 cc) is cooled to −10° C., and a solution of phosphorus trichloride (2.02 g) in methylene chloride (15 cc) is added, over a period of 5 minutes and with stirring. The mixture is stirred for a further 30 minutes and it is concentrated to dryness at 30° C. under 20 mm Hg (2.7 kPa). The residue is diluted with ethyl acetate (250 cc), the organic phase is washed with a saturated solution of sodium bicarbonate (2×200 cc), dried over magnesium sulphate and filtered and the filtrate is concentrated to dryness at 30° C. under 20 mm Hg (2.7 kPa). The residue is chromatographed on a column of Merck silica gel (0.06–0.2) (60 g) (diameter of the column: 3 cm), elution being carried out with an ethyl acetate/cyclohexane mixture (30/70 by volume) and 60 cc fractions being collected. Fractions 2 to 4 are concentrated to dryness under reduced pressure and the E form of 2-benzhydryloxycarbonyl-7-t-butoxycarbonylamino-3-(2-chlorovinyl)-8-oxo-5-thia-1-azabicyclo[4.2.0]oct-2-ene is collected in the form of a hard yellow foam.

Rf=0.47, silica gel chromatography plate [30/70 (by volume) ethyl acetate/cyclohexane]

EXAMPLE 7

Methanesulphonic acid (4.1 cc) is added, over a period of 30 seconds, to a solution of the E form of 2-benzyhydryloxycarbonyl-7-t-butoxycarbonylamino-3-(2-chlorovinyl)-8-oxo-5-thia-1-azabicyclo[4.2.0]oct-2-ene (4.1 g) in acetonitrile (41 cc) and the mixture is stirred for a further 5 minutes at 20° C. The mixture is then poured into a saturated solution of sodium bicarbonate (200 cc), then water (250 cc) is added and the mixture is extracted with methylene chloride (200 cc). The organic phase is decanted, dried over magnesium sulphate and filtered and the filtrate is concentrated to a volume of 100 cc at 25° C. under 30 mm Hg (4 kPa). This yields a solution of 7-amino-2-benzhydryloxycarbonyl-3-(2-chlorovinyl)-8-oxo-5-thia-1-azabicyclo[4.2.0]oct-2-ene, which is reacted with D-α-t-butyloxycarbonylaminophenylacetic acid (1.95 g) in the presence of dicyclohexylcarbodiimide (1.9 g) at 4° C. for 90 minutes. The reaction mixture is then filtered to remove the precipitated dicylohexylurea, the filtrate is concentrated to dryness at 30° C. under 20 mm Hg (2.7 kPa) and the residue is chromatographed on a column of silica gel (0.04–0.06) (diameter of the column: 3.5 cm, height: 25 cm) and elution is carried out with an ethyl acetate/cyclohexane mixture (35/65 by volume), 100 cc fractions being collected. Fractions 4 to 6, containing the product, are concentrated to dryness at 30° C. under 20 mm Hg (2.7 kPa). This yields the E form of 7-D-α-t-butoxycarbonylaminophenylacetamido-2-benzhydryloxycarbonyl-3-(2-chlorovinyl)-8-oxo-5-thia-1-azabicyclo[4.2.0]oct-2-ene (2.1 g) in the form of a hard yellow foam.

Rf=0.50, silica gel chromatography plate [40/60 (by volume) ethylacetate/cyclohexane].

Proton NMR spectrum (250 MHz, CDCl$_3$, δ in ppm, J in Hz): 1.42 (s, 9H, —C(CH$_3$)$_3$); 3.39 (s, 2H, —SCH$_2$—); 4.93 (d, J=4, 1H, H in the 6-position); 5.21 (m, 1H, —CONHCH<); 5.60 (d, J=6, 1H, —CONH CH<); 5.80 (dd, J=4, and 9, 1H, H in the 7-position); 6.37 (d, J=14, 1H, trans —CH=).

The E form of 2-benzhydryloxycarbonyl-7-D-α-t-butoxycarbonylaminophenylacetamido-3-(2-chlorovinyl)-8-oxo-5-thia-1-azabicyclo[4.2.0]oct-2-ene (2.1 g) is dissolved in anisole (5 cc) and trifluoroacetic acid (25 cc) at 20° C. The yellow solution is immediately concentrated to dryness at 30° C. under reduced pressure (2 mm Hg; 270 Pa). The residue is dissolved in ethylacetate (15 cc) and the solution is poured in isopropylether (200 cc), whilst stirring. The precipitate is filtered off and dried at 25° C. under 2 mm Hg (270 Pa) and the E form of 7-D-α-aminophenylacetamido-2-carboxy-3-(2-chlorovinyl)-8-oxo-5-thia-1-azabicyclo[4.2.0]oct-2-ene trifluoroacetate (1.5 g) is obtained in the form of a whitish solid.

Rf=0.32, silica gel chromatography plate [6/1/1 (by volume) ethyl acetate/formic acid/water].

Proton NMR spectrum (250 MHz, d$_6$-DMSO, δ in ppm, J in Hz): 3.46 (s broad, 2H, —SCH$_2$—); 4.95 (d, J=4, 1H, H in the 6-position); 5.10 (s, 1H, >CHNH$_2$); 5.72 (dd, J=4 and 7,5, 1H, H in the 7-position); 6.51 and 7.29 (2d, J=14, 2H, trans —CH=CH—); 9.57 (d, J=7.5, 1H, —CONH—).

B. The dihalogen intermediates of the products according to the invention can be isolated in the following manner:

EXAMPLE 8

Following the procedure described in Example 2, a solution of the syn isomer of 2-benzyhydryloxycarbonyl-7-[2-methoxyimino-2-(2-tritylaminothiazol-4-yl)-acetamido]-8-oxo-3-(2-oxoethyl)-5-thia-1-azabicyclo[4.2.0]oct-2-ene (product 8a) (2.3 g) in methylene chloride (15 cc), cooled to −40° C., is treated with a 0.5M solution of the chlorine/triphenyl phosphite addition compound in methylene chloride (5.5 cc). The reaction mixture is stirred for 3 hours at a temperature between −40° C. and −20° C. and then diluted with ethyl acetate (200 cc). The decanted organic solution is washed with a semi-saturated solution of sodium bicarbonate and of sodium chloride (50 cc) and then with a saturated solution of sodium chloride (3×50 cc). The aqueous phases are reextracted with ethyl acetate (50 cc) and the combined organic solutions are concentrated to dryness under reduced pressure (30 mm Hg; 4 kPa) at 30° C. The residue is stirred for 16 hours with isopropyl ether (150 cc). The precipitate is filtered off and washed with isopropyl ether (50 cc) and then redissolved in methylene chloride (50 cc) and fixed to silica gel (0.2–0.06) (8 g) which is deposited onto a column of silica gel (0.06–0.04) (diameter of the column: 1.8 cm, height: 35 cm). Elution is carried out under a pressure of 80 kPa with a mixture of cyclohexane and ethyl acetate (75/25 by volume), 50 cc fractions being collected. Fractions 5 to 7, containing the pure product, are combined and concentrated to dryness under reduced pressure (30 mm Hg; 4 kPa) at 30° C. This yields the syn isomer of 2-benzhydryloxycarbonyl-3-(2,2-dichloroethyl)-7-[2-methoxyimino-2-(2-tritylaminothiazol-4-yl)-acetamido]-8-oxo-5-thia-1-azabicyclo[4.2.0]oct-2-ene (product 8b) (0.25 g) in the form of a whitish solid.

Proton NMR spectrum (350 MHz, CDCl₃, δ in ppm, J in Hz): 3.17+3.33 (2dd, J=14 and 9+J=14 and 5, 2H, exo—CH₂); 3.62 (limiting AB-type, J=18, 2H, —CH₂—S—); 4.08 (s, 3H, =N—O—CH₃); 5.06 (d, J=5, 1H, —H in the 6-position); 5.94 to 6 (m, 2H, —H in the 7-position and —CHCl₂); 6.76 (s, 1H, —H of the thiazole); 6.8 (d, J=9, 1H, —CO—NH—); 6.92 (s, 1H, —COO—C$\underline{H}$(C₆H₅)₂); 7.04 (b, 1H, —N$\underline{H}$—C(C₆H₅)₃); 7.15 to 7.5 (m, aromatic).

A solution of meta-chloroperbenzoic acid (85% pure) (0.05 g) in methylene chloride (1 cc) is added all at once to a solution, cooled to −10° C., of product (8b) (0.2 g) in methylene chloride (5 cc). After 30 minutes at −10° C., the reaction mixture is diluted with ethyl acetate (20 cc) and washed with a saturated solution of sodium bicarbonate (2×10 cc) and a saturated solution of sodium chloride (2×10 cc). After the mixture has been dried over sodium sulphate and concentrated to dryness under reduced pressure (30 mm Hg; 4 kPa) at 30° C., crude syn isomer of 2-benzhydryloxycarbonyl-3-(2,2-dichloroethyl)-7-[2-methoxyimino-2-(2-tritylaminothiazol-4-yl)-acetamido]-8-oxo-5-thia-1-azabicyclo[4.2.0]oct-2-ene-5-oxide (product 8) (0.15 g) is obtained in the form of a hard orange foam.

Proton NMR spectrum (350 MHz, CDCl₃, δ in ppm, J in Hz): 3.14+3.56 (2dd, J=15 and 5+J=15 and 7, 2H, exo—CH₂); 3.39 and 3.96 (2d, J=18, 2H,

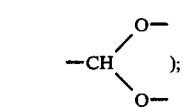

4.09 (s, 3H, =N—O—CH₃); 4.58 (d, J=5, 1H, —H in the 6-position); 5.87 (dd, J=5 and 7, 1H, —CHCl₂); 6.19 (dd, J=5 and 9, 1H, —H in the 7-position); 6.72 (s, 1H, —H of the thiazole); 6.94 (s, 1H, —COO—C$\underline{H}$(C₆H₅)₂); 7.08 (b, 1H, —N$\underline{H}$—C(C₆H₅)₃); 7.10 to 7.60 (m, aromatic+—CO—N$\underline{H}$).

REFERENCE EXAMPLE 1

The product of Example 3 can be used in the following manner:

A mixture of the E form of the syn isomer of 2-benzhydryloxycarbonyl-7-{2-[(2-t-butoxycarbonylprop-2-yl)-oxyimino]-2-(2-tritylaminothiazol-4-yl)-acetamido}-8-oxo-3-(2-tosyloxyvinyl)-5-thia-1-azabicyclo[4.2.0]oct-2-ene-5-oxide (product 1A) (6.79 g), dimethylformamide (60 cc), 4-(2,2-dimethoxyethyl)-5,6-dioxo-3-thioxo-perhydro-1,2,4-triazine (1.68 g) and N,N-diisopropylethylamine (1.25 cc) is heated at 60° C. for 4 hours, whilst stirring and under nitrogen. The residue obtained after this treatment is chromatographed on a column of Merck silica gel (0.06–0.2) (125 g) (diameter of the column: 3 cm, height: 43 cm). Elution is carried out with a 50/50 (by volume) cyclohexane/ethyl acetate mixture (1.5 liters) and ethyl acetate (1 liter), 100 cc fractions being collected. Fractions 16 to 21 are concentrated to dryness at 25° C. under 20 mm Hg (2.7 kPa) and this yields the E form of the syn isomer of 2-benzhydryloxycarbonyl-7-{2-[(2-t-butoxycarbonylprop-2-yl)-oxyimino]-2-(2-tritylaminothiazol-4-yl)-acetamido}-3-{2-[4-(2,2-dimethoxyethyl)-5,6-dioxo-1,4,5,6-tetrahydro-1,2,4-triazin-3-yl]-thiovinyl}-8-oxo-5-thia-1-azabicyclo[4.2.0]oct-2-ene-5-oxide (product 1B) (5.5 g) in the form of a hard brown foam.

Infra-red spectrum (CHBr₃), characteristic bands (cm⁻¹): 1,800, 1,720, 1,690, 1,585, 1,510, 1,495, 1,445, 1,370, 1,080, 1,060, 1,040, 940, 750, 700.

Proton NMR spectrum (350 MHz, d₆-DMSO, δ in ppm, J in Hz): 1.35 (s, 9H, —C(CH₃)₃); 1.44 and 1.45 (2s, 6H, =N—O—C(CH₃)₂—); 3.32 (s, 6H, (—OCH₃)₂); 3.65 and 4.36 (2d, J=18, 2H, —S—CH₂—); 3.95 (d, J=5, 2H, >N—CH₂—); 4.56 (t, J=5, 1H,

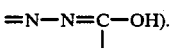

5.09 (d, J=5, 1H, —H in the 6-position); 5.95 (dd, J=5 and 9, 1H, —H in the 7-position); 6.78 (s, 1H, —H of the thiazole); 7 (s, 1H, —COO—C$\underline{H}$(C₆H₅)₂); 7.02 and 7.1 (2d, J=16, 2H, —CH=CH—S—); 8.23 (d, J=9, 1H, —CO—NH—); 8.73 (s, 1H, —N$\underline{H}$—C(C₆H₅)₃); 12.65 (s, 1H, =N—NH—CO— or

=N—N=C—OH).
       |

A solution of product (1B) (5.37 g) in methylene chloride (45 cc) and N,N-dimethylacetamide (1.79 cc) is treated with phosphorus trichloride (0.79 cc), at −5° C., for 1½ hours, whilst stirring. The residue obtained after treatment is chromatographed on a column of Merck silica gel (0.06–0.2) (80 g) (diameter of the column: 2 cm, height: 20 cm) and elution is carried out with a 40/60 (by volume) cyclohexane/ethyl acetate mixture (250 cc) and a 30/70 mixture (1.5 liters), 100 cc fractions being collected. Fractions 5 to 14 are concentrated to dryness at 25° C. under 20 mm Hg and this yields the E form of the syn isomer of 2-benzhydryloxycarbonyl-7-{2-[(2-t-butoxycarbonylprop-2-yl)-oxyimino]-2-(2-tritylaminothiazol-4-yl)-acetamido}-3-{2-[4-(2,2-dimethoxyethyl)-5,6-dioxo-1,4,5,6-tetrahydro-1,2,4-triazin-3-yl]-thiovinyl}-8-oxo-5-thia-1-azabicyclo[4.2.0]oct-2-ene (product 1C) (4.02 g) in the form of a hard, light brown foam.

Infra-red spectrum (KBr), characteristic bands (cm⁻¹): 1,790, 1,720, 1,690, 1,585, 1,520, 1,495, 1,450, 1,370, 1,080, 940, 750, 700.

Proton NMR spectrum (350 MHz, d₆-DMSO, δ in ppm, J in Hz): 1.37 (s, 9H, —C(CH₃)₃); 1.42 (s, 6H, =N—O—C(CH₃)₂—); 3.31 (s, 6H, (—OCH₃)₂); 3.64 and 3.89 (2d, J=18, 2H, —S—CH₂—); 3.95 (d, J=5, 2H, >N—CH₂—); 4.56 (t, J=5, 1H,

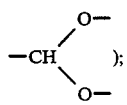

5.26 (d, J=4, 1H, —H in the 6-position); 5.77 (dd, J=4 and 9, 1H, —H in the 7-position); 6.71 (s, 1H, —H of the thiazole); 6.90 and 7.03 (2d, J=16, 2H, —CH=CH—S—); 6.97 (s, 1H, —COO—C$\underline{H}$(C₆H₅)₂); 8.80 (s, 1H, —NH—C(C₆H₅)₃); 9.39 (d, J=9, 1H, —CO—NH—); 12.66 (s, 1H, =N—NH—CO— or

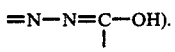

A solution of product (1C) (3.89 g) in trifluoroacetic acid (39 cc) is stirred at 20° C. for 20 minutes. It is concentrated to dryness at 20° C. under 0.05 mm Hg (0.007 kPa), the residue is taken up in diethyl ether (100 cc) and the solution is stirred for 10 minutes and filtered. The solid obtained is treated with formic acid (80 cc), at 50° C., for 45 minutes, water (16 cc) is added and the mixture is kept at 50° C. for 30 minutes and concentrated to dryness at 20° C. under 0.05 mm Hg (0.007 kPa). The residue is taken up in acetone (3×150 cc), each solution being evaporated at 20° C. under 30 mm Hg (4 kPa), and the residue is heated under reflux in acetone (100 cc), whilst stirring. The mixture is filtered and the E form of the syn isomer of 7-{2-(2-aminothiazol-4-yl)-2-[(2-carboxyprop-2-yl)-oxyimino]-acetamido}-2-carboxy-3-[2-(5,6-dioxo-4-formylmethyl-1,4,5,6-tetrahydro-1,2,4-triazin-3-yl)-thiovinyl]-8-oxo-5-thia-1-azabicyclo[4.2.0]oct-2-ene (product R1) (2.15 g) is collected in the form of a yellow powder.

Infra-red spectrum (KBr), characteristic bands (cm⁻¹): 3,400, 3,300, 3,200, 2,200, 1,780, 1,720, 1,685, 1,585, 1,540, 1,000.

Proton NMR spectrum (350 MHz, CF₃COOD, δ in ppm, J in Hz): 1.85 and 1.86 (2s, 6H, —CH₃); 3.90 (s broad, 2H, —SCH₂—); 5.20 (s, 2H, —CH₂CHO); 5.40 (d, J=4, 1H, H in the 6-position); 6.12 (d, J=4, 1H, H in the 7-position); 7.23 and 7.76 (2d, J=16, 2H, —CH=CH—); 7.50 (s, 1H, H of the thiazole); 9.73 (s, 1H, —CHO).

REFERENCE EXAMPLE 2

The product of Example 2 can be used in the following manner:

A solution of the E form of 2-benzhydryloxycarbonyl-7-t-butoxycarbonylamino-3-(2-chlorovinyl)-8-oxo-5-thia-1-azabicyclo[4.2.0]oct-2-ene-5-oxide (product 2A) (0.54 g), 4-(2,2-dimethoxyethyl)-5,6-dioxo-3-thioxo-perhydro-1,2,4-triazine (0.25 g) and N,N-diisopropylethylamine (0.19 cc) in dry N,N-dimethylformamide (8 cc) is heated at 60° C. for 4 hours and then stirred at 25° C. for 16 hours and diluted with methylene chloride (100 cc). The solution is washed successively with a semi-saturated solution of sodium chloride (2×50 cc), a semi-saturated solution of sodium bicarbonate (2×50 cc) and distilled water (2×50 cc). After the organic layer has been dried over sodium sulphate and concentrated to dryness under reduced pressure (30 mm Hg; 4 kPa) at 35° C., the residue is chromatographed on a column of silica gel (0.04–0.06) diameter of the column: 2 cm, height: 30 cm), elution being carried out under 50 kPa with ethyl acetate and 30 cc fractions being collected. Fractions 12 to 16 are combined and concentrated to dryness under reduced pressure (30 mm Hg; 4 kPa) at 35° C. This yields a product (2B) (0.4 g) in the form of an amorphous orange solid. This product is crystallized from a mixture of isopropyl ether and acetonitrile (75/25 by volume) (20 cc). This yields the crystalline product (0.15 g), the characteristics of which are as follows:

Infra-red spectrum (KBr), characteristic bands (cm⁻¹): 3,410, 1,790, 1,715, 1,580, 1,490, 1,450, 1,155, 1,115, 1,075, 1,040, 936, 750, 740, 695.

Proton NMR spectrum (80 MHz, d₆-DMSO, δ in ppm, J in Hz): 1.45 (s, 9H, (CH₃)₃C—); 3.62 and 4.42 (2d, J=18.5, 2H, —S(O)CH₂—); 3.33 (s, 6H, —CH(OCH₃)₂); 3.97 (d, J=5, 2H, —CH₂CH(OCH₃)₂); 4.55 (t, J=5, 1H, —CH(OCH₃)₂); 5.04 (d, J=4, 1H, H in the 6-position); 5.80 (dd, J=4 and 9, 1H, H in the 7-position); 6.40 (d, J=9, CONH—C₇); 6.98 (s, 1H, —CH(C₆H₅)₂); 7.08 (limiting AB-type, 2H, —CH=CH—S—); 7.2 to 7.50 (m, 10H, aromatic); 12.68 (s, 1H,

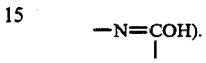

The E form of 2-benzhydryloxycarbonyl-7-t-butoxycarbonylamino-3-{2-[4-(2,2-dimethoxyethyl)-5,6-dioxo-1,4,5,6-tetrahydro-1,2,4-triazin-3-yl]-thiovinyl}-8-oxo-5-thia-1-azabicyclo[4.2.0]oct-2-ene-5-oxide (product 2B) (5 g) is added to an acetonitrile/methanol mixture (85/15 by volume) (80 cc), and methanesulphonic acid (6 g) is then added. The mixture has become limpid. It is stirred for 5 hours at 20° C. and the white precipitate formed is filtered off. The precipitate is washed with acetonitrile (2×10 cc), ethyl acetate (2×25 cc) and then ethyl ether (2×25 cc). After drying in vacuo (0.5 mm Hg; 0.07 KPa), the methanesulfonate of the product (2C) (4.4 g) is obtained in the form of white crystals.

Infra-red spectrum (KBr), characteristic bands (cm⁻¹): 3,300, 2,200, 1,800, 1,720, 1,590, 1,495, 1,455, 1,220, 1,125, 1,085, 1,080, 1,045, 945, 760, 710, 620, 600, 560.

Proton NMR spectrum (80 MHz, d₆-DMSO, δ in ppm, J in Hz): 2.48 (s, 3H, CH₃SO₃H); 3.38 (s, 6H, (—OCH₃)₂); 3.74 and 4.45 (2d, J=18, 2H, —SCH₂—); 3.98 (d, J=5, 2H, >NCH₂—); 4.58 (t, J=5, 1H, CH(OCH₃)₂); 5.06 (d, J=4, 1H, H in the 6-position); 5.38 (d, J=4, 1H, H in the 7-position); 7.0 (s, 1H, —COOCH<).

A mixture of the E form of 7-amino-2-benzhydryloxycarbonyl-3-{2-[4-(2,2-dimethoxyethyl)-5,6-dioxo-1,4,5,6-tetrahydro-1,2,4-triazin-3-yl]-thiovinyl}-8-oxo-5-thia-1-azabicyclo[4.2.0]oct-2-ene-5-oxide methanesulphonate (product 2C) (0.14 g), methylene chloride (30 cc) and a semi-saturated solution of sodium bicarbonate (10 cc) is stirred for 10 minutes at 20° C. and the organic phase is decanted, washed with a saturated solution of sodium chloride (15 cc), dried over sodium sulphate and filtered. The filtered solution is treated with the syn isomer of 2-t-butoxycarbonylmethoxyimino-2-(2-tritylaminothiazol-4-yl)-acetic acid (prepared according to Belgian Pat. No. 865,298) (0.156 g) and 4-dimethylaminopyridine (5 mg.). The mixture is cooled to 5° C., a solution of N,N'-dicyclohexylcarbodiimide (50 mg) in methylene chloride (1 cc) is added dropwise over a period of 3 minutes, and the temperature is left to rise to 20° C. over a period of 3 hours. The mixture is washed with a 2% strength solution of sodium bicarbonate (20 cc) and a semi-saturated solution of sodium chloride (20 cc), dried over sodium sulphate and filtered and the filtrate is concentrated to dryness at 20° C. under 20 mm Hg (2.7 kPa). The residue is chromatographed on a column of Merck silica gel (0.04–0.06) (diameter of the column: 1.8 cm, height: 9 cm); elution is carried out with a 20/80 (by volume) cyclohexane/ethyl acetate mixture (200 cc) under a pressure of 40 kPa, 10 cc fractions being collected. Fractions 6 to 14 are concentrated to dryness at 20° C. under 20 mm Hg (2.7 kPa) and the E form of the syn isomer of 2-benzhydryloxycarbonyl-7-[2-t-butoxycarbonylmethoxyimino-2-(2-tritylaminothiazol-4-yl)-acetamido]-3-{2-[4-(2,2-dimethoxyethyl)-5,6-dioxo-1,4,5,6-tetrahydro-1,2,4-triazin-3-yl]-thiovinyl}-8-oxo-5-thia-1-azabicyclo[4.2.0]oct-2-ene-5-oxide (product 2D) (50 mg) is collected in the form of a hard cream-coloured foam, the infra-red and NMR characteristics of which are as follows:

Infra-red spectrum (CHBr$_3$), characteristic bands (cm$^{-1}$): 1,800, 1,720, 1,690, 1,590, 1,520, 1,495, 1,450, 1,370, 1,080, 1,065, 1,040, 945, 755, 700.

Proton NMR spectrum (350 MHz, d$_6$-DMSO, δ in ppm, J in Hz): 1.40 (s, 9H, —C(CH$_3$)$_3$); 3.24 (s, 6H, (—OCH$_3$)$_2$); 3.60 and 4.25 (2d, J=18, 2H, —SCH$_2$—); 3.95 (d, J=6, 2H, >NCH$_2$—); 4.52 (s, 2H, =NOCH$_2$—); 4.54 (t, J=6, 1H, —CH(OCH$_3$)$_2$); 5.08 (d, J=4, 1H, H in the 6-position); 5.91 (dd, J=4 and 9, 1H, H in the 7-position); 6.82 (s, 1H, H of the thiazole); 6.97 (s, 1H, —COOCH<); 6.96 and 7.0 (2d, J=16, 2H, —CH=CH—); 8.68 (d, J=9, 1H, —CONH—); 8.74 (s, 1H, —NH C(C$_6$H$_5$)$_3$); 12.35 (s, 1H, =NNHCO— or

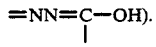

A solution of product (2D) (12.7 g) in methylene chloride (100 cc) and N,N-dimethylacetamide (4.34 cc) is treated with phosphorus trichloride (1.91 cc), at −5° C., for 1 hour 15 minutes, whilst stirring. The mixture is diluted with ethyl acetate (600 cc), washed with a 2% strength solution of sodium bicarbonate (2×200 cc) and a semi-saturated solution of sodium chloride (2×200 cc), dried over sodium sulphate and filtered and the filtrate is concentrated to dryness at 30° C. under 20 mm Hg (2.7 kPa). The product, dissolved in methylene chloride (50 cc), is fixed to Merck silica gel (0.06–0.2) (25 g) and the powder obtained is deposited on a column of silica gel (175 g) (diameter of the column: 3 cm, height: 60 cm). Elution is carried out with a 60/40 (by volume) cyclohexane/ethyl acetate mixture (1.2 liters) and then with a 40/60 (by volume) mixture (2.8 liters), 100 cc fractions being collected. Fractions 13 to 28 are combined and evaporated to dryness at 20° C. under 20 mm Hg (2.7 kPa) and this yields the E form of the syn isomer of 2-benzhydryloxycarbonyl-7-[2-t-butoxycarbonyl methoxyimino-2-(2-tritylaminothiazol-4-yl)-acetamido]-3-{2-[4-(2,2-dimethoxyethyl)-5,6-dioxo-1,4,5,6-tetrahydro-1,2,4-triazin-3-yl]-thiovinyl}-8-oxo-5-thia-1-azabicyclo[4.2.0]oct-2-ene (9.45 g) in the form of a hard yellow-orange foam (product 2E).

Infra-red spectrum (CHBr$_3$), characteristic bands, (cm$^{-1}$): 3,280, 1,800, 1,725, 1,690, 1,590, 1,530, 1,495, 1,440, 1,370, 1,160, 1,080, 945, 755, 700.

Proton NMR spectrum (350 MHz, d$_6$-DMSO, δ in ppm, J in Hz): 1.45 (s, 9H, —C(CH$_3$)$_3$); 3.25 (s, 6H, (—OCH$_3$)$_2$); 3.63 and 3.81 (2d, J=18, 2H, —SCH$_2$—); 3.95 (d, J=6, 2H, <NCH$_2$—); 4.52 (s, 2H, =NOCH$_2$—); 4.57 (t, J=6, 1H, —CH(OCH$_3$)$_2$); 5.24 (d, J=4, 1H, H in the 6-position); 5.78 (dd, J=4 and 9, 1H, H in the 7-position); 6.78 (s, 1H, H of the thiazole); 6.95 (s, 1H, —COOCH<); 6.93 and 7.0 (2d, J=16, 2H, —CH=CH—); 8.80 (s, 1H, —NHC(C$_6$H$_5$)$_3$); 9.50 (d, J=9, 1H, —CONH—); 12.62 (s, 1H, =NNHCO— or

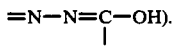

A solution of product (2E) (9.4 g) in trifluoroacetic acid (95 cc) is stirred at 20° C. for 25 minutes and concentrated to dryness at 20° C. under 0.05 mm Hg (0.007 kPa). The residue is triturated in diethyl ether (200 cc), the suspension is filtered and a yellow powder (6.7 g) is obtained. The product thus obtained is dissolved in pure formic acid (190 cc) and the solution is heated at 50° C. for 40 minutes and concentrated to dryness at 30° C. under 0.05 mm Hg (0.007 kPa). The residue is taken up in acetone (200 cc), the solution is concentrated to dryness at 20° C. under 30 mm Hg (4 kPa) and the operation is repeated a second time. The solid obtained is treated with acetone (300 cc) under reflux for 15 minutes, the mixture is filtered hot and, after drying, the E form of the syn isomer of 7-[2-(2-aminothiazol-4-yl)-2-carboxymethoxyiminoacetamido]-2-carboxy-3-[2-(5,6-dioxo-4-formylmethyl-1,4,5,6-tetrahydro-1,2,4 -triazin-3-yl)-thiovinyl]-8-oxo-5-thia-1-azabicyclo[4.2.0]oct-2-ene (product R2) (4.45 g) is obtained in the form of a yellow powder.

Infra-red spectrum (KBr), characteristic bands (cm$^{-1}$): 3,600, 2,200, 1,775, 1,815, 1,680, 1,635, 1,585, 1,195, 945, 800, 720.

Proton NMR spectrum (350 MHz, CF$_3$COOD, δ in ppm, J in Hz): 3.88 (s, broad, 2H, —SCH$_2$—); 5.12 (s, 2H, =NOCH$_2$—); 5.21 (s, 2H, —CH$_2$CHO); 5.39 (d, J=4, 1H, H in the 6-position); 6.10 (d, J=4, 1H, H in the 7-position); 7.24 and 7.75 (2d, J=16, 2H, —CH=CH—); 7.52 (s, 1H, H of the thiazole); 9.77 (s, 1H, —CHO).

REFERENCE EXAMPLE 3

The product of Example 4 can be used in the following manner:

A solution of the E form of the syn isomer of 2-benzhydryloxycarbonyl-3-(2-chlorovinyl)-7-[2-methoxyimino-2-(2-tritylaminothiazol-4-yl)-acetamido]-8-oxo-5-thia-1-azabicyclo[4.2.0]oct-2-ene-5-oxide (product 3A) (0.9 g), 1-(2,2-diethoxyethyl)-5,6-dioxo-4-methyl-3-thioxo-perhydro-1,2,4-triazine (0.23 g) and N,N-diisopropylethylamine (0.19 cc) in N,N-dimethylformamide (10 cc) is stirred for 16 hours at 25° C. and then for 4 hours at 60° C. and is then cooled and diluted with methylene chloride (100 cc). The solution obtained is washed successively with a saturated solution of sodium chloride (2×50 cc), a saturated solution of sodium bicarbonate (2×50 cc) and distilled water (2×50 cc) and then dried over sodium sulphate and concentrated to dryness under reduced pressure (30 mm Hg; 4 kPa) at 30° C. The residue is chromatographed on a column of silica gel (0.04–0.06) (diameter of the column: 3 cm, height: 30 cm), elution being carried out under a pressure of 50 kPa with a mixture of cyclohexane and ethyl acetate (25/75 by volume) (2.5 liters) and 50 cc fractions being collected. Fractions 19 to 42, containing the pure product, are combined and concentrated to dryness. This yields the E form of the syn isomer of 2-benzhydryloxycarbonyl-3-{2-[1-(2,2-diethoxyethyl)-5,6-dioxo-4-methyl-1,4,5,6-tetrahydro-1,2,4-triazin-3-yl]-thiovinyl}-7-[2-methoxyimino-2-(2-tritylaminothiazol-4-yl)-acetamido]-8-oxo-5-thia-1-azabicyclo[4.2.0]oct-2-ene-5-oxide (product 3B) (0.8 g) in the form of a hard orange foam, the characteristics of which are as follows:

Infra-red spectrum (CHBr₃), characteristic bands (cm⁻¹): 3,380, 2,820, 1,800, 1,715, 1,680, 1,585, 1,515, 1,495, 1,445, 1,050, 940, 750.

Proton NMR spectrum (350 MHz, d₆-DMSO, δ in ppm, J in Hz): 1.07 and 1.08 (2t, J=7, 6H, 2—CH₃); 3.28 (s, >N—CH₃); 3.40 to 3.70 (2m, 4H, (O—CH₂—CH₃)₂); 3.62 and 4.36 (2d, J=18, 2H, —S—CH₂—); 3.85 (s, 3H, =N—OCH₃); 3.95 (limiting AB-type, 2H, >N—CH₂—); 4.85 (t, J=6, 1H,

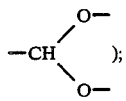

5.08 (d, J=4, 1H, —H in the 6-position); 5.87 (dd, J=4 and 9, 1H, —H in the 7-position); 6.80 (s, 1H, —H of the thiazole); 6.99 (s, 1H, —COO—CH(C₆H₅)₂); 7.05 and 7.18 (2d, J=16, 2H, —CH=CH—S—); 8.79 (s, 1H, —NH—C(C₆H₅)₃); 9.12 (d, J=9, 1H, —CO—NH—).

Rf=0.3, Merck silica gel chromatography plate [eluent: 20/80 by volume mixture of cyclohexane and ethyl acetate].

Product (3B) (2.3 g) is treated with phosphorus trichloride (0.44 cc), at −5° C., for 1 hour 15 minutes. This yields the E form of the syn isomer of 2-benzhydryloxycarbonyl-3-{2-[1-(2,2-diethoxyethyl)-5,6-dioxo-4-methyl-1,4,5,6-tetrahydro-1,2,4-triazin-3-yl]-thiovinyl}-7-[2-methoxyimino-2-(2-tritylaminothiazol-4-yl)-acetamido]-8-oxo-5-thia-1-azabicyclo[4.2.0]oct-2-ene (product 3C) (2 g) in the form of a hard yellow foam.

Infra-red spectrum (CHBr₃), characteristic bands (cm⁻¹): 3,390, 2,820, 1,785, 1,715, 1,680, 1,585, 1,515, 1,490, 1,455, 1,050, 940, 750, 740.

Proton NMR spectrum (350 MHz, d₆-DMSO, δ in ppm, J in Hz): 1.07 (t, J=7, 6H, 2—CH₃); 3.30 (s, >N—CH₃); 3.40 to 3.68 (2m, 4H, (—O—CH₂—CH₃)₂); 3.68 and 3.92 (2d, J=18, 2H, —S—CH₂—); 3.83 (s, 3H, =N—OCH₃); 3.95 (d, J=6, 2H, >N—CH₂—); 4.85 (t, J=6, 1H,

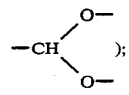

5.27 (d, J=4, 1H, —H in the 6-position); 5.79 (dd, J=4 and 9, 1H, —H in the 7-position); 6.75 (s, 1H, —H of the thiazole); 6.96 (s, 1H, —COO—CH(C₆H₅)₂); 6.98 and 7.05 (2d, J=16, 2H, —CH=CH—S—); 8.82 (s, 1H, —NH—C(C₆H₅)₃); 9.63 (d, J=9, 1H, —CO—NH—).

A solution of product (3C) (1.9 g) in formic acid (20 cc) is stirred for 30 minutes at 50° C. and then diluted with water (2 cc) and stirred for 10 minutes at 50° C. After cooling to 20° C., the reaction mixture is filtered and the filtrate is concentrated under reduced pressure (0.1 mm Hg; 0.013 kPa) at 35° C. The residue is triturated with ethanol (20 cc), which is evaporated off under reduced pressure (30 mm Hg; 4 kPa) at 40° C. This operation is repeated 3 times and the residue is then taken up in ethanol (30 cc). The solid is isolated on a vacuum filter and washed with ethanol (3×10 cc) and ethyl ether (3×10 cc) and dried. This yields the E form of the syn isomer of 7-[2-(2-aminothiazol-4-yl)-2--methoxyiminoacetamido]-2-carboxy-3-[2-(5,6-dioxo-1-formylmethyl-4-methyl-1,4,5,6-tetrahydro-1,2,4-triazin-3-yl)thiovinyl]-8-oxo-5-thia-1-azabicyclo[4.2.0]oct-2-ene (product R3) (0.96 g) in the form of a cream-coloured solid.

Infra-red spectrum (KBr), characteristic bands (cm⁻¹): 3,700—2,200, 1,770, 1,710, 1,675, 1,580, 1,550, 1,040.

Proton NMR spectrum (350 MHz, CF₃COOD, δ in ppm, J in Hz): 3.66 (s, 3H, >N—CH₃); 3.85 (s broad, 2H, —S—CH₂—); 4.31 (s, 3H, =N—O—CH₃); 5.13 (s broad, 2H, >N—CH₂—); 5.38 (d, J=4, 1H, —H in the 6-position); 6.02 (d, J=4, 1H, —H in the 7-position); 7.22 and 7.73 (2d, J=16, 2H, —CH=CH—S—); 7.48 (s, 1H, —H of the thiazole); 9.74 (s, 1H,

1-(2,2-Diethoxyethyl)-5,6-dioxo-4-methyl-3-thioxoperhydro-1,2,4-triazine can be prepared in the following manner:

1-(2,2-Diethoxyethyl)-1-ethoxalyl-4-methylthiosemicarbazide (8.8 g) is treated with potassium t-butylate (3.08 g) in dry t-butanol (60 cc) for 2 hours at 25° C. The reaction mixture is diluted with ether (50 cc). The precipitate of the potassium salt of the expected product is isolated on a filter, washed with ether (10 cc) and then taken up in water (30 cc). The solution obtained is acidified to pH 3 with 4N hydrochloric acid. The precipitate is isolated on a filter, washed with water (10 cc) and ethyl ether (10 cc) and then dried under reduced pressure (2 mm Hg; 0.27 kPa) at 20° C. This yields 1-(2,2-diethoxyethyl)-5,6-dioxo-4-methyl-3-thioxo-perhydro-1,2,4-triazine (3.65 g) in the form of white crystals, m.p.=136°–138° C.

1-(2,2-Diethoxyethyl)-1-ethoxalyl-4-methylthiosemicarbazide can be obtained in the following manner:

1-(2,2-Diethoxyethyl)-4-methylthiosemicarbazide (19.4 g), in dry methylene chloride (200 cc), is treated with pyridine (7.1 cc) and ethoxalyl chloride (9.85 cc) for 1 hour at 2° C. and then for a 16 hours at 25° C.; after the mixture has been washed with water (100 cc), dried over magnesium sulphate and concentrated to dryness under reduced pressure (30 mm Hg; 4 kPa) at 30° C., the residue is crystallised from ethyl ether (40 cc). This yields 1-(2,2-diethoxyethyl)-1-ethoxalyl-4-methylthiosemicarbazide (8.5 g) in the form of white crystals (m.p.=122° C.).

1-(2,2-Diethoxyethyl)-4-methylthiosemicarbazide can be prepared in the following manner:

1-(2,2-Diethoxyacetyl)-4-methylthiosemicarbazide (39.3 g) is reduced with lithium aluminium hydride (18 g) in dry tetrahydrofuran (500 cc) for 1 hour 30 minutes at 25° C. and then for 1 hour under reflux. This yields 1-(2,2-diethoxyethyl)-4-methylthiosemicarbazide (26.4 g) in the form of a colourless oil.

Infra-red spectrum (CCl₄), characteristic bands (cm⁻¹): 3,360, 3,200, 1,550, 1,240, 1,130, 1,060.

Mass spectrum: m/e=221, 175, 146.

1-(2,2-Diethoxyacetyl)-4-methylthiosemicarbazide can be prepared in the following manner:

Diethoxyacetic acid hydrazide (31.5 g) is treated, in ethyl ether (200 cc), with methyl isocyanate (14.6 g) for 20 hours at between 20° and 30° C. 1-(2,2-diethoxyacetyl)-4-methylthiosemicarbazide crystallises from the medium.

(Weight: 42 g; m.p.=116°-118° C.).

The dihalogen intermediates of the products according to the invention can be used in the following manner:

REFERENCE EXAMPLE 4

A solution of 2-benzhydryloxycarbonyl-7-t-butoxycarbonylamino-3-(2,2,-dichloroethyl)-8-oxo-5-thia-1-azabicyclo[4.2.0]oct-2-ene-5-oxide (product 4A) (1.09 g), 4-(2,2-dimethoxyethyl)-5,6-dioxo-3-thioxo-perhydro-1,2,4-triazine (0.49 g) and N,N-diisopropylethylamine (0.77 cc) in N,N-dimethylformamide (20 cc) is stirred for 16 hours at 25° C. and for 4 hours at 60° C. and is then cooled and diluted with methylene chloride (200 cc). The solution obtained is washed successively with a saturated solution of sodium chloride (2×100 cc), a saturated solution of sodium bicarbonate (2×100 cc) and distilled water (2×100 cc) and then dried over sodium sulphate and concentrated to dryness under reduced pressure; the residue is chromatographed on a column of silica gel (0.04–0.06) (diameter of the column: 3 cm, height: 30 cm), elution being carried out under a pressure of 50 kPa with ethyl acetate and approximately 50 cc fractions being collected. Fractions 7 to 15, containing the pure product, are combined and evaporated to dryness. This yields 2-benzhydryloxycarbonyl-7-t-butoxycarbonylamino-3-{2-[4-(2,2-dimethoxyethyl)-5,6-dioxo-1,4,5,6-tetrahydro-1,2,4-triazin-3-yl]-thiovinyl}-8-oxo-5-thia-1-azabicyclo[4.2.0]oct-2-ene-5-oxide (E form) (0.7 g), the characteristics of which are identical to those of the product (2B) described in Reference Example 2.

This product can be used as described above in Reference Example 2.

REFERENCE EXAMPLE 5

N,N-Diisopropylethylamine (0.04 cc) is added to a solution of the syn isomer of 2-benzhydryloxycarbonyl-3-(2,2-dichloroethyl)-7-[2-methoxyimino-2-(2-tritylaminiothiazol-4-yl)-acetamido]-8-oxo-5-thia-1-azabicyclo[4.2.0]-oct-2-ene-5-oxide (product 5A) (0.09 g) and 1-(2,2-diethoxyethyl)-5,6-dioxo-4-methyl-3-thioxo-perhydro-1,2,4-triazine (0.03 g) in dry N,N-dimethylformamide (2 cc), and the reaction mixture is stirred for 16 hours at 25° C. and then for 4 hours at 60° C. Chromatographic examination demonstrates the formation of the E form of the syn isomer of 2-benzhydryloxycarbonyl-3-{2-[1-(2,2-diethoxyethyl)-5,6-dioxo-4-methyl-1,4,5,6-tetrahydro-1,2,4-triazin-3-yl]-thiovinyl}-7-[2-methoxyimino-2-(2-tritylaminothiazol-4-yl)-acetamido]-8-oxo-5-thia-1-azabicyclo[4.2.0]oct-2-ene-5-oxide (product R5).

Rf=0.3 [Merck silica gel chromatography plate; eluent: 20/80 (by volume) mixture of cyclohexane and ethyl acetate].

This product can then be used as described above in Reference Example 3.

We claim:
1. A 3-vinylcephalosporin of the formula:

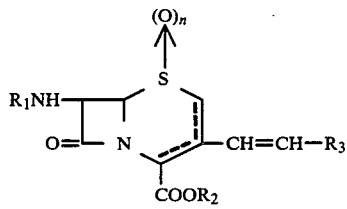

in which n is equal to 0 or 1,
1. (a) the symbol $R_1$ represents a hydrogen atom, a radical of the formula:

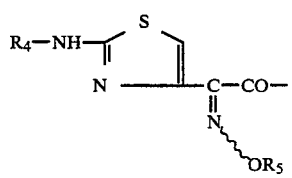

in the syn or anti form, (in which formula $R_4$ is a hydrogen atom or an amine-protecting radical and $R_5$ is a hydrogen atom, an alkyl, vinyl or cyanomethyl radical or an oxime-protecting group), an acyl radical of the formula:

in which $R_6$ is a hydrogen atom, an alkyl radical (optionally substituted by one or more halogen atoms or by a phenyl or phenoxy radical) or a phenyl radical, a radical of the formula:

in which $R_7$ is an unsubstituted branched alkyl radical or a linear or branched alkyl radical carrying one or more substituents (chosen from amongst halogen atoms, cyano, trialkylsilyl and phenyl radicals and the phenyl radical substituted by one or more alkoxy, nitro or phenyl radicals) or a vinyl, allyl or quinolyl radical, or a nitrophenylthio radical, or alternatively $R_1NH$— is replaced by a methyleneamino radical in which the methylene radical is substituted by a dialkylamino group or a phenyl group (which is itself optionally substituted by one or more methoxy or nitro radicals), and the symbol $R_2$ represents a hydrogen atom, a radical which can easily be removed by an enzymatic method, of the formula:

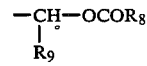

(in which $R_8$ represents an alkyl radical or the cyclohexyl radical and $R_9$ represents a hydrogen atom or an alkyl radical or a methoxymethyl, t-butyl, benzhydryl, nitrobenzyl or p-methoxybenzyl radical), or
(b) the symbol $R_1$ represents a hydrogen atom, an alkanoyl radical containing 1 to 8 carbon atoms or an alkanoyl radical containing 2 to 8 carbon atoms, which is substituted (by chlorine or bromine atoms), an azidoacetyl or cyanoacetyl radical, an acyl radical of the formula:

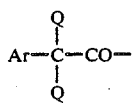

{in which Q is H or methyl and Ar represents a thien-2-yl, thien-3-yl, furan-2-yl, furan-3-yl, pyrrol-2-yl or pyrrol-3-yl radical or a phenyl radical (optionally substituted by halogen atoms, trifluoromethyl or hydroxyl radicals, alkyl radicals (containing 1 to 3 carbon atoms), alkoxy radicals (containing 1 to 3 carbon atoms) or cyano or nitro radicals, at least one of which is located in the meta-position or para-position of the phenyl)}, an acyl radical of the formula:

in which X is oxygen or sulphur and Ar is defined as above, or Ar—X— represents pyrid-4-yl-thio, an acyl radical of the formula:

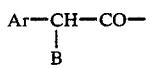 (VIII)

in which Ar is defined as above and B represents an amino radical, an amino radical protected by a benzyloxycarbonyl, alkoxycarbonyl, cyclopentyloxycarbonyl, cyclohexyloxycarbonyl, benzhydryloxycarbonyl, trityl or 2,2,2-trichloroethoxycarbonyl group, a sulpho radical, a hydroxyl or carboxyl radical {optionally protected by esterification (with respectively an alkanoic acid or an alcohol containing 1 to 6 carbon atoms)} or an azido, cyano or carbamoyl radical, a (3-sydnone)-2-alkanoyl radical (the alkanoyl part of which contains 1 to 3 carbon atoms), an acyl radical of the formula:

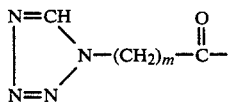

in which m is 0 to 2, or a 5-aminodipoyl radical {in which the amino group is optionally protected by an alkanoyl radical (containing 1 to 3 carbon atoms and optionally substituted by a chlorine atom) and in which the carboxyl group is protected by a benzhydryl or 2,2,2-trichloroethyl radical, a t-alkyl radical (containing 4 to 6 carbon atoms) or a nitrobenzyl radical}, and the symbol $R_2$ represents a t-alkyl radical containing 4 to 6 carbon atoms, a t-alkenyl radical containing 6 or 7 carbon atoms, a t-alkynyl radical containing 6 or 7 carbon atoms, a benzyl, -methoxybenzyl, nitrobenzyl, 2,2,2-trichloroethyl, benzhydryl, succinimidomethyl or phthalimidomethyl radical or a hydrogen atom, and the symbol $R_3$ represents a chlorine, bromine or iodine atom or 2. the symbol $R_1$ represents a radical of the formula (II) in which $R_4$ is defined as under 1.(a) and $R_5$ represents a radical of the formula:

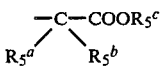 (IIa)

(in which $R^a_5$ and $R^b_5$, which are identical or different, represent hydrogen atoms or alkyl radicals, or together form an alkylene radical containing 2 or 3 carbon atoms, and $R^c_5$ represents a hydrogen atom or an acid-protecting radical), the symbol $R_2$ is defined as above under 1.(a) and the symbol $R_3$ represents a radical of the formula:

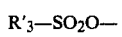

or

(in which formulae $R'_3$ represents an alkyl, trifluoromethyl or trichloromethyl radical or a phenyl radical which is unsubstituted or substituted by a halogen atom or by an alkyl or nitro radical), and $R''_3$ is defined in the same way as $R'_3$ or represents an acylmethyl, 2-acylethyl, 2-acylpropyl, alkoxycarbonylmethyl, 2-alkoxycarbonylethyl or 2-alkoxycarbonylpropyl radical, or $R_3$ represents a chlorine, bromine or iodine atom, the above-mentioned alkyl or acyl portions or radicals being linear or branched (unless otherwise mentioned) and containing 1 to 4 carbon atoms, the product being in the form of a bicyclooct-2-ene or bicyclooct-3-ene if n=0, and in the form of a bicyclooct-2-ene if n=1, and the substituent in the 3-position being in the E or Z form, and also the mixtures of its isomers and its salts.

2. A product according to claim 1, wherein, n, $R_2$ and $R_3$ being defined as in claim 1 under 2., $R_1$ represents a radical of the formula:

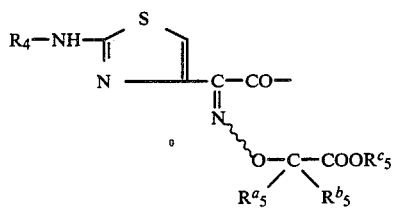

in the syn or anti form, in which formula $R^a_5$, $R^b_5$ and $R^c_5$ are defined as in claim 1 and $R_4$ is a hydrogen atom or a t-butoxycarbonyl, 2,2,2-trichloroethoxycarbonyl, chloroactyl, trichloroacetyl, trityl, benzyl, dibenzyl, benzyloxycarbonyl, p-nitrobenzyloxycarbonyl, p-methoxybenzyloxycarbonyl, formyl or trifluoroacetyl radical.

3. A product according to claim 1, wherein, n and $R_3$ being defined as in claim 1 under 1.(a), $R_1$ represents a radical of the formula:

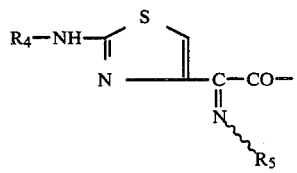

in the syn or anti form, in which formula $R_4$ is a hydrogen atom or a t-butoxycarbonyl, 2,2,2-trichloroethoxycarbonyl, chloroacetyl, trichloroacetyl, trityl, benzyl, dibenzyl, benzyloxycarbonyl, p-nitrobenzyloxycarbonyl or p-methoxybenzyloxycarbonyl radical and $R_5$ is a hydrogen atom or an alkyl, vinyl, cyanomethyl, trityl, tetrahydropyranyl or 2-methoxyprop-2-yl radical, and $R_2$ has a corresponding definition.

4. A product according to claim 1, wherein the protective radical $R^c{}_5$ is chosen from amongst methoxymethyl, t-butyl, benzhydryl, nitrobenzyl, benzyl and p-methoxybenzyl.

5. A product according to claim 1, wherein the radical $R_3$ represents a chlorine, bromine or iodine atom.

6. A product according to claim 1, having the E form in which $R_2$ represents hydrogen or benzhydryl and either $R_3$ represents chlorine, bromine or iodine, and $R_1$ represents hydrogen, alkoxycarbonyl, a radical of the formula (VIII) in which Ar is phenyl and B is amino or protected amino or a radical of the formula (II), syn form in which $R_4$ is trityl and $R_5$ is alkyl, or $R_3$ represents chlorine, bromine or iodine or tosyloxy and $R_1$ represents a radical of the formula (II), syn form in which $R_4$ is trityl and $R_5$ is a radical of the formula (IIa).

7. A product according to claim 1, having the E form in which $R_2$ represents hydrogen or benzhydryl and either $R_3$ represents chlorine and $R_1$ represents hydrogen, t-butoxycarbonyl, a radical of the formula (VIII) in which Ar is phenyl and B is amino or t-butoxycarbonylamino or a radical of the formula (II), syn form, in which $R_4$ is trityl and $R_5$ is methyl, or $R_3$ represents chlorine or tosyloxy, and $R_1$ represents a radical of the formula (II), syn form in which $R_4$ is trityl and $R_5$ is a radical of the formula (IIa).

8. 2-Benzhydryloxycarbonyl-7-{2-[(2-t-butoxycarbonylprop-2-yl)-oxyimino]-2-(2-tritylaminothiazol-4-yl)-acetamido}-8-oxo-3-(2-tosyloxyvinyl)-5-thia-azabicyclo[4.2.0]oct-2-ene.

9. 2-Benzhydryloxycarbonyl-7-t-butoxycarbonylamino-3-(2-chlorovinyl)-8-oxo-5-thia-1-azabicyclo[4.2.0]-oct-2-ene-5-oxide.

10. 2-Benzhydryloxycarbonyl-7-{2-[(2-t-butoxycarbonylprop-2-yl)-oxyimino]-2-(2-tritylaminothiazol-4-yl)-acetamido}-8-oxo-3-(2-tosyloxyvinyl)-5-thia-1-azabicyclo[4.2.0]oct-2-ene-5-oxide.

11. 2-Benzhydryloxycarbonyl-3-(2-chlorovinyl)-7-[2-methoxyimino-2-(2-tritylaminothiazol-4-yl)-acetamido]-8-oxo-5-thia-1-azabicyclo[4.2.0]oct-2-ene-5-oxide.

* * * * *